United States Patent
Morgan et al.

(10) Patent No.: US 12,286,437 B2
(45) Date of Patent: *Apr. 29, 2025

(54) CARDIAC SARCOMERE INHIBITORS

(71) Applicant: Cytokinetics, Inc., South San Francisco, CA (US)

(72) Inventors: Bradley P. Morgan, South San Francisco, CA (US); Chihyuan Chuang, South San Francisco, CA (US); Luke W. Ashcraft, South San Francisco, CA (US); Justin Ho, South San Francisco, CA (US); Alfredo Garcia, South San Francisco, CA (US); Aroop Chandra, Carmel, IN (US)

(73) Assignee: CYTOKINETICS, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/423,156

(22) Filed: Jan. 25, 2024

(65) Prior Publication Data
US 2024/0309011 A1 Sep. 19, 2024

Related U.S. Application Data

(63) Continuation of application No. 17/685,778, filed on Mar. 3, 2022, now Pat. No. 11,919,909.

(60) Provisional application No. 63/156,853, filed on Mar. 4, 2021.

(51) Int. Cl.
 C07D 487/10 (2006.01)
 A61P 9/04 (2006.01)

(52) U.S. Cl.
 CPC .............. *C07D 487/10* (2013.01); *A61P 9/04* (2018.01)

(58) Field of Classification Search
 None
 See application file for complete search history.

(56) References Cited

U.S. PATENT DOCUMENTS

| | | |
|---|---|---|
| 5,846,514 A | 12/1998 | Foster |
| 5,919,785 A | 7/1999 | Dinsmore |
| 6,334,997 B1 | 1/2002 | Foster |
| 8,592,426 B2 | 11/2013 | Aebi et al. |
| 9,181,200 B2 | 11/2015 | Oslob |
| 9,199,945 B2 | 12/2015 | Oslob |
| 9,663,516 B2 | 5/2017 | Oslob |
| 9,925,177 B2 | 3/2018 | Oslob |
| 10,836,755 B2 | 11/2020 | Chuang et al. |
| 11,414,424 B2 | 8/2022 | Chuang et al. |
| 11,472,796 B2 | 10/2022 | Chuang et al. |
| 11,919,909 B2 | 3/2024 | Morgan |
| 11,952,381 B2 | 4/2024 | Chuang et al. |
| 11,964,967 B2 | 4/2024 | Morgan |
| 12,065,436 B2 | 8/2024 | Chuang |
| 2006/0173183 A1 | 8/2006 | Powers |
| 2006/0241110 A1 | 10/2006 | Morgan |
| 2007/0078126 A1 | 4/2007 | Morgan et al. |
| 2007/0155713 A1 | 7/2007 | Nishizawa et al. |
| 2009/0192168 A1 | 7/2009 | Muci et al. |
| 2013/0018055 A1 | 1/2013 | Aebi et al. |
| 2013/0296335 A1 | 11/2013 | Morgan et al. |
| 2016/0176868 A1 | 6/2016 | Oslob et al. |
| 2016/0289211 A1 | 10/2016 | Ashcraft |
| 2019/0256504 A1 | 8/2019 | Chuang |
| 2019/0276435 A1 | 9/2019 | Shepard et al. |
| 2020/0000822 A1 | 1/2020 | Kruse |

(Continued)

FOREIGN PATENT DOCUMENTS

| | | |
|---|---|---|
| CL | 2008001170 A1 | 5/2009 |
| CL | 2014001772 A1 | 10/2014 |

(Continued)

OTHER PUBLICATIONS

Berge, S.M. et al. (Jan. 1977). "Pharmaceuticals Salts," J. Pharmaceutical Sciences 66(1):1-19.

Boxenbaum, H. (Nov. 9, 1981). "Interspecies Scaling, Allometry, Physiological Times, and the Ground Plan of Pharmacokinetics," Journal of Pharmacokinetics and Biopharmaceutics 10(2):201-227.

Caputo, S. et al. (Nov. 28, 2017). "Diversity-Oriented Synthesis of Various Enantiopure Heterocycles by Coupling Organocatalysis with Multicomponent Reactions," European J. of Chem. 2017(45):6619-6628.

(Continued)

*Primary Examiner* — Po-Chih Chen
(74) *Attorney, Agent, or Firm* — MORRISON & FOERSTER LLP

(57) ABSTRACT

Provided are compounds of Formula (I):

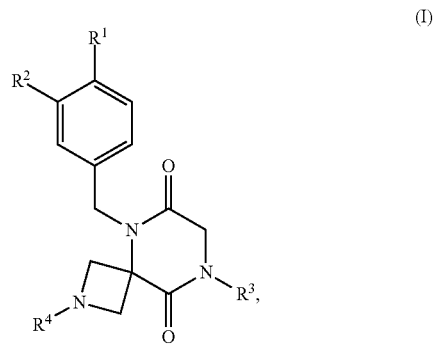

or stereoisomer or tautomer thereof, or a pharmaceutically acceptable salt of any of the foregoing, wherein $R^1$, $R^2$, $R^3$, and $R^4$ are as defined herein. Also provided is a pharmaceutically acceptable composition comprising a compound of Formula (I), or stereoisomer or tautomer thereof, or a pharmaceutically acceptable salt of any of the foregoing. Also provided are methods of using a compound of Formula (I), or stereoisomer or tautomer thereof, or a pharmaceutically acceptable salt of any of the foregoing.

20 Claims, 1 Drawing Sheet

(56) References Cited

U.S. PATENT DOCUMENTS

| | | | |
|---|---|---|---|
| 2020/0054636 | A1 | 2/2020 | Semigran et al. |
| 2020/0109148 | A1 | 4/2020 | Chuang |
| 2021/0147399 | A1 | 5/2021 | Chuang et al. |
| 2021/0253563 | A1 | 8/2021 | Morgan et al. |
| 2021/0276991 | A1 | 9/2021 | Morgan et al. |
| 2021/0323913 | A1 | 10/2021 | Martin et al. |
| 2022/0306642 | A1 | 9/2022 | Morgan et al. |
| 2023/0090256 | A1 | 3/2023 | Chuang et al. |
| 2023/0119665 | A1 | 4/2023 | Chuang et al. |
| 2024/0132498 | A1 | 4/2024 | Chuang |

FOREIGN PATENT DOCUMENTS

| | | | |
|---|---|---|---|
| CL | 2015003689 | A1 | 10/2016 |
| CL | 2020001871 | A1 | 10/2020 |
| CL | 2020002399 | A1 | 12/2020 |
| CL | 2021000443 | A1 | 7/2021 |
| CL | 2021000481 | A1 | 7/2021 |
| CL | 2021001083 | A1 | 9/2021 |
| CL | 2020002275 | A1 | 9/2022 |
| CL | 2023002605 | A1 | 6/2024 |
| CL | 2024001620 | A1 | 11/2024 |
| CN | 105473576 | A | 4/2016 |
| CN | 114456163 | A | 5/2022 |
| CN | 114516843 | A | 5/2022 |
| CN | 114539229 | A | 5/2022 |
| CN | 114539257 | A | 5/2022 |
| EA | 020138 | B1 | 8/2014 |
| JP | 2016522263 | A | 7/2016 |
| WO | 2003059265 | A2 | 7/2003 |
| WO | 2003059265 | A3 | 6/2004 |
| WO | 2004064730 | A2 | 8/2004 |
| WO | 2006009726 | A2 | 1/2006 |
| WO | 2006060318 | A2 | 6/2006 |
| WO | 2006116150 | A1 | 11/2006 |
| WO | 2007078815 | A2 | 7/2007 |
| WO | 2007117180 | A1 | 10/2007 |
| WO | 2008130320 | A2 | 10/2008 |
| WO | 2008130320 | A3 | 12/2008 |
| WO | 2010130796 | A1 | 11/2010 |
| WO | 2012101011 | A2 | 8/2012 |
| WO | 2013108227 | A1 | 7/2013 |
| WO | 2014205223 | A1 | 12/2014 |
| WO | 2014205234 | A1 | 12/2014 |
| WO | 2017103219 | A1 | 6/2017 |
| WO | 2017103223 | A1 | 6/2017 |
| WO | 2017222951 | A1 | 12/2017 |
| WO | 2018063955 | A1 | 4/2018 |
| WO | 2018089433 | A1 | 5/2018 |
| WO | 2019144041 | A1 | 7/2019 |
| WO | 2019182925 | A1 | 9/2019 |
| WO | 2019226213 | A2 | 11/2019 |
| WO | 2019226213 | A3 | 1/2020 |
| WO | 2020005887 | A1 | 1/2020 |
| WO | 2020005888 | A1 | 1/2020 |
| WO | 2020047323 | A1 | 3/2020 |
| WO | 2020047447 | A1 | 3/2020 |
| WO | 2020092208 | A1 | 5/2020 |
| WO | 2021011807 | A1 | 1/2021 |
| WO | 2021011808 | A1 | 1/2021 |
| WO | 2021092598 | A1 | 5/2021 |
| WO | 2022047004 | A1 | 3/2022 |
| WO | 2022105852 | A1 | 5/2022 |
| WO | 2022111498 | A1 | 6/2022 |
| WO | 2022187501 | A1 | 9/2022 |

OTHER PUBLICATIONS

CAS (Dec. 5, 2011). "STN Registry Database Entry for CAS RN 1348860-91-2," accessed Feb. 13, 2021, 1 page.

CAS (Nov. 12, 2007). "STN Registry Database entry for CAS RN 953060-71-4," accessed Jul. 15, 2021, 5 pages.

Dahl, L.K. et al. (Jun. 1, 1962). "Effects of Chronic Excess Salt Ingestion Evidence That Genetic Factors Play an Important Role in Susceptibility to Experimental Hypertension," J Exp Med. 115(6):1173-1190.

Database Registry (Jun. 18, 2008). RN-1028938-65-9 Emory MLSC database: "2, 5-Piperazinediones, 4-[(4-chlorophenyl)methyl]-3-(4-methoxyphenyl)-1-(2-phenylethyl)-," Chemical Abstracts Service, 1 page.

Database Registry (Jun. 24, 2008). RN-1030378-92-7 Emory MLSC database: "1-Piperazineacetamide, 3-(2-fluorophenyl)-N-(2-methylcyclohexyl)-4-[(4-methylphenyl)methyl]-2,5-dioxo," Chemical Abstracts Service, 1 page.

Database Registry (Nov. 4, 2011). RN-1340679-26-6 ChemDiv, Inc.: "2, 5-Piperazinedione, 1-(-3_methylbutyl)-4-(phenylmethyl)-3-(3-pyridinyl)," Chemical Abstracts Service, 3 pages.

Dean, D.C. (2000). "Recent Advances in the Synthesis and Applications of Radiolabeled Compounds for the Drug Discovery and Development," Curr. Pharm. Des. 6(10): Preface Only, 1 page.

Evans, A.E. (Mar. 1981, e-pub. Jan. 9, 2007). "Synthesis of Radiolabelled Compounds," J Radio Anal. Chem. 64(1-2):9-32.

Fillmore, N. et al. (2018). "Uncoupling of Glycolysis from Glucose Oxidation Accompanies the Development of Heart Failure with Preserved Ejection Fraction," Mol. Med. 24(3):1-12.

Geisterfer-Lowrance, A.A.T. et al. (May 3, 1996). "A Mouse Model of Familial Hypertrophic Cardiomyopathy," Science 272(5262):731-734.

Green, E. M. et al. (Feb. 5, 2016). "A Small-Molecule Inhibitor of Sarcomere Contractility Suppresses Hypertrophic Cardiomyopathy in Mice," Science 351(6273):617-621, 7 pages.

Guazzi, M. et al. (Sep. 26, 2017). "Cardiopulmonary Exercise Testing: What is its Value?," J. Am. Coll. Cardiol. 70(13):1618-1636.

Guyonnet, M. et al. (Jan. 6, 2012, e-pub. Dec. 16, 2011). "Synthesis of Tricyclic Nitrogen Heterocycles by a Sequence of Palladium-Catalyzed N—H and C(sp3)—H Arylations," Org Lett. 14(1):398-401.

Hargrave, J.D. et al. (Nov. 21, 2010, e-pub. Sep. 8, 2010). "Rhodium-Catalysed Conjugate Addition of Arylboronic Acids to Enantiopure Dehydroamino Acid Derivatives," Org. Biomol. Chem. 8(22):5120-5125.

Hartung, A. et al. (Dec. 11, 2012). "One-Pot Ugi/Aza-Michael Synthesis of Highly Substituted 2,5-Diketopiperazines with Anti-Proliferative Properties," Molecules Online 17(12):14685-14699.

International Preliminary Report on Patentability issued Aug. 29, 2023, for Patent Application No. PCT/US2022/018725, filed Mar. 3, 2022, 6 pages.

International Preliminary Report on Patentability mailed Jan. 27, 2022, for Patent Application No. PCT/US2020/042387, filed Jul. 16, 2020, 8 pages.

International Preliminary Report on Patentability mailed Jan. 27, 2022, for Patent Application No. PCT/US2020/042389, filed Jul. 16, 2020, 8 pages.

International Preliminary Report on Patentability mailed Jan. 27, 2022, for Patent Application No. PCT/US2020/042390, filed Jul. 16, 2020, 8 pages.

International Preliminary Report on Patentability mailed Jan. 7, 2021, for Patent Application No. PCT/US2019/038907, filed Jun. 25, 2019, 7 pages.

International Preliminary Report on Patentability mailed Jan. 7, 2021, for Patent Application No. PCT/US2019/038908, filed Jun. 25, 2019, 8 pages.

International Preliminary Report on Patentability mailed Jul. 30, 2020, for Patent Application No. PCT/US2019/014344, filed Jan. 18, 2019, 11 pages.

International Search Report and Written Opinion of the International Searching Authority mailed Aug. 28, 2019, for PCT Patent Application No. PCT/US2019/038907, filed Jun. 25, 2019, 19 pages.

International Search Report and Written Opinion of the International Searching Authority mailed Aug. 28, 2019, for PCT Patent Application No. PCT/US2019/038908, filed Jun. 25, 2019, 14 pages.

(56) References Cited

OTHER PUBLICATIONS

International Search Report and Written Opinion of the International Searching Authority mailed May 20, 2019, for PCT Patent Application No. PCT/US2019/014344, filed Jan. 18, 2019, 19 pages.
International Search Report and Written Opinion of the International Searching Authority mailed Nov. 10, 2020, for PCT Patent Application No. PCT/US2020/042387, filed Jul. 16, 2020, 13 pages.
International Search Report and Written Opinion of the International Searching Authority mailed Nov. 5, 2020, for PCT Patent Application No. PCT/US2020/042389, filed Jul. 16, 2020, 13 pages.
International Search Report and Written Opinion of the International Searching Authority mailed Nov. 6, 2020, for PCT Patent Application No. PCT/US2020/042390, filed Jul. 16, 2020, 14 pages.
International Search Report and Written Opinion of the International Searching Authority mailed on May 17, 2022, for PCT Patent Application No. PCT/US2022/018725, filed on Mar. 3, 2022, 12 pages.
Invitation to Pay Additional Fees mailed Mar. 28, 2019, for PCT Patent Application No. PCT/US2019/014344, filed Jan. 18, 2019, 14 pages.
Ito, N. (Jan. 2003). "A Medium-Term Rat Liver Bioassay For Rapid In Vivo Detection of Carcinogenic Potential of Chemicals," Cancer Science 94(1):3-8.
Jackson, P. et al. (Aug. 22, 2018). "Appendage and Scaffold Diverse Fully Functionalized Small-Molecule Probes via a Minimalist Terminal Alkyne-Aliphatic Diazirine Isocyanide," J. Org. Chem. 83(18):11245-11253.
Jiang, J. et al. (Oct. 4, 2013, e-pub. Jul. 14, 2014). "Allele-Specific Silencing of Mutant Myh6 Allele in Mice Suppresses Hypertrophic Cardiomyopathy," Science 342(6154):111-114, 11 pages.
Kabalka, G.W. et al. (1989). "The Synthesis of Radiolabeled Compounds via Organometallic Intermediates," Tetrahedron 45(21):6601-6621.
Kaim, L.E. et al. (2007, e-pub. Jan. 24, 2007). "New Indolizine Template from the Ugi Reaction," Synlett 2(1):227-230.
Kim-Mitsuyama, S. et al. (Oct. 2004). "Additive Beneficial Effects of the Combination of a Calcium Channel Blocker and an Angiotensin Blocker on a Hypertensive Rat-Heart Failure Model," Hypertens Res. 27(10):771-779.
Lee, M. et al. (May 25, 2016). "Convenient asymmetric synthesis of 1,3,4,6-tetrasubstituted 2,5-diketopiperazines," Arkivoc 2016(4):100-113.
Lee, M. et al. (May 19, 2016). " Stereoselective Nucleophile Substitution of [alpha]-Bromo Tertiary Amides for Asymmetric Synthesis of Highly Substituted 2,5-Diketopiperazines," Bull. Korean Chem. Soc. 37(6):981-984.
Lesma, G. et al. (Jun. 18, 2014). "Asymmetric Ugi 3CR on isatin-derived ketimine: synthesis of chiral 3,3-disubstituted 3-aminooxindole derivatives," Beilstein Journal of Organic Chemistry 10:1383-1389.
Mahmood, I. et al. (1996). "Interspecies Scaling: A Comparative Study for the Prediction of Clearance and Volume Using Two or More Than Two Species," Life Sciences, 59(7):579-585.
Malhotra, R. et al. (Aug. 2016, e-pub. Jun. 8, 2016). "Cardiopulmonary Exercise Testing in Heart Failure," JACC Heart Fail 4(8):607-616.

Mamoun, O. et al. (1995, e-pub. Sep. 23, 2006). "Synthesis of Methyl 3-Amino-3-pyrrolidinecarboxylates: a Convenient Access to Cucurbitine and Analogues," Synthetic Communications 25(9):1295-1302.
Parker, M.F.L. et al. (Jan. 23, 2014). "Acceleration of an Aromatic Claisen Rearrangement Via a Designed Spiroligozyme Catalyst that Mimics the Ketosteroid Isomerase Catalytic Dyad," J. American Chem. Soc. 136 (10):3817-3827.
Pettersson, M. et al. (Oct. 1, 2015). "Design, Synthesis and Evaluation of 2,5-Diketopiperazines as Inhibitors of the MDM2-p53 Interaction," PLOS ONE 10(10):e0137867, 19 pages.
Philipson, D. J. et al. (2017, e-pub. Aug. 31, 2017). "Emerging Pharmacologic and Structural Therapies For Hypertrophic Cardiomyopathy," Heart Fail Rev. 22(6):879-888.
Pyne, S.G. et al. (1993). "Asymmetric Synthesis of Chiral Cyclic Amino Acids by Diels-Alder Reactions of (2S)- and (2R)-4-Methyleneoxazolidin-5-ones," Aust. J Chem. 46(1):73-93.
Rowin, E.J. et al. (Nov. 2017). "Role of Exercise Testing in Hypertrophic Cardiomyopathy," JACC: Cariovasc Imaging. 10(11):1374-1386.
Sakata, Y. et al. (Jan. 2001). "Renin Angiotensin System-Dependent Hypertrophy as a Contributor to Heart Failure in Hypertensive Rats: Different Characteristics From Renin Angiotensin System-Independent Hypertrophy," J. Am. Coll. Cardiol. 37(1):293-299.
Santra, S. et al. (Apr. 1, 2011, e-pub. Feb. 25, 2011). "A Rapid, One-Pot, Microwave-Influenced Synthesis of Spiro-2,5-diketopiperazines via a Cascade Ugi/6-Exo-Trig Aza-Michael Reaction," Journal of Organic Chemistry 76(7):2261-2264.
Taub, P.R. et al. (Oct. 1, 2013). "Perturbations in Skeletal Muscle Sarcomere Structure in Patients with Heart Failure and Type 2 Diabetes: Restorative Effects of (−)-epicatechin-rich Cocoa," Clinical Science 125(8):383-389.
U.S. Appl. No. 18/587,730, filed Feb. 26, 2024, for Chuang Chihyuan et al. (U.S. Patent Application is not submitted herewith pursuant to the waiver of 37 C.F.R. § 1.98(a)(2)(iii) issued by the Office on Sep. 21, 2004.).
U.S. Appl. No. 18/460,314, filed Sep. 1, 2023, for Chuang Chihyuan et al. (U.S. Patent Application is not submitted herewith pursuant to the waiver of 37 C.F.R. § 1.98(a)(2)(iii) issued by the Office on Sep. 21, 2004.).
Walvoord, R.R. et al. (Nov. 4, 2014). "Quantification of Electrophilic Activation by Hydrogen-Bonding Organocatalysts", J. American Chem. Soc. 136(45):16055-16065.
Williams, R. et al. (Nov. 3, 1992). "Asymmetric synthesis of S-(−)-Cucurbitine," Tetrahedron Letters 33(45):6755-6758.
Williams, R.M. et al. (Nov. 1982). "A New and Efficient Cyclization Reaction to Construct the Bicyclomycin Ring System: Synthesis of N, N'-Dimethyl-4-desmethylenebicyclomycin," Journal of the American Chemical Society 104(22):6092-6099.
Yates, P. et al. (Jan. 1, 1983). "Synthesis of Piperazine-2,5-diones Related to Bicyclomycin: 3-acetoxy-1,4-dibenzyl-3-[1-(2-methoxyethyl)-and 1-(2-hydroxyethyl)ethenyl]piperazine-2,5-dione. 1. Route Via Acyclic Intermediates," Canadian Journal Of Chemistry 61(3):519-528.
Yoshifuji, S. et al. (Aug. 1995). "Stereospecific Synthesis of (R)- and (S)-Baclofen and (R)- and (S)-PCPGABA [4-Amino-2-(4-chlorophenyl)butyric Acid] via (R)- and (S)-3-(4-Chlorophenyl)pyrrolidines," Chem Pharm Bull 42(8)1302-1306.
U.S. Appl. No. 18/762,390, filed Jul. 2, 2024, for Chuang Chihyuan et al. (U.S. Patent Application is not submitted herewith pursuant to the waiver of 37 C.F.R. § 1.98(a)(2)(iii) issued by the Office on Sep. 21, 2004.).

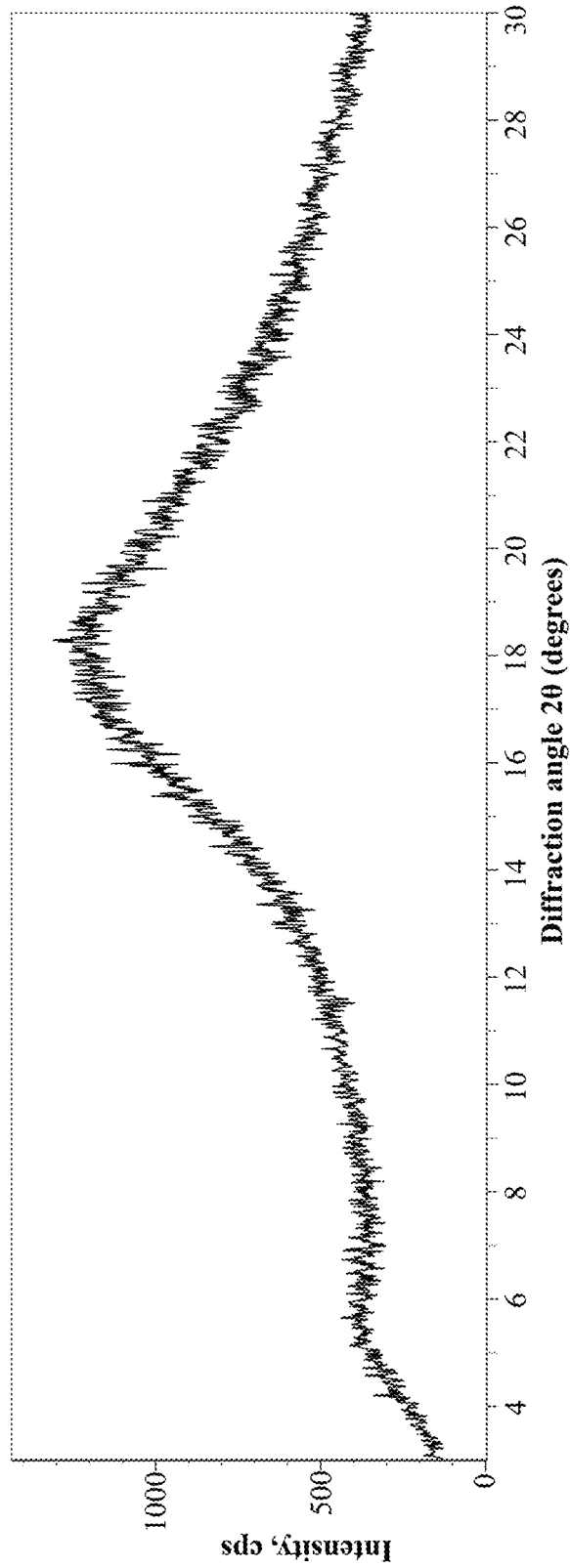

CARDIAC SARCOMERE INHIBITORS

CROSS REFERENCE TO RELATED APPLICATIONS

This application is a continuation of U.S. application Ser. No. 17/685,778, filed Mar. 3, 2022, which claims the priority benefit of U.S. Provisional Patent Application No. 63/156,853, filed Mar. 4, 2021, the disclosures of which are hereby incorporated herein by reference in their entirety.

FIELD

Provided herein are heterocyclic compounds, pharmaceutical compositions comprising such compounds, and methods of treating various cardiac diseases and conditions with such compounds.

BACKGROUND

The disclosure relates to certain chemical entities that selectively modulate the cardiac sarcomere, and specifically to certain chemical entities, pharmaceutical compositions and methods for treating various cardiac diseases and conditions.

The cardiac sarcomere is composed of a network of contractile and structural proteins that regulate cardiac muscle function. The components of the cardiac sarcomere present targets for the treatment of various cardiac diseases and conditions, for example by increasing contractility or facilitating complete relaxation to modulate systolic and diastolic function, respectively. The force and speed of cardiac muscle contraction is a major determinant of organ function and is modulated by the cyclical interactions of actin and myosin. Regulation of actin and myosin binding is determined by a network of myofilament regulatory proteins and the level of intracellular $Ca^{2+}$. The troponin complex and tropomyosin are thin filament proteins which govern the availability of actin binding sites, and the essential and regulatory light chains, and myosin binding protein C modulate the position and mechanical properties of myosin.

Abnormalities in the cardiac sarcomere have been identified as the driving cause for a variety of cardiac diseases and conditions, such as hypertrophic cardiomyopathy (HCM) and heart failure with preserved ejection fraction (HFpEF). Mutations in the proteins of the sarcomere cause disease by rendering the cardiac muscle either 'hyper' or 'hypo' contractile. Modulators of the cardiac sarcomere can be used to rebalance contractility and stop or reverse the course of disease.

Current agents that target the cardiac sarcomere, such as inotropes (drugs that increase the contractile ability of the heart) are poorly selective for cardiac tissue, which leads to recognized adverse effects that limit their use. These adverse effects include cell damage caused by an increased rate of energy expenditure, exacerbation of relaxation abnormalities, and potential arrhythmogenic side effects that may result from increased cytosolic $Ca^{2+}$ and cyclic AMP concentrations in the inotropically stimulated myocardium. Given the limitations of current agents, new approaches are needed to improve cardiac function in HCM and HFpEF.

There remains a great need for agents that exploit new mechanisms of action and which may have better outcomes in terms of relief of symptoms, safety, and patient mortality, both short-term and long-term. New agents with an improved therapeutic index over current agents will provide a means to achieve these clinical outcomes. The selectivity of agents directed at the cardiac sarcomere (for example, by targeting cardiac myosin) has been identified as an important means to achieve this improved therapeutic index. The present disclosure provides such agents (particularly cardiac sarcomere inhibitors) and methods for their use. These agents are allosteric inhibitors of cardiac myosin. Benefits of these compounds include a wider therapeutic index, less impact on cardiac relaxation, better pharmacokinetics, and better safety. Agents of the present disclosure are also useful in that they may allow for once-daily dosing for the methods of use described herein.

The present disclosure provides chemical entities, pharmaceutical compositions and methods for the treatment of heart failure including HCM and HFpEF. The compositions are inhibitors of the cardiac sarcomere, for example, inhibitors of cardiac myosin.

BRIEF SUMMARY

In one aspect, provided is a compound of Formula (I):

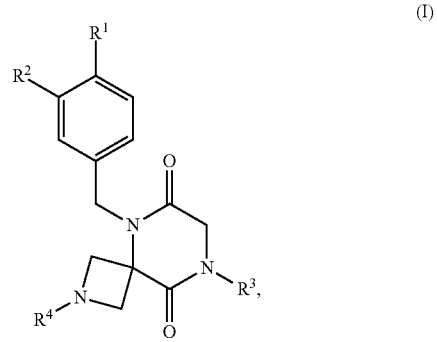

or a stereoisomer or tautomer thereof, or a pharmaceutically acceptable salt of any of the foregoing, wherein:
$R^1$ is halo or $C_{1-6}$haloalkyl;
$R^2$ is H, halo, or $C_{1-6}$alkyl;
$R^3$ is:
  (i) cyclohexyl, wherein the cyclohexyl is optionally substituted with one or more independently selected $C_{1-6}$alkyl or $C_{1-6}$haloalkyl substituents, or
  (ii) $C_{1-6}$alkyl; and
$R^4$ is:
  (i) —C(O)H,
  (ii) —C(O)$NH_2$,
  (iii)

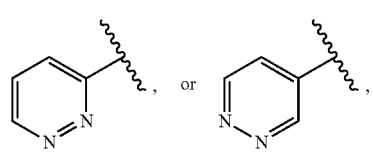 [SMILES: *c1cccnn1 ; *c1ccnnc1]

(iv) provided that:

(1) when $R^3$ is $C_{1-6}$alkyl, then $R^4$ is

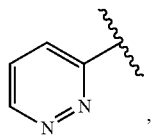 [SMILES: *c1cccnn1]

(2) when $R^3$ is iso-propyl, then the total number of halo atoms in $R^1$ and $R^2$ is at least two, and (3) when $R^3$ is cyclohexyl substituted with one or more independently selected $C_{1-6}$ haloalkyl substituents, then $R^4$ is other than —C(O)H.

In one aspect, provided herein is a compound of Formula (I-A):

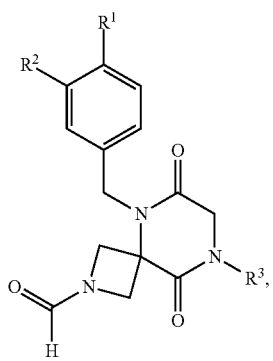

(I-A)

or a stereoisomer or tautomer thereof, or a pharmaceutically acceptable salt of any of the foregoing, wherein $R^1$, $R^2$, and $R^3$ are as described herein for a compound of Formula (I).

In one aspect, provided herein is a compound of Formula (I-B):

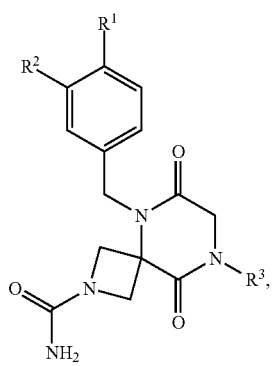

(I-B)

or a stereoisomer or tautomer thereof, or a pharmaceutically acceptable salt of any of the foregoing, wherein $R^1$, $R^2$, and $R^3$ are as described herein for a compound of Formula (I).

In one aspect, provided herein is a compound of Formula (I-C):

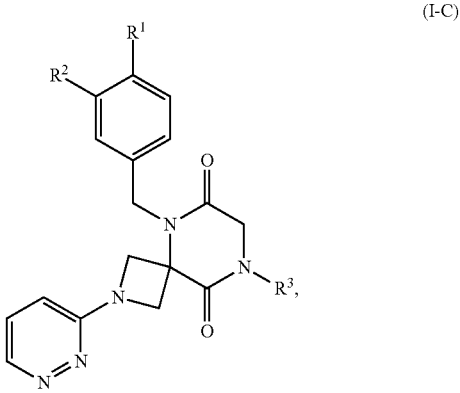

(I-C)

or a stereoisomer or tautomer thereof, or a pharmaceutically acceptable salt of any of the foregoing, wherein $R^1$, $R^2$, and $R^3$ are as described herein for a compound of Formula (I).

In one aspect, provided herein is a compound of Formula (I-D):

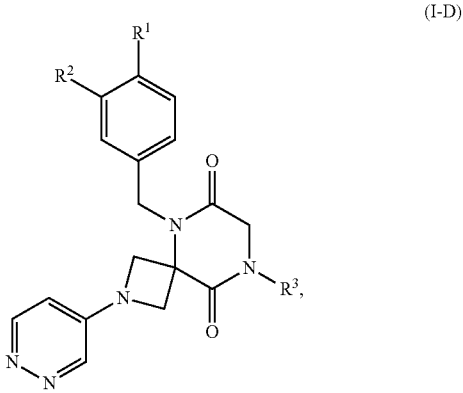

(I-D)

or a stereoisomer or tautomer thereof, or a pharmaceutically acceptable salt of any of the foregoing, wherein $R^1$, $R^2$, and $R^3$ are as described herein for a compound of Formula (I).

Provided in some aspects are compounds selected from the group consisting of compounds of Table 1, or stereoisomer or tautomer thereof, or a pharmaceutically acceptable salt of any of the foregoing.

Provided in some aspects is a pharmaceutical composition, comprising (i) a compound of Formula (I), or any variation or embodiment thereof, or a stereoisomer or tautomer thereof, or a pharmaceutically acceptable salt of any of the foregoing, and (ii) one or more pharmaceutically acceptable excipients.

Provided in some aspects are methods of treating heart disease in a subject in need thereof, the method comprising administering to the subject a compound of Formula (I), or any variation thereof, or stereoisomer or tautomer thereof, or a pharmaceutically acceptable salt of any of the foregoing, or a pharmaceutical composition containing a compound of Formula (I), or any variation thereof or stereoisomer or tautomer thereof, or a pharmaceutically acceptable salt of any of the foregoing. In some embodiments, the heart disease is hypertrophic cardiomyopathy (HCM). In some embodiments, the HCM is obstructive or nonobstructive or is caused by sarcomeric and/or non-sarcomeric mutations. In some embodiments, the heart disease is heart failure with preserved ejection fraction (HFpEF). In some embodiments, the heart disease is selected from the group consisting of diastolic dysfunction, primary or secondary restrictive cardiomyopathy, myocardial infarction, angina pectoris, and left ventricular outflow tract obstruction. In some embodiments, the heart disease is hypertensive heart disease, congenital heart disease, cardiac ischemia, coronary heart disease, diabetic heart disease, congestive heart failure, right heart failure, cardiorenal syndrome, or infiltrative cardiomyopathy. In some embodiments, the heart disease is a condition that is or is related to cardiac senescence and/or diastolic dysfunction due to aging. In some embodiments, the heart disease is a condition that is or is related to left ventricular hypertrophy and/or concentric left ventricular remodeling.

Provided in other aspects are methods of treating a disease or condition associated with HCM in a subject in need thereof, wherein the method comprises administering to the subject a compound of Formula (I), or any variation thereof, or stereoisomer or tautomer thereof, or a pharmaceutically acceptable salt of any of the foregoing, or a pharmaceutical composition containing a compound of Formula (I), or any variation thereof or stereoisomer or tautomer thereof, or a pharmaceutically acceptable salt of any of the foregoing. In some embodiments, the disease or condition is selected from the group consisting of Fabry's Disease, Danon Disease, mitochondrial cardiomyopathies, and Noonan Syndrome.

Provided in some aspects are methods of treating a disease or condition that is associated with secondary left ventricular wall thickening in a subject in need thereof, wherein the method comprises administering to the subject a compound of Formula (I), or any variation thereof, or stereoisomer or tautomer thereof, or a pharmaceutically acceptable salt of any of the foregoing, or a pharmaceutical composition containing a compound of Formula (I), or any variation thereof or stereoisomer or tautomer thereof, or a pharmaceutically acceptable salt of any of the foregoing. In some embodiments, the disease or condition is selected from the group consisting of hypertension, valvular heart diseases (such as aortic stenosis and Mitral valve regurgitation), metabolic syndromes (such as diabetes and obesity), end stage renal disease, scleroderma, sleep apnea, amyloidosis, Fabry's disease, Friedreich Ataxia, Danon disease, Noonan syndrome, and Pompe disease.

Provided in other aspects are methods of treating a disease or condition that is associated with small left ventricular cavity and cavity obliteration, hyperdynamic left ventricular contraction, myocardial ischemia, or cardiac fibrosis. Also provided are methods of treating muscular dystrophies (e.g., Duchenne muscular dystrophy) or glycogen storage diseases.

Also provided are methods of inhibiting the cardiac sarcomere, wherein the method involves contacting the cardiac sarcomere with a compound of Formula (I), or any variation thereof, or stereoisomer or tautomer thereof, or a pharmaceutically acceptable salt of any of the foregoing, or a pharmaceutical composition containing a compound of Formula (I), or any variation thereof or stereoisomer or tautomer thereof, or a pharmaceutically acceptable salt of any of the foregoing.

DESCRIPTION OF THE DRAWINGS

FIG. 1 shows an experimental X-ray powder diffraction (XRPD) pattern of an amorphous form of 5-(3,4-difluorobenzyl)-8-((1r,4r)-4-methylcyclohexyl)-6,9-dioxo-2,5,8-triazaspiro[3.5]nonane-2-carbaldehyde.

DETAILED DESCRIPTION

Definitions

As used in the present specification, the following words and phrases are generally intended to have the meanings as set forth below, except to the extent that the context in which they are used indicates otherwise.

Throughout this application, unless the context indicates otherwise, references to a compound of Formula (I) includes all subgroups of Formula (I) defined herein, such as Formula (I-A), (I-A1), (I-B), (I-B1), (I-C), (I-C1), (I-C2), (I-D), or (I-D1), including all substructures, subgenera, preferences, embodiments, examples and particular compounds defined and/or described herein. References to a compound of Formula (I) and subgroups thereof, such as Formula (I-A), (I-A1), (I-B), (I-B1), (I-C), (I-C1), (I-C2), (I-D), or (I-D1), include ionic forms, polymorphs, pseudopolymorphs, amorphous forms, solvates, co-crystals, chelates, isomers, tautomers, oxides (e.g., N-oxides, S-oxides), esters, prodrugs, isotopes and/or protected forms thereof. In some embodiments, references to a compound of Formula (I) and subgroups thereof, such as Formula (I-A), (I-A1), (I-B), (I-B1), (I-C), (I-C1), (I-C2), (I-D), or (I-D1), include polymorphs, solvates, co-crystals, isomers, tautomers and/or oxides thereof. In some embodiments, references to a compound of Formula (I) and subgroups thereof, such as Formula (I-A), (I-A1), (I-B), (I-B1), (I-C), (I-C1), (I-C2), (I-D), or (I-D1), include polymorphs, solvates, and/or co-crystals thereof. In some embodiments, references to a compound of Formula (I) and subgroups thereof, such as Formula (I-A), (I-A1), (I-B), (I-B1), (I-C), (I-C1), (I-C2), (I-D), or (I-D1), include isomers, tautomers and/or oxides thereof. In some embodiments, references to a compound of Formula (I) and subgroups thereof, such as Formula (I-A), (I-A1), (I-B), (I-B1), (I-C), (I-C1), (I-C2), (I-D), or (I-D1), include solvates thereof.

"Alkyl" encompasses straight and branched carbon chains having the indicated number of carbon atoms, for example, from 1 to 20 carbon atoms, or 1 to 8 carbon atoms, or 1 to 6 carbon atoms. For example, $C_{1-6}$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "propyl" includes n-propyl and isopropyl; and "butyl" includes n-butyl, sec-butyl, isobutyl and t-butyl. Examples of alkyl groups include, but are not limited to, methyl, ethyl, propyl, isopropyl, n-butyl, sec-butyl, tert-butyl, pentyl, 2-pentyl, 3-pentyl, isopentyl, neopentyl, hexyl, 2-hexyl, 3-hexyl, and 3-methylpentyl.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

"Halogen" or "halo" refers to fluoro, chloro, bromo, or iodo.

"Haloalkyl" refers to an alkyl moiety, as defined herein, wherein one or more of the hydrogen atoms in the alkyl moiety are replaced by one or more independently selected halo moieties. Examples of haloalkyl moieties include, but are not limited to, —CH$_2$F, —CHF$_2$, —CF$_3$, —CH$_2$—CH$_2$Cl, —CH$_2$—CHCl$_2$, —CH$_2$—CCl$_3$, and —CHF—CH$_2$Cl.

"Cyclohexyl" refers to a

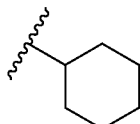

moiety.

Unless otherwise indicated, compounds disclosed and/or described herein include all possible enantiomers, diastereomers, meso isomers and other stereoisomeric forms, including racemic mixtures, optically pure forms and intermediate mixtures thereof. Enantiomers, diastereomers, meso isomers, and other stereoisomeric forms can be prepared using chiral synthons or chiral reagents, or resolved using conventional techniques. Unless specified otherwise, when the compounds disclosed and/or described herein contain olefinic double bonds or other centers of geometric asymmetry, it is intended that the compounds include both E and Z isomers. When the compounds described herein contain moieties capable of tautomerization, and unless specified otherwise, it is intended that the compounds include all possible tautomers.

"Protecting group" has the meaning conventionally associated with it in organic synthesis, i.e., a group that selectively blocks one or more reactive sites in a multifunctional compound such that a chemical reaction can be carried out selectively on another unprotected reactive site, and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999). For example, a "hydroxy protected form" contains at least one hydroxyl group protected with a hydroxyl protecting group. Likewise, amines and other reactive groups may similarly be protected.

The term "pharmaceutically acceptable salt" refers to a salt of any of the compounds herein which are known to be non-toxic and are commonly used in the pharmaceutical literature. In some embodiments, the pharmaceutically acceptable salt of a compound retains the biological effectiveness of the compounds described herein and are not biologically or otherwise undesirable. Examples of pharmaceutically acceptable salts can be found in Berge et al., Pharmaceutical Salts, *J. Pharmaceutical Sciences*, January 1977, 66(1), 1-19. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

If the compound described herein is obtained as an acid addition salt, the free base can be obtained by basifying a solution of the acid salt. Conversely, if the compound is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds (see, e.g., Berge et al., Pharmaceutical Salts, *J. Pharmaceutical Sciences*, January 1977, 66(1), 1-19). Those skilled in the art will recognize various synthetic methodologies that may be used to prepare pharmaceutically acceptable addition salts.

A "solvate" is formed by the interaction of a solvent and a compound. Suitable solvents include, for example, water and alcohols (e.g., ethanol). Solvates include hydrates having any ratio of compound to water, such as monohydrates, dihydrates and hemi-hydrates.

The term "substituted" means that the specified group or moiety bears one or more substituents, e.g., alkyl substituents or haloalkyl substituents. The term "unsubstituted" means that the specified group bears no substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

By "optional" or "optionally", it is meant that the subsequently described event or circumstance may or may not occur, and that the description includes instances where the event or circumstance occurs and instances in which it does not. For example, "optionally substituted cyclohexyl" encompasses both unsubstituted cyclohexyl and substituted cyclohexyl, as defined herein. It will be understood by those skilled in the art, with respect to any group containing one or more substituents, that such groups are not intended to introduce any substitution or substitution patterns that are sterically impractical, synthetically non-feasible, and/or inherently unstable. It will also be understood that where a group or moiety is optionally substituted, the disclosure includes both embodiments in which the group or moiety is substituted and embodiments in which the group or moiety is unsubstituted.

The compounds disclosed and/or described herein can be enriched isotopic forms, e.g., enriched in the content of $^2$H, $^3$H, $^{11}$C, $^{13}$C and/or $^{14}$C. In one embodiment, the compound contains at least one deuterium atom. Such deuterated forms can be made, for example, by the procedure described in U.S. Pat. Nos. 5,846,514 and 6,334,997. Such deuterated compounds may improve the efficacy and increase the duration of action of compounds disclosed and/or described herein. Deuterium substituted compounds can be synthesized using various methods, such as those described in: Dean, D., Recent Advances in the Synthesis and Applications of Radiolabeled Compounds for Drug Discovery and Development, *Curr. Pharm. Des.*, 2000; 6(10); Kabalka, G. et al., The Synthesis of Radiolabeled Compounds via Organometallic Intermediates, *Tetrahedron*, 1989, 45(21), 6601-21; and Evans, E., Synthesis of radiolabeled compounds, *J. Radioanal. Chem.*, 1981, 64(1-2), 9-32.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in pharmaceutical compositions is contemplated. Supplementary active ingredients can also be incorporated into the pharmaceutical compositions.

The terms "patient," "individual," and "subject" refer to an animal, such as a mammal, bird, or fish. In some embodiments, the patient or subject is a mammal. Mammals include, for example, mice, rats, dogs, cats, pigs, sheep, horses, cows and humans. In some embodiments, the patient or subject is a human, for example a human that has been or will be the object of treatment, observation or experiment. The compounds, compositions and methods described herein can be useful in both human therapy and veterinary applications.

As used herein, the term "therapeutic" refers to the ability to modulate the cardiac sarcomere. As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the chemical entity with the a target or due to the interaction of the chemical entity with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

The term "therapeutically effective amount" or "effective amount" refers to that amount of a compound disclosed and/or described herein that is sufficient to affect treatment, as defined herein, when administered to a patient in need of such treatment. A therapeutically effective amount of a compound may be an amount sufficient to treat a disease responsive to modulation of the cardiac sarcomere. The therapeutically effective amount will vary depending upon, for example, the subject and disease condition being treated, the weight and age of the subject, the severity of the disease condition, the particular compound, the dosing regimen to be followed, timing of administration, the manner of administration, all of which can readily be determined by one of ordinary skill in the art. The therapeutically effective amount may be ascertained experimentally, for example by assaying blood concentration of the chemical entity, or theoretically, by calculating bioavailability.

"Treatment" (and related terms, such as "treat", "treated", "treating") includes one or more of: inhibiting a disease or disorder; slowing or arresting the development of clinical symptoms of a disease or disorder; and/or relieving a disease or disorder (i.e., causing relief from or regression of clinical symptoms). The term covers both complete and partial reduction of the condition or disorder, and complete or partial reduction of clinical symptoms of a disease or disorder. Thus, compounds described and/or disclosed herein may prevent an existing disease or disorder from worsening, assist in the management of the disease or disorder, or reduce or eliminate the disease or disorder.

"ATPase" refers to an enzyme that hydrolyzes ATP. ATPases include proteins comprising molecular motors such as the myosins.

As used herein, "selective binding" or "selectively binding" refers to preferential binding to a target protein in one type of muscle or muscle fiber as opposed to other types. For example, a compound selectively binds to fast skeletal troponin C if the compound preferentially binds troponin C in the troponin complex of a fast skeletal muscle fiber or sarcomere in comparison with troponin C in the troponin complex of a slow muscle fiber or sarcomere or with troponin C in the troponin complex of a cardiac sarcomere.

It is understood that embodiments described herein as "comprising" include "consisting of" and "consisting essentially of" embodiments.

Compounds

Compounds and salts thereof (such as pharmaceutically acceptable salts) are detailed herein, including in the Brief Summary and in the appended claims. Also provided are the use of all of the compounds described herein, including any and all stereoisomers, including geometric isomers (cis/trans), E/Z isomers, enantiomers, diastereomers, and mixtures thereof in any ratio including racemic mixtures, salts and solvates of the compounds described herein, as well as methods of making such compounds. Any compound described herein may also be referred to as a drug.

In one aspect, provided are compounds of Formula (I):

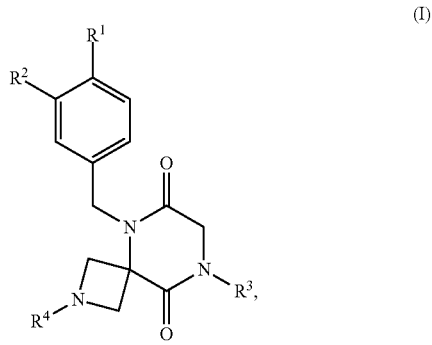

or a stereoisomer or tautomer thereof, or a pharmaceutically acceptable salt of any of the foregoing, wherein:

$R^1$ is halo or $C_{1-6}$haloalkyl;

$R^2$ is H, halo, or $C_{1-6}$alkyl;

$R^3$ is:
    (i) cyclohexyl, wherein the cyclohexyl is optionally substituted with one or more independently selected $C_{1-6}$alkyl or $C_{1-6}$haloalkyl substituents, or
    (ii) $C_{1-6}$alkyl; and R⁴ is:
(i) —C(O)H,
(ii) —C(O)NH₂,
(iii)

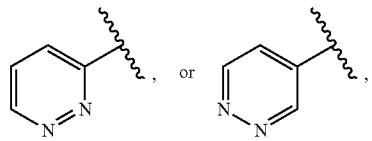 [SMILES: *c1cccnn1 ; *c1ccnnc1]

(iv)
provided that:
(1) when R³ is C₁₋₆alkyl, then R⁴ is

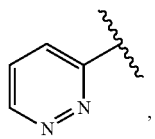

(2) when R³ is iso-propyl, then the total number of halo atoms in R¹ and R² is at least two, and
(3) when R³ is cyclohexyl substituted with one or more independently selected C₁₋₆ haloalkyl substituents, then R⁴ is other than —C(O)H.

In some embodiments, provided herein is a compound of Formula (I), or a stereoisomer or tautomer thereof, or a pharmaceutically acceptable salt of any of the foregoing, wherein R⁴ is —C(O)H. In some embodiments, provided herein is a compound of Formula (I), or a stereoisomer or tautomer thereof, or a pharmaceutically acceptable salt of any of the foregoing, wherein the compound is of Formula (I-A):

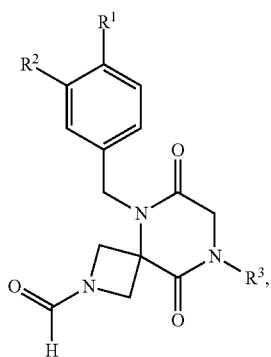

(I-A)

or a stereoisomer or tautomer thereof, or a pharmaceutically acceptable salt of any of the foregoing.

In some embodiments, provided herein is a compound of Formula (I), or a stereoisomer or tautomer thereof, or a pharmaceutically acceptable salt of any of the foregoing, wherein R⁴ is —C(O)NH₂. In some embodiments, provided herein is a compound of Formula (I), or a stereoisomer or tautomer thereof, or a pharmaceutically acceptable salt of any of the foregoing, wherein the compound is of Formula (I-B):

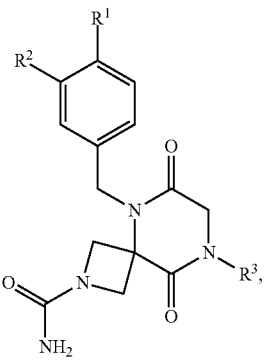

(I-B)

or a stereoisomer or tautomer thereof, or a pharmaceutically acceptable salt of any of the foregoing.

In some embodiments, provided herein is a compound of Formula (I), or a stereoisomer or tautomer thereof, or a pharmaceutically acceptable salt of any of the foregoing, wherein R⁴ is N

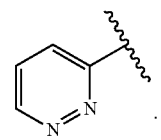 [SMILES: *c1cccnn1]

In some embodiments, provided herein is a compound of Formula (I), or a stereoisomer or tautomer thereof, or a pharmaceutically acceptable salt of any of the foregoing, wherein the compound is of Formula (I-C):

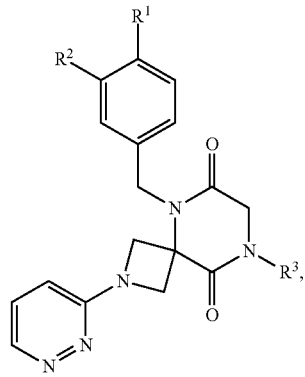

(I-C)

or a stereoisomer or tautomer thereof, or a pharmaceutically acceptable salt of any of the foregoing.

In some embodiments, provided herein is a compound of Formula (I), or a stereoisomer or tautomer thereof, or a pharmaceutically acceptable salt of any of the foregoing, wherein R⁴ is N

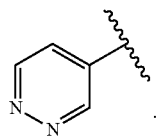 [SMILES: *c1ccnnc1]

In some embodiments, provided herein is a compound of Formula (I), or a stereoisomer or tautomer thereof, or a pharmaceutically acceptable salt of any of the foregoing, wherein the compound is of Formula (I-D):

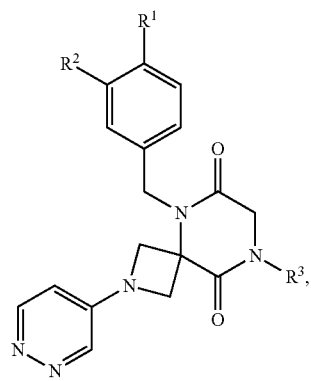

(I-D)

or a stereoisomer or tautomer thereof, or a pharmaceutically acceptable salt of any of the foregoing.

In some embodiments, provided herein is a compound of Formula (I), such as a compound of Formula (I-A), (I-B), (I-C), or (I-D), or a stereoisomer or tautomer thereof, or a pharmaceutically acceptable salt of any of the foregoing, wherein $R^3$ is cyclohexyl, wherein the cyclohexyl is optionally substituted with one or more independently selected $C_{1-6}$alkyl or $C_{1-6}$haloalkyl substituents. In some embodiments, $R^3$ is unsubstituted cyclohexyl. In some embodiments, $R^3$ is cyclohexyl, wherein the cyclohexyl is substituted with one or more independently selected $C_{1-6}$alkyl or $C_{1-6}$haloalkyl substituents.

In some embodiments, $R^3$ is cyclohexyl, wherein the cyclohexyl is optionally substituted with one or more independently selected $C_{1-6}$alkyl substituents. In some embodiments, $R^3$ is cyclohexyl, wherein the cyclohexyl is optionally substituted with one or more independently selected $C_{1-3}$alkyl substituents. In some embodiments, $R^3$ is cyclohexyl, wherein the cyclohexyl is optionally substituted with one or more independently selected methyl or ethyl substituents. In some embodiments, $R^3$ is cyclohexyl, wherein the cyclohexyl is optionally substituted with one or more methyl substituents. In some embodiments, $R^3$ is cyclohexyl, wherein the cyclohexyl is optionally substituted with one or more ethyl substituents. In some embodiments, $R^3$ is cyclohexyl, wherein the cyclohexyl is optionally substituted with one methyl substituent. In some embodiments, $R^3$ is cyclohexyl, wherein the cyclohexyl is optionally substituted with one ethyl substituent. In some embodiments, $R^3$ is

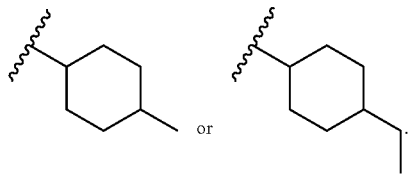

In some embodiments, $R^3$ is

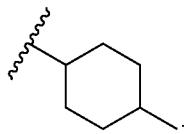 [SMILES: *C1CCC(C)CC1]

In some embodiments, $R^3$ is cyclohexyl, wherein the cyclohexyl is substituted with one or more independently selected $C_{1-6}$haloalkyl substituents. In some embodiments, $R^3$ is cyclohexyl, wherein the cyclohexyl is substituted with one or more independently selected $C_{1-3}$haloalkyl substituents. In some embodiments, $R^3$ is

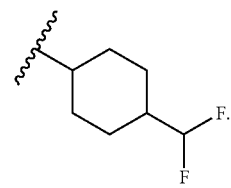 [SMILES: *C1CCC(C(F)F)CC1]

In some embodiments, $R^3$ is

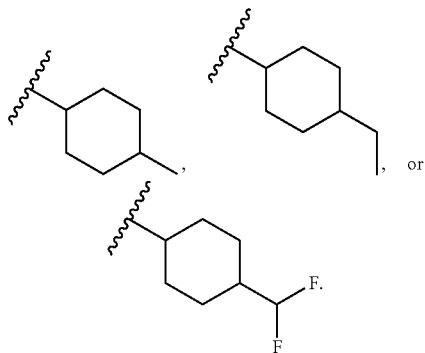

In some embodiments, provided herein is a compound of Formula (I) or Formula (I-A), or a stereoisomer or tautomer thereof, or a pharmaceutically acceptable salt of any of the foregoing, wherein $R^3$ is

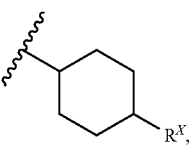

wherein $R^x$ is $C_{1-6}$alkyl, wherein the compound is of Formula (I-A1):

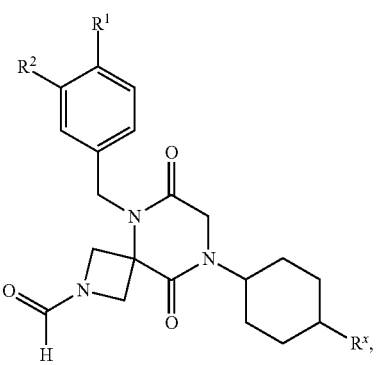

(I-A1)

or a stereoisomer or tautomer thereof, or a pharmaceutically acceptable salt of any of the foregoing. In some embodiments, $R^x$ is methyl.

In some embodiments, provided herein is a compound of Formula (I) or Formula (I-B), or a stereoisomer or tautomer thereof, or a pharmaceutically acceptable salt of any of the foregoing, wherein $R^3$ is

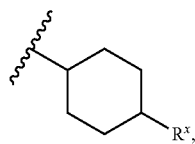

wherein $R^x$ is $C_{1-6}$alkyl or $C_{1-6}$haloalkyl, wherein the compound is of Formula (I-B1):

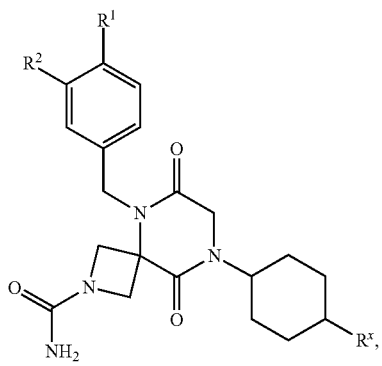

(I-B1)

or a stereoisomer or tautomer thereof, or a pharmaceutically acceptable salt of any of the foregoing. In some embodiments, provided herein is a compound of Formula (I-B1), or a stereoisomer or tautomer thereof, or a pharmaceutically acceptable salt of any of the foregoing, wherein $R^x$ is $C_{1-6}$alkyl. In some embodiments, $R^x$ is methyl.

In some embodiments, provided herein is a compound of Formula (I) or Formula (I-C), or a stereoisomer or tautomer thereof, or a pharmaceutically acceptable salt of any of the foregoing, wherein $R^3$ is

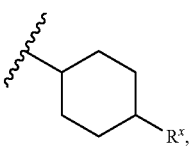

wherein $R^x$ is $C_{1-6}$alkyl or $C_{1-6}$haloalkyl, wherein the compound is of Formula (I-C1):

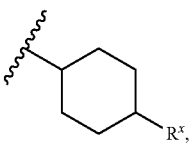

(I-C1)

or a stereoisomer or tautomer thereof, or a pharmaceutically acceptable salt of any of the foregoing. In some embodiments, provided herein is a compound of Formula (I-C1), or a stereoisomer or tautomer thereof, or a pharmaceutically acceptable salt of any of the foregoing, wherein $R^x$ is $C_{1-6}$alkyl. In some embodiments, $R^x$ is methyl.

In some embodiments, provided herein is a compound of Formula (I) or Formula (I-D), or a stereoisomer or tautomer thereof, or a pharmaceutically acceptable salt of any of the foregoing, wherein $R^3$ is

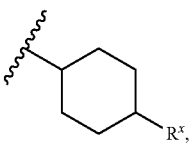

wherein $R^x$ is $C_{1-6}$alkyl or $C_{1-6}$haloalkyl, wherein the compound is of Formula (I-D1):

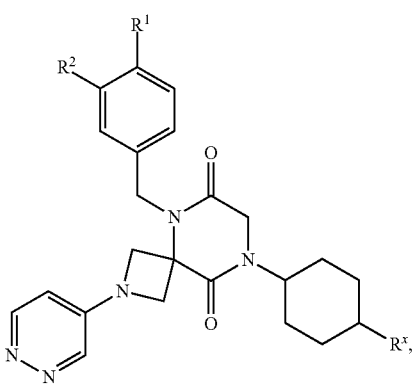

(I-D1)

or a stereoisomer or tautomer thereof, or a pharmaceutically acceptable salt of any of the foregoing. In some embodiments, provided herein is a compound of Formula (I-D1), or a stereoisomer or tautomer thereof, or a pharmaceutically acceptable salt of any of the foregoing, wherein $R^x$ is $C_{1-6}$alkyl. In some embodiments, $R^x$ is methyl.

In some embodiments of the foregoing, $R^3$ is

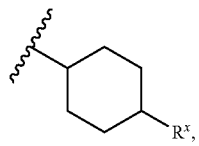

wherein the

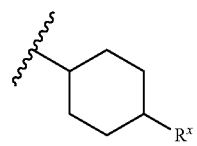

moiety is attached to the remainder of the molecule in the (1r,4r)

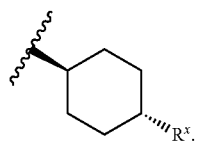

stereochemical configuration. In some embodiments, $R^3$ is $R^x$. In some embodiments, $R^3$ is

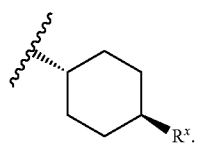

In some embodiments, provided herein is a compound of Formula (I), such as a compound of Formula (I-C), or a stereoisomer or tautomer thereof, or a pharmaceutically acceptable salt of any of the foregoing, wherein $R^3$ is $C_{1-6}$alkyl. In some embodiments, $R^3$ is $C_{1-5}$alkyl. In some embodiments, $R^3$ is $C_{1-4}$alkyl. In some embodiments, $R^3$ is $C_{1-3}$alkyl. In some embodiments, $R^3$ is $C_{3-6}$alkyl. In some embodiments, $R^3$ is $C_{3-5}$alkyl. In some embodiments, $R^3$ is

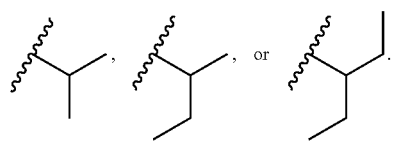

In some embodiments, $R^3$ is

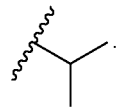

In some embodiments of the foregoing, $R^3$ is $C_{1-6}$alkyl, wherein the $C_{1-6}$alkyl moiety of $R^3$ is attached to the remainder of the molecule in the S stereochemical configuration. In some embodiments, $R^3$ is

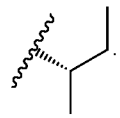

In some embodiments, provided herein is a compound of Formula (I) or Formula (I-C), or a stereoisomer or tautomer thereof, or a pharmaceutically acceptable salt of any of the foregoing, wherein $R^3$ is iso-propyl, wherein the compound is of Formula (I-C2):

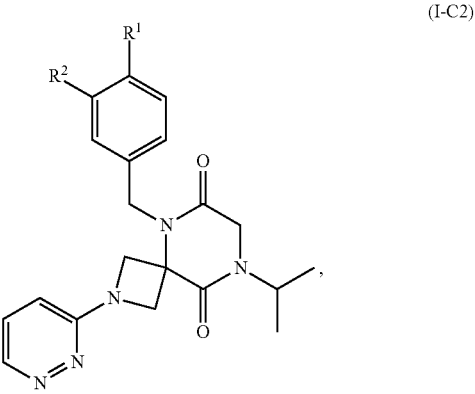

(I-C2)

or a stereoisomer or tautomer thereof, or a pharmaceutically acceptable salt of any of the foregoing. In some embodiments, provided herein is a compound of Formula (I-C2), or a stereoisomer or tautomer thereof, or a pharmaceutically acceptable salt of any of the foregoing, wherein then the total number of halo atoms in $R^1$ and $R^2$ is at least two. In some embodiments, the total number of halo atoms in $R^1$ and $R^2$ is two. In some embodiments, the total number of halo atoms in $R^1$ and $R^2$ is at least three. In some embodiments, the total number of halo atoms in $R^1$ and $R^2$ is at three. In some embodiments, the total number of halo atoms in $R^1$ and $R^2$ is at least four. In some embodiments, the total number of halo atoms in $R^1$ and $R^2$ is four.

In some embodiments, provided herein is a compound of Formula (I), such as a compound of Formula (I-A), (I-A1), (I-B), (I-B1), (I-C), (I-C1), (I-C2), (I-D), or (I-D1), or a stereoisomer or tautomer thereof, or a pharmaceutically acceptable salt of any of the foregoing, wherein $R^1$ is halo. In some embodiments, $R^1$ is fluoro or chloro. In some embodiments, $R^1$ is fluoro. In other embodiments, $R^1$ is chloro.

In some embodiments, provided herein is a compound of Formula (I), such as a compound of Formula (I-A), (I-A1), (I-B), (I-B1), (I-C), (I-C1), (I-C2), (I-D), or (I-D1), or a stereoisomer or tautomer thereof, or a pharmaceutically acceptable salt of any of the foregoing, wherein $R^1$ is $C_{1-6}$haloalkyl. In some embodiments, $R^1$ is $C_{1-6}$haloalkyl. In some embodiments, $R^1$ is $C_{1-2}$haloalkyl. In some embodiments, $R^1$ is —$CF_3$.

In some embodiments, provided herein is a compound of Formula (I), such as a compound of Formula (I-A), (I-A1), (I-B), (I-B1), (I-C), (I-C1), (I-C2), (I-D), or (I-D1), or a stereoisomer or tautomer thereof, or a pharmaceutically acceptable salt of any of the foregoing, wherein $R^2$ is H.

In some embodiments, provided herein is a compound of Formula (I), such as a compound of Formula (I-A), (I-A1), (I-B), (I-B1), (I-C), (I-C1), (I-C2), (I-D), or (I-D1), or a stereoisomer or tautomer thereof, or a pharmaceutically acceptable salt of any of the foregoing, wherein $R^2$ is halo. In some embodiments, $R^2$ is fluoro or chloro. In some embodiments, $R^2$ is fluoro. In other embodiments, $R^2$ is chloro.

In some embodiments, provided herein is a compound of Formula (I), such as a compound of Formula (I-A), (I-A1), (I-B), (I-B1), (I-C), (I-C1), (I-C2), (I-D), or (I-D1), or a stereoisomer or tautomer thereof, or a pharmaceutically acceptable salt of any of the foregoing, wherein $R^2$ is $C_{1-6}$alkyl. In some embodiments, $R^2$ is $C_{1-3}$alkyl. In some embodiments, $R^2$ is $C_{1-3}$ alkyl. In some embodiments, $R^2$ is $C_{1-2}$alkyl. In some embodiments, $R^2$ is methyl.

In some embodiments, provided herein is a compound of Formula (I), such as a compound of Formula (I-A), (I-A1), (I-B), (I-B1), (I-C), (I-C1), (I-C2), (I-D), or (I-D1), or a stereoisomer or tautomer thereof, or a pharmaceutically acceptable salt of any of the foregoing, wherein $R^1$ is halo or $C_{1-6}$haloalkyl and $R^2$ is H. In some embodiments, $R^1$ is halo or $C_{1-6}$haloalkyl and $R^2$ is halo. In some embodiments, $R^1$ is halo or $C_{1-6}$haloalkyl and $R^2$ is chloro or fluoro. In some embodiments, $R^1$ is halo or $C_{1-6}$haloalkyl and $R^2$ is $C_{1-6}$alkyl. In some embodiments, $R^1$ is halo or $C_{1-6}$haloalkyl and $R^2$ is methyl.

In some embodiments, provided herein is a compound of Formula (I), such as a compound of Formula (I-A), (I-A1), (I-B), (I-B1), (I-C), (I-C1), (I-C2), (I-D), or (I-D1), or a stereoisomer or tautomer thereof, or a pharmaceutically acceptable salt of any of the foregoing, wherein $R^1$ is halo and $R^2$ is H. In some embodiments, $R^1$ is fluoro or chloro and $R^2$ is H. In some embodiments, $R^1$ is fluoro and $R^2$ is H. In some embodiments, $R^1$ is chloro and $R^2$ is H. In some embodiments, $R^1$ is $C_{1-6}$haloalkyl and $R^2$ is H. In some embodiments, $R^1$ is —$CF_3$ and $R^2$ is H.

In some embodiments, $R^1$ is halo and $R^2$ is halo. In some embodiments, $R^1$ is fluoro or chloro and $R^2$ is halo. In some embodiments, $R^1$ is fluoro or chloro and $R^2$ is fluoro or chloro. In some embodiments, $R^1$ is fluoro and $R^2$ is fluoro. In some embodiments, $R^1$ is chloro and $R^2$ is chloro. In some embodiments, $R^1$ is fluoro and $R^2$ is chloro. In some embodiments, $R^1$ is chloro and $R^2$ is fluoro. In some embodiments, $R^1$ is $C_{1-6}$haloalkyl and $R^2$ is halo. In some embodiments, $R^1$ is —$CF_3$ and $R^2$ is halo.

In some embodiments, $R^1$ is halo and $R^2$ is $C_{1-6}$alkyl. In some embodiments, $R^1$ is fluoro or chloro and $R^2$ is $C_{1-6}$alkyl. In some embodiments, $R^1$ is fluoro or chloro and $R^2$ is methyl. In some embodiments, $R^1$ is fluoro and $R^2$ is methyl. In some embodiments, $R^1$ is chloro and $R^2$ is methyl. In some embodiments, $R^1$ is $C_{1-6}$haloalkyl and $R^2$ is $C_{1-6}$alkyl. In some embodiments, $R^1$ is —$CF_3$ and $R^2$ is $C_{1-6}$alkyl.

In some embodiments, provided herein are compounds and salts thereof described in Table 1.

TABLE 1

| Compound No. | Structure | Name |
|---|---|---|
| 1 | 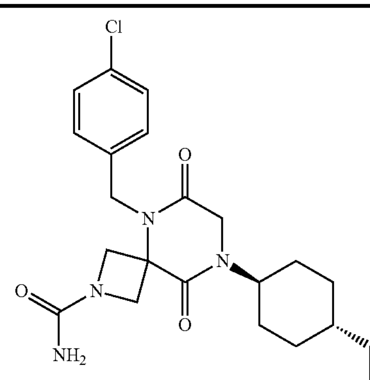 | 5-(4-chlorobenzyl)-8-((1r,4r)-4-ethylcyclohexyl)-6,9-dioxo-2,5,8-triazaspiro[3.5]nonane-2-carboxamide |
| 2 | 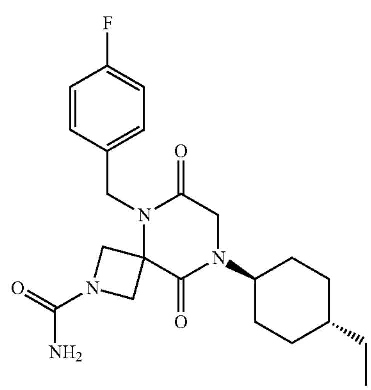 [SMILES: CC[C@H]1CC[C@H](N2CC(=O)N(Cc3ccc(F)cc3)C3(CN(C(N)=O)C3)C2=O)CC1] | 8-((1r,4r)-4-ethylcyclohexyl)-5-(4-fluorobenzyl)-6,9-dioxo-2,5,8-triazaspiro[3.5]nonane-2-carboxamide |

TABLE 1-continued

| Compound No. | Structure | Name |
|---|---|---|
| 3 | 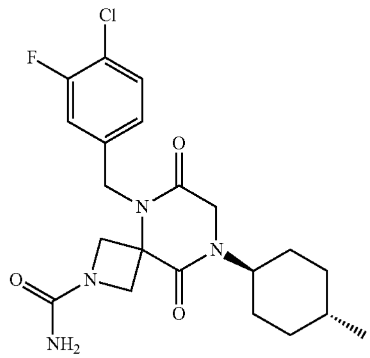 [SMILES: C[C@H]1CC[C@H](N2CC(=O)N(Cc3ccc(Cl)c(F)c3)C3(CN(C(N)=O)C3)C2=O)CC1] | 5-(4-chloro-3-fluorobenzyl)-8-((1r,4r)-4-methylcyclohexyl)-6,9-dioxo-2,5,8-triazaspiro[3.5]nonane-2-carboxamide |
| 4 | 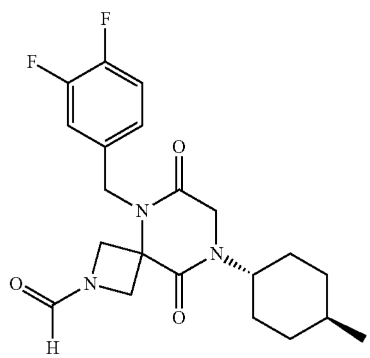 [SMILES: C[C@H]1CC[C@H](N2CC(=O)N(Cc3ccc(F)c(F)c3)C3(CN(C=O)C3)C2=O)CC1] | 5-(3,4-difluorobenzyl)-8-((1r,4r)-4-methylcyclohexyl)-6,9-dioxo-2,5,8-triazaspiro[3.5]nonane-2-carbaldehyde |
| 5 | 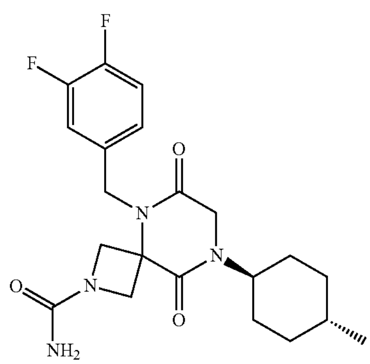 | 5-(3,4-difluorobenzyl)-8-((1r,4r)-4-methylcyclohexyl)-6,9-dioxo-2,5,8-triazaspiro[3.5]nonane-2-carboxamide |
| 6 | 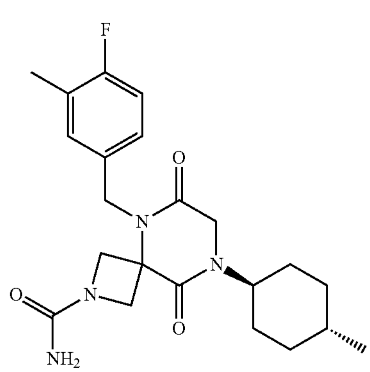 | 5-(4-fluoro-3-methylbenzyl)-8-((1r,4r)-4-methylcyclohexyl)-6,9-dioxo-2,5,8-triazaspiro[3.5]nonane-2-carboxamide |

TABLE 1-continued

| Compound No. | Structure | Name |
|---|---|---|
| 7 | 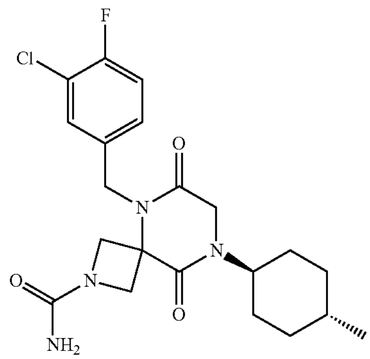 | 5-(3-chloro-4-fluorobenzyl)-8-((1r,4r)-4-methylcyclohexyl)-6,9-dioxo-2,5,8-triazaspiro[3.5]nonane-2-carboxamide |
| 8 | 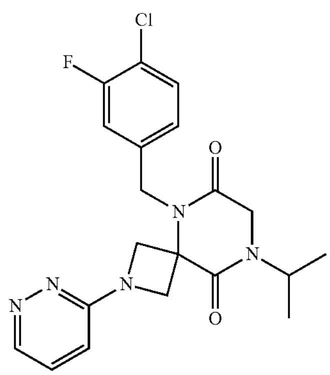 [SMILES: CC(C)N1CC(=O)N(Cc2ccc(Cl)c(F)c2)C2(CN(c3cccnn3)C2)C1=O] | 5-(4-chloro-3-fluorobenzyl)-8-isopropyl-2-(pyridazin-3-yl)-2,5,8-triazaspiro[3.5]nonane-6,9-dione |
| 9 | 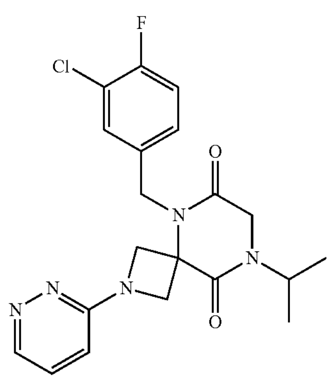 [SMILES: CC(C)N1CC(=O)N(Cc2ccc(F)c(Cl)c2)C2(CN(c3cccnn3)C2)C1=O] | 5-(3-chloro-4-fluorobenzyl)-8-isopropyl-2-(pyridazin-3-yl)-2,5,8-triazaspiro[3.5]nonane-6,9-dione |
| 10 | 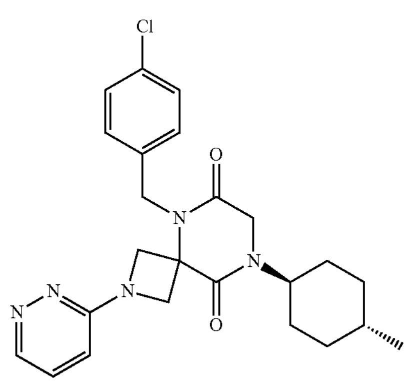 [SMILES: C[C@H]1CC[C@H](N2CC(=O)N(Cc3ccc(Cl)cc3)C3(CN(c4cccnn4)C3)C2=O)CC1] | 5-(4-chlorobenzyl)-8-((1r,4r)-4-methylcyclohexyl)-2-(pyridazin-3-yl)-2,5,8-triazaspiro[3.5]nonane-6,9-dione |

TABLE 1-continued

| Compound No. | Structure | Name |
|---|---|---|
| 11 | 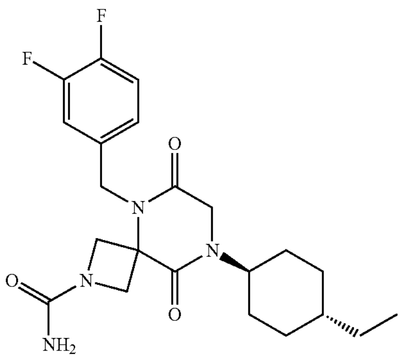 [SMILES: CC[C@H]1CC[C@H](N2CC(=O)N(Cc3ccc(F)c(F)c3)C3(CN(C(N)=O)C3)C2=O)CC1] | 5-(3,4-difluorobenzyl)-8-((1r,4r)-4-ethylcyclohexyl)-6,9-dioxo-2,5,8-triazaspiro[3.5]nonane-2-carboxamide |
| 12 | 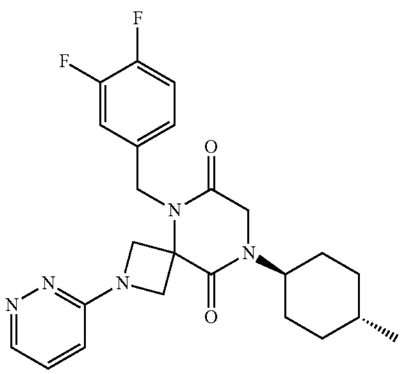 [SMILES: C[C@H]1CC[C@H](N2CC(=O)N(Cc3ccc(F)c(F)c3)C3(CN(c4cccnn4)C3)C2=O)CC1] | 5-(3,4-difluorobenzyl)-8-((1r,4r)-4-methylcyclohexyl)-2-(pyridazin-3-yl)-2,5,8-triazaspiro[3.5]nonane-6,9-dione |
| 13 | 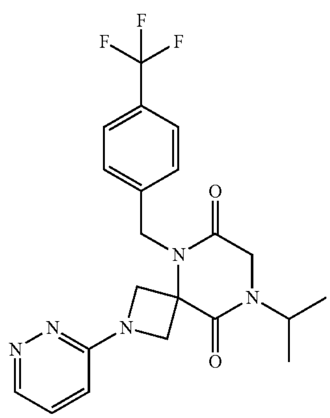 [SMILES: CC(C)N1CC(=O)N(Cc2ccc(C(F)(F)F)cc2)C2(CN(c3cccnn3)C2)C1=O] | 8-isopropyl-2-(pyridazin-3-yl)-5-(4-(trifluoromethyl)benzyl)-2,5,8-triazaspiro[3.5]nonane-6,9-dione |
| 14 | 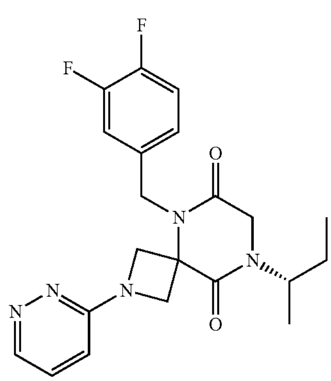 [SMILES: CC[C@H](C)N1CC(=O)N(Cc2ccc(F)c(F)c2)C2(CN(c3cccnn3)C2)C1=O] | (S)-8-(sec-butyl)-5-(3,4-difluorobenzyl)-2-(pyridazin-3-yl)-2,5,8-triazaspiro[3.5]nonane-6,9-dione |

TABLE 1-continued

| Compound No. | Structure | Name |
|---|---|---|
| 15 | 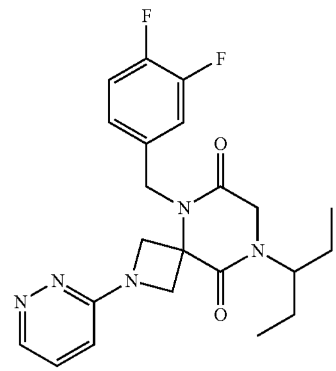 [SMILES: CCC(CC)N1CC(=O)N(Cc2ccc(F)c(F)c2)C2(CN(c3cccnn3)C2)C1=O] | 5-(3,4-difluorobenzyl)-8-(pentan-3-yl)-2-(pyridazin-3-triazaspiro[3.5]nonane-6,9-dione |
| 16 | 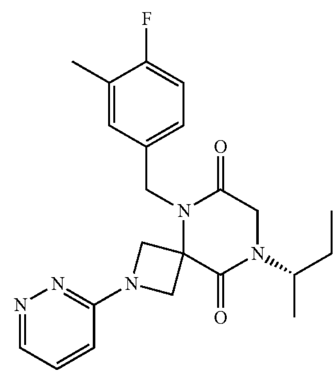 [SMILES: CC[C@H](C)N1CC(=O)N(Cc2ccc(F)c(C)c2)C2(CN(c3cccnn3)C2)C1=O] | (S)-8-(sec-butyl)-5-(4-fluoro-3-methylbenzyl)-2-(pyridazin-3-yl)-2,5,8-triazaspiro[3.5]nonane-6,9-dione |
| 17 | 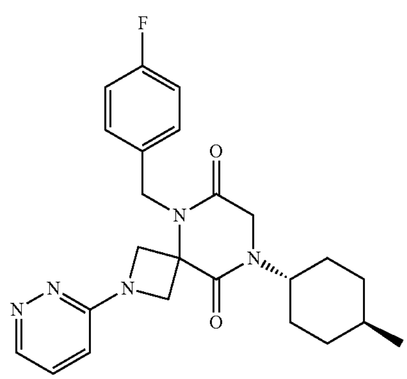 [SMILES: C[C@H]1CC[C@H](N2CC(=O)N(Cc3ccc(F)cc3)C3(CN(c4cccnn4)C3)C2=O)CC1] | 5-(4-fluorobenzyl)-8-((1r,4r)-4-methylcyclohexyl)-2-(pyridazin-3-yl)-2,5,8-triazaspiro[3.5]nonane-6,9-dione |
| 18 | 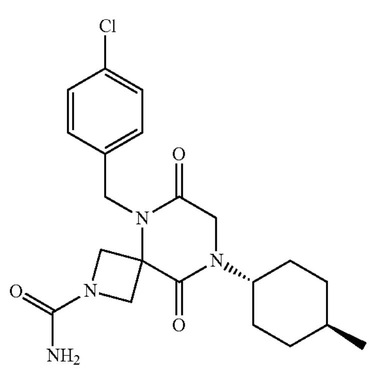 [SMILES: C[C@H]1CC[C@H](N2CC(=O)N(Cc3ccc(Cl)cc3)C3(CN(C(N)=O)C3)C2=O)CC1] | 5-(4-chlorobenzyl)-8-((1r,4r)-4-methylcyclohexyl)-6,9-dioxo-2,5,8-triazaspiro[3.5]nonane-2-carboxamide |

TABLE 1-continued

| Compound No. | Structure | Name |
|---|---|---|
| 19 | 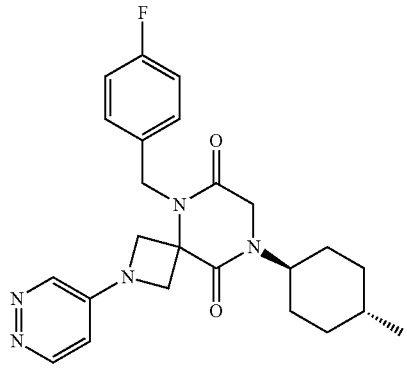 [SMILES: C[C@H]1CC[C@H](N2CC(=O)N(Cc3ccc(F)cc3)C3(CN(c4ccnnc4)C3)C2=O)CC1] | 5-(4-fluorobenzyl)-8-((1r,4r)-4-methylcyclohexyl)-2-(pyridazin-4-yl)-2,5,8-triazaspiro[3.5]nonane-6,9-dione |
| 20 | 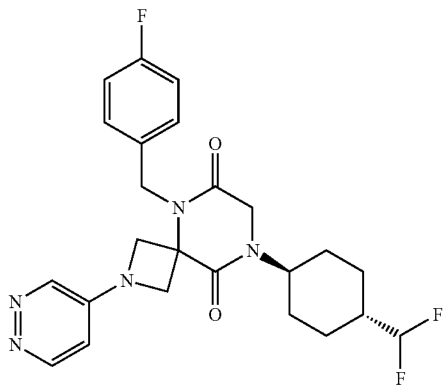 [SMILES: O=C1CN([C@H]2CC[C@H](C(F)F)CC2)C(=O)C2(CN(c3ccnnc3)C2)N1Cc1ccc(F)cc1] | 8-((1r,4r)-4-(difluoromethyl)cyclohexyl)-5-(4-fluorobenzyl)-2-(pyridazin-4-yl)-2,5,8-triazaspiro[3.5]nonane-6,9-dione |

In some embodiments, provided herein is a compound of Formula (I), or a stereoisomer or tautomer thereof, or a pharmaceutically acceptable salt of any of the foregoing, wherein the compound is selected from the group consisting of 5-(4-chlorobenzyl)-8-(4-ethylcyclohexyl)-6,9-dioxo-2,5,8-triazaspiro[3.5]nonane-2-carboxamide;
8-(4-ethylcyclohexyl)-5-(4-fluorobenzyl)-6,9-dioxo-2,5,8-triazaspiro[3.5]nonane-2-carboxamide;
5-(4-chloro-3-fluorobenzyl)-8-(4-methylcyclohexyl)-6,9-dioxo-2,5,8-triazaspiro[3.5]nonane-2-carboxamide;
5-(3,4-difluorobenzyl)-8-(4-methylcyclohexyl)-6,9-dioxo-2,5,8-triazaspiro[3.5]nonane-2-carbaldehyde;
5-(3,4-difluorobenzyl)-8-(4-methylcyclohexyl)-6,9-dioxo-2,5,8-triazaspiro[3.5]nonane-2-carboxamide;
5-(4-fluoro-3-methylbenzyl)-8-(4-methylcyclohexyl)-6,9-dioxo-2,5,8-triazaspiro[3.5]nonane-2-carboxamide;
5-(3-chloro-4-fluorobenzyl)-8-(4-methylcyclohexyl)-6,9-dioxo-2,5,8-triazaspiro[3.5]nonane-2-carboxamide;
5-(4-chloro-3-fluorobenzyl)-8-isopropyl-2-(pyridazin-3-yl)-2,5,8-triazaspiro[3.5]nonane-6,9-dione;
5-(3-chloro-4-fluorobenzyl)-8-isopropyl-2-(pyridazin-3-yl)-2,5,8-triazaspiro[3.5]nonane-6,9-dione;
5-(4-chlorobenzyl)-8-(4-methylcyclohexyl)-2-(pyridazin-3-yl)-2,5,8-triazaspiro[3.5]nonane-6,9-dione;
5-(3,4-difluorobenzyl)-8-(4-ethylcyclohexyl)-6,9-dioxo-2,5,8-triazaspiro[3.5]nonane-2-carboxamide;
5-(3,4-difluorobenzyl)-8-(4-methylcyclohexyl)-2-(pyridazin-3-yl)-2,5,8-triazaspiro[3.5]nonane-6,9-dione;
8-isopropyl-2-(pyridazin-3-yl)-5-(4-(trifluoromethyl)benzyl)-2,5,8-triazaspiro[3.5]nonane-6,9-dione;
8-(sec-butyl)-5-(3,4-difluorobenzyl)-2-(pyridazin-3-yl)-2,5,8-triazaspiro[3.5]nonane-6,9-dione;
5-(3,4-difluorobenzyl)-8-(pentan-3-yl)-2-(pyridazin-3-yl)-2,5,8-triazaspiro[3.5]nonane-6,9-dione;
8-(sec-butyl)-5-(4-fluoro-3-methylbenzyl)-2-(pyridazin-3-yl)-2,5,8-triazaspiro[3.5]nonane-6,9-dione;
5-(4-fluorobenzyl)-8-(4-methylcyclohexyl)-2-(pyridazin-3-yl)-2,5,8-triazaspiro[3.5]nonane-6,9-dione;
5-(4-chlorobenzyl)-8-(4-methylcyclohexyl)-6,9-dioxo-2,5,8-triazaspiro[3.5]nonane-2-carboxamide;
5-(4-fluorobenzyl)-8-(4-methylcyclohexyl)-2-(pyridazin-4-yl)-2,5,8-triazaspiro[3.5]nonane-6,9-dione; and
8-(4-(difluoromethyl)cyclohexyl)-5-(4-fluorobenzyl)-2-(pyridazin-4-yl)-2,5,8-triazaspiro[3.5]nonane-6,9-dione,
or a stereoisomer or tautomer thereof, or a pharmaceutically acceptable salt of any of the foregoing.

In some variations, any of the compounds described herein, such as a compound of Formula (I), (I-A), (I-A1), (I-B), (I-B1), (I-C), (I-C1), (I-C2), (I-D), or (I-D1), or any variation thereof, or a compound of Table 1 may be deuterated (i.e., one or more hydrogen atoms are replaced by one or more deuterium atoms). In some of these variations, the compound is deuterated at a single site. In other variations, the compound is deuterated at multiple sites. Deuterated compounds can be prepared from deuterated starting materials in a manner similar to the preparation of the corresponding non-deuterated compounds. Hydrogen atoms may also be replaced with deuterium atoms using other method known in the art.

Any formula given herein, such as Formula (I), (I-A), (I-A1), (I-B), (I-B1), (I-C), (I-C$_1$), (I-C2), (I-D), or (I-D1), is intended to represent compounds having structures depicted by the structural formula as well as certain variations or forms. In particular, compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Where a compound of Table 1 is depicted with a particular stereochemical configuration, also provided herein is any alternative stereochemical configuration of the compound, as well as a mixture of stereoisomers of the compound in any ratio. For example, where a compound of Table 1 has a stereocenter that is in an "S" stereochemical configuration, also provided herein is enantiomer of the compound wherein that stereocenter is in an "R" stereochemical configuration. Likewise, when a compound of Table 1 has a stereocenter that is in an "R" configuration, also provided herein is enantiomer of the compound in an "S" stereochemical configuration. Also provided are mixtures of the compound with both the "S" and the "R" stereochemical configuration. Additionally, if a compound of Table 1 has two or more stereocenters, also provided are any enantiomer or diastereomer of the compound. For example, if a compound of Table 1 contains a first stereocenter and a second stereocenter with "R" and "R" stereochemical configurations, respectively, also provided are stereoisomers of the compound having first and second stereocenters with "S" and "S" stereochemical configurations, respectively, "S" and "R" stereochemical configurations, respectively, and "R" and "S" stereochemical configurations, respectively. If a compound of Table 1 contains a first stereocenter and a second stereocenter with "S" and "S" stereochemical configurations, respectively, also provided are stereoisomers of the compound having first and second stereocenters with "R" and "R" stereochemical configurations, respectively, "S" and "R" stereochemical configurations, respectively, and "R" and "S" stereochemical configurations, respectively. If a compound of Table 1 contains a first stereocenter and a second stereocenter with "S" and "R" stereochemical configurations, respectively, also provided are stereoisomers of the compound having first and second stereocenters with "R" and "S" stereochemical configurations, respectively, "R" and "R" stereochemical configurations, respectively, and "S" and "S" stereochemical configurations, respectively. Similarly, if a compound of Table 1 contains a first stereocenter and a second stereocenter with "R" and "S" stereochemical configurations, respectively, also provided are stereoisomers of the compound having first and second stereocenters with "S" and "R" stereochemical configurations, respectively, "R" and "R" stereochemical configurations, respectively, and "S" and "S" stereochemical configurations, respectively. Furthermore, certain structures may exist as geometric isomers (i.e., cis and trans isomers), as tautomers, or as atropisomers. Additionally, any formula given herein is intended to refer also to any one of hydrates, solvates, and amorphous and polymorphic forms of such compounds, and mixtures thereof, even if such forms are not listed explicitly. In some embodiments, the solvent is water and the solvates are hydrates.

Representative examples of compounds detailed herein, including intermediates and final compounds, are depicted in the tables and elsewhere herein. It is understood that in one aspect, any of the compounds may be used in the methods detailed herein, including, where applicable, intermediate compounds that may be isolated and administered to an individual or subject.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

In one variation, the compounds herein are synthetic compounds prepared for administration to an individual or subject. In another variation, compositions are provided containing a compound in substantially pure form. In another variation, provided are pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Any variation or embodiment of $R^1$, $R^2$, $R^3$, and $R^4$ provided herein can be combined with every other variation or embodiment of $R^1$, $R^2$, $R^3$, and $R^4$, the same as if each combination had been individually and specifically described.

As used herein, when any variable occurs more than one time in a chemical formula, its definition on each occurrence is independent of its definition at every other occurrence.

Formula (I) includes all subformulae thereof. For example, Formula (I) includes compounds of Formula (I-A), (I-A1), (I-B), (I-B1), (I-C), (I-C1), (I-C2), (I-D), or (I-D1).

Certain compound names provided herein, including in Table 1, are provided by ChemBioDraw Professional 15.0.0.106. One of skilled in the art would understand that the compounds may be named or identified using various commonly recognized nomenclature systems and symbols. By way of example, the compounds may be named or identified with common names, systematic or non-systematic names. The nomenclature systems and symbols that are commonly recognized in the art of chemistry include, for example, Chemical Abstract Service (CAS), ChemBioDraw Ultra, and International Union of Pure and Applied Chemistry (IUPAC).

In some embodiments, the compounds of the disclosure, or a pharmaceutically acceptable salt thereof, may have advantages related to one or more of the following: hERG profile, toxicity profile, safety window, selectivity, off-target profile, favorable drug/drug interaction profile, PK parameters including bioavailability, clearance and half life, mechanism of action, CYP inhibition and time dependent inhibition profile, permeability and/or efflux, solubility, metabolism, unbound fraction, adequate human dose, and ease of synthesis on a large scale.

Compositions

Also provided are compositions, such as pharmaceutical compositions, that include a compound disclosed and/or described herein and one or more additional medicinal agents, pharmaceutical agents, adjuvants, carriers, excipients, and the like. Suitable medicinal and pharmaceutical agents include those described herein. In some embodiments, the pharmaceutical composition includes a pharmaceutically acceptable excipient or adjuvant and at least one chemical entity as described herein. Examples of pharmaceutically acceptable excipients include, but are not limited to, mannitol, lactose, starch, magnesium stearate, sodium saccharine, talcum, cellulose, sodium crosscarmellose, glucose, gelatin, sucrose, and magnesium carbonate. In some embodiments, provided are compositions, such as pharmaceutical compositions that contain one or more compounds described herein, or stereoisomer or tautomer thereof, or a pharmaceutically acceptable salt of any of the foregoing.

In some embodiments, provided is a pharmaceutically acceptable composition comprising a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing. In some aspects, a composition may contain a synthetic intermediate that may be used in the preparation of a compound described herein. The compositions described herein may contain any other suitable active or inactive agents.

Any of the compositions described herein may be sterile or contain components that are sterile. Sterilization can be achieved by methods known in the art. Any of the compositions described herein may contain one or more compounds or conjugates that are substantially pure.

Also provided are packaged pharmaceutical compositions, comprising a pharmaceutical composition as described herein and instructions for using the composition to treat a patient suffering from a disease or condition described herein.

Methods of Use

The compounds and pharmaceutical compositions herein may be used to treat or prevent a disease or condition in an individual or subject.

When used in a prophylactic manner, the compounds disclosed and/or described herein may prevent a disease or disorder from developing or lessen the extent of a disease or disorder that may develop in an individual or subject at risk of developing the disease or disorder.

Without being bound by theory, the compounds and pharmaceutical compositions disclosed herein are believed to act by inhibiting myosin. This inhibition potentially decreases the number of independent myosin heads interacting with actin filaments reducing the amount of contraction. Reducing contraction of cardiac muscle can be important for the treatment of heart diseases in which over-contraction is an issue. In some embodiments, provided are methods of treating or preventing heart disease in an individual or subject, comprising administering to the individual or subject in need thereof a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing. In some embodiments, provided are methods of treating or preventing heart disease in a subject in need thereof comprising administering to the subject a therapeutically effective amount of at least one chemical entity as described herein. In some embodiments, provided are methods of treating heart disease in a subject in need thereof comprising administering to the subject a therapeutically effective amount of at least one chemical entity as described herein. In some embodiments, provided are methods of treating an established or diagnosed heart disease in a subject in need thereof comprising administering to the subject a therapeutically effective amount of at least one chemical entity as described herein. In some embodiments, provided are methods of preventing heart disease in a subject in need thereof comprising administering to the subject a therapeutically effective amount of at least one chemical entity as described herein.

Also provided herein is the use of a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, in the manufacture of a medicament for treatment of a heart disease in a subject. In some aspects, provided is a compound or composition as described herein for use in a method of treatment of the human or animal body by therapy. In some embodiments, provided herein are compounds of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, for use in a method of treatment of the human or animal body by therapy. In some embodiments, provided herein are compounds of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, for use in treating or preventing heart disease. In some embodiments, provided herein are compounds of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, for use in treating heart disease. In some embodiments, provided herein are compounds of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, for use in treating an established or diagnosed heart disease. In other embodiments, provided herein are compounds of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, for use in preventing heart disease. In some embodiments, provided herein are compounds of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, for use in treating a disease or condition associated with HCM. In some embodiments, provided herein are compounds of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, for use in treating a disease or condition associated with secondary left ventricular wall thickening. In some embodiments, provided herein are compounds of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, for use in ameliorating a symptom associated with heart disease. In other embodiments, provided herein are compounds of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, for use in reducing the risk of a symptom associated with heart disease. In other embodiments, provided herein are compounds of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, for use in treating a disease or condition associated with small left ventricular cavity, cavity obliteration, hyperdynamic left ventricular contraction, obstruction of blood flow out of the left ventricle, cardiac hypertrophy, small cardiac stroke volume, impaired relaxation of the left ventricle, high left ventricle filling pressure, myocardial ischemia, or cardiac fibrosis. In certain embodiments, provided herein are compounds of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, for use in treating a disease or condition associated with small left ventricular cavity and cavity obliteration, hyperdynamic left ventricular contraction, myocardial ischemia, or cardiac fibrosis. In some embodiments, provided herein are compounds of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, for use in treating muscular dystrophies. In some embodiments, provided herein are compounds of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, for use in treating a glycogen storage disease. In other embodiments, provided herein are compounds of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, for use in modulating the cardiac sarcomere, such as inhibiting the cardiac sarcomere. In yet other embodiments, provided herein are compounds of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, for use in potentiating cardiac myosin.

In some embodiments, the subject is a mammal. In some embodiments, the subject is a mouse, rat, dog, cat, pig, sheep, horse, cow, or human. In some embodiments, the subject is a human. In some embodiments, the subject has an established or diagnosed heart disease. In some embodiments, the subject has established or diagnosed hypertrophic cardiomyopathy (HCM). In some embodiments, the subject is at risk for developing heart disease. In some embodiments, the subject has a mutation that increases risk for heart disease. In some embodiments, the subject has a mutation that increases risk for hypertrophic cardiomyopathy (HCM). In some embodiments, the mutation is a sarcomeric mutation. In some embodiments, the mutation is a mutation in myosin heavy chain R (MHC-0), cardiac muscle troponin T (cTnT), tropomyosin alpha-1 chain (TPM1), myosin-binding protein C cardiac-type (MYBPC3), cardiac troponin I (cTnI), myosin essential light chain (ELC), titin (TTN), myosin regulatory light chain 2 ventricular/cardiac muscle isoform (MLC-2), cardiac muscle alpha actin, muscle LIM protein (MLP), or protein kinase AMP-activated non-catalytic subunit gamma 2 (PRKAG2). In some embodiments, the mutation is a mutation in MHC-β. In some embodiments, the subject has established or diagnosed hypertrophic cardiomyopathy without a confirmed genetic etiology.

In some embodiments, the subject has a high risk of progressive symptoms. In some embodiments, the subject has a high risk of atrial fibrillation, ventricular tachyarrhythmias, stroke, and/or sudden death. In some embodiments, the subject has a reduced exercise capacity. In some embodiments, the reduced exercise capacity is as compared to an age-matched control population. In some embodiments, the subject is eligible for surgical intervention or percutaneous ablation to treat the heart disease.

In some embodiments, the heart disease is hypertrophic cardiomyopathy (HCM). In some embodiments, the heart disease is obstructive HCM. In some embodiments, the heart disease is nonobstructive HCM. In some embodiments, the HCM is associated with a sarcomeric mutation. In some embodiments, the HCM is associated with a non-sarcomeric mutation. In some embodiments, the heart disease is obstructive or nonobstructive HCM caused by sarcomeric and/or non-sarcomeric mutations. In some embodiments, the sarcomeric mutation is a mutation in a myosin heavy chain β (MHC-β), cardiac muscle troponin T (cTnT), tropomyosin alpha-1 chain (TPM1), myosin-binding protein C cardiac-type (MYBPC3), cardiac troponin I (cTnI), myosin essential light chain (ELC), titin (TTN), myosin regulatory light chain 2 ventricular/cardiac muscle isoform (MLC-2), cardiac muscle alpha actin, or muscle LIM protein (MLP). In some embodiments, the sarcomeric mutation is a mutation in MHC-β. In some embodiments, the non-sarcomeric mutation is a mutation in protein kinase AMP-activated non-catalytic subunit gamma 2 (PRKAG2).

In some embodiments, provided herein are methods of treating a disease or condition associated with HCM, comprising administering to the individual or subject in need thereof a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing. In some embodiments, the disease or condition is Fabry's Disease, Danon Disease, mitochondrial cardiomyopathies, or Noonan Syndrome.

Also provided herein is the use of a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, in the manufacture of a medicament for treatment of a disease or condition associated with HCM.

In some embodiments, the heart disease is heart failure with preserved ejection fraction (HFpEF). In some embodiments, the heart disease is diastolic dysfunction. In some embodiments, the heart disease is cardiomyopathy. In some embodiments, the heart disease is primary or secondary restrictive cardiomyopathy. In some embodiments, the heart disease is condition or symptoms caused by coronary artery disease. In some embodiments, the heart disease is myocardial infarction or angina pectoris. In some embodiments, the heart disease is left ventricular outflow tract obstruction. In some embodiments, the heart disease is hypertensive heart disease. In some embodiments, the heart disease is congenital heart disease. In some embodiments, the heart disease is cardiac ischemia and/or coronary heart disease. In some embodiments, the heart disease is diabetic heart disease. In other embodiments, the heart disease is congestive heart failure. In some embodiments, the heart disease is right heart failure. In other embodiments, the heart disease is cardiorenal syndrome. In some embodiments, the heart disease is infiltrative cardiomyopathy. In some embodiments, the heart disease is a condition that is or is related to cardiac senescence or diastolic dysfunction due to aging. In some embodiments, the heart disease is a condition that is or is related to left ventricular hypertrophy and/or concentric left ventricular remodeling.

In some embodiments, the provided are methods of treating a disease or condition associated with secondary left ventricular wall thickening in an individual or subject, comprising administering to the individual or subject in need thereof a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing. In some embodiments, the disease is hypertension, valvular heart diseases (aortic stenosis, Mitral valve regurgitation), metabolic syndromes (diabetes, obesity), end stage renal disease, scleroderma, sleep apnea, amyloidosis, Fabry's disease, Friedreich Ataxia, Danon disease, Noonan syndrome, or Pompe disease.

Also provided herein is the use of a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, in the manufacture of a medicament for treatment of a disease or condition associated with secondary left ventricular wall thickening.

In some embodiments, provided are methods of ameliorating a symptom associated with heart disease in a subject, comprising administering to the individual or subject in need thereof a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, wherein the symptom is one or more selected from poor or reduced cardiac elasticity, poor or reduced diastolic left ventricular relaxation, abnormal left atrial pressure (e.g., abnormally high left atrial pressure), paroxysmal or permanent atrial fibrillation, increased left atrial and pulmonary capillary wedge pressures, increased left ventricular diastolic pressures, syncope, ventricular relaxation during diastole, ventricular fibrosis, left ventricular hypertrophy, left ventricular mass, increased left ventricular wall thickness, left ventricular mid-cavity obstruction, increased systolic anterior motion of mitral valve, left ventricular outflow tract obstruction, chest pain, exertional dyspnea, pre-syncope, abnormal exercise capacity, and fatigue.

In some embodiments, the provided are methods of reducing the risk of a symptom associated with heart disease in a subject, comprising administering to the individual or subject in need thereof a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, wherein the symptom is one or more selected from sudden cardiac death, poor or reduced cardiac elasticity, poor or reduced diastolic left ventricular relaxation, abnormal left atrial pressure (e.g., abnormally high left atrial pressure), paroxysmal or permanent atrial fibrillation, increased left atrial and pulmonary capillary wedge pressures, increased left ventricular diastolic pressures, syncope, ventricular relaxation during diastole, ventricular fibrosis, left ventricular hypertrophy, left ventricular mass, increased left ventricular wall thickness, left ventricular mid-cavity obstruction, increased systolic anterior motion of mitral valve, left ventricular outflow tract obstruction, chest pain, exertional dyspnea, pre-syncope, abnormal exercise capacity, and fatigue.

In some embodiments, the provided are methods of treating a disease or condition associated with small left ventricular cavity, cavity obliteration, hyperdynamic left ventricular contraction, obstruction of blood flow out of the left ventricle, cardiac hypertrophy, small cardiac stroke volume, impaired relaxation of the left ventricle, high left ventricle filling pressure, myocardial ischemia, or cardiac fibrosis in an individual or subject, comprising administering to the individual or subject in need thereof a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing.

In some embodiments, provided are methods of treating a disease or condition associated with small left ventricular cavity and cavity obliteration, hyperdynamic left ventricular contraction, myocardial ischemia, or cardiac fibrosis in an individual or subject, comprising administering to the individual or subject in need thereof a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing.

Also provided herein is the use of a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, in the manufacture of a medicament for treatment of a disease or condition associated with small left ventricular cavity and cavity obliteration, hyperdynamic left ventricular contraction, myocardial ischemia, or cardiac fibrosis.

In some embodiments, the provided are methods of treating muscular dystrophies in an individual or subject (e.g., Duchenne muscular dystrophy), comprising administering to the individual or subject in need thereof a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing. Also provided herein is the use of a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, in the manufacture of a medicament for treatment of muscular dystrophies (e.g., Duchenne muscular dystrophy).

In some embodiments, the provided are methods of treating a glycogen storage disease in an individual or subject, comprising administering to the individual or subject in need thereof a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing. Also provided herein is the use of a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, in the manufacture of a medicament for treatment of a glycogen storage disease.

Also provided are methods for modulating the cardiac sarcomere in an individual or subject which method comprises administering to an individual or subject in need thereof a therapeutically effective amount of at least one chemical entity as described herein. In some embodiments, provided are methods of inhibiting the cardiac sarcomere, comprising contacting the cardiac sarcomere with at least one chemical entity as described herein, such as a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing. Additionally provided herein is the use of at least one chemical entity as described herein, such as a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, in the manufacture of a medicament for inhibiting the cardiac sarcomere of an individual or subject.

Also provided are methods for potentiating cardiac myosin in an individual or subject which method comprises administering to an individual or subject in need thereof a therapeutically effective amount of at least one chemical entity as described herein such as a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing. Additionally provided herein is the use of at least one chemical entity as described herein, such as a compound of Formula (I), (I-A), (I-A1), (I-B), (I-B1), (I-C), (I-C1), (I-C2), (I-D), or (I-D1), or a compound of Table 1, or stereoisomer or tautomer thereof, or a pharmaceutically acceptable salt of any of the foregoing, in the manufacture of a medicament for potentiating cardiac myosin in an individual or subject.

In some embodiments, the methods provided herein further comprise monitoring the effectiveness of the treatment. Examples of indicators include, but are not limited to improvement in one or more of the following: New York Heart Association (NYHA) Functional Classification, exercise capacity, cardiac elasticity, diastolic left ventricular relaxation, left atrial pressure, paroxysmal or permanent atrial fibrillation, left atrial and pulmonary capillary wedge pressures, left ventricular diastolic pressures, syncope, ventricular relaxation during diastole, ventricular fibrosis, left ventricular hypertrophy, left ventricular mass, left ventricular wall thickness, left ventricular mid-cavity obstruction systolic anterior motion of mitral valve, left ventricular outflow tract obstruction, chest pain, exertional dyspnea, pre-syncope, abnormal exercise capacity, and fatigue. These indicators can be monitored by techniques known in the art including self-reporting; ECG, including ambulatory ECG; echocardiography; cardiac MRI; CT; biopsy; cardiopulmonary exercise testing (CPET); and actigraphy.

In some embodiments, the compound reduces the contractility of a cardiomyocyte. In some embodiments, the compound reduces the contractility of a cardiomyocyte by greater than 40%, such as greater than 45%, 50%, 60%, 70%, 80%, or 90%. In some embodiments, the compound reduced the contractility of a cardiomyocyte 40%-90%, such as 40%-80%, 40-70%, 50%-90%, 50%-80% or 50%-70%. In some embodiments, the compound does not significantly alter calcium transients in the cardiomyocyte. In some embodiments, the compound decreases the ATPase activity in a cardiomyocyte. Methods of measuring contractility, ATPase activity, and calcium transients are known in the art, for example, by calcium labeling, electrophysiological recordings, and microscopic imaging. In some embodiments, the compound does not significantly inhibit or induce a cytochrome P450 (CYP) protein.

In some embodiments, provided herein are compounds of Formula (I), (I-A), (I-A1), (I-B), (I-B1), (I-C), (I-C1), (I-C2), (I-D), or (I-D1), or a compound of Table 1, or a stereoisomer or tautomer thereof, or a pharmaceutically acceptable salt of any of the foregoing, wherein the elimination half-life ($t_{1/2}$; calculated as $\ln(2)/k$, wherein the elimination rate constant, k, is calculated as the absolute value of the slope of the linear regression of logarithm of the concentration versus time for the last three data points of a concentration-time profile) is ≤30 hours in a human. In some embodiments, 10 hours ≤$t_{1/2}$≤30 hours in a human. In some embodiments, $t_{1/2}$ is between about 10 hours and about 30 hours, between about 10 hours and about 25 hours, between about 15 hours and about 30 hours, or between about 15 hours and about 25 hours. In some embodiments, t, is about 12, 15, 18, 21, 24, 27, or 30 hours. In some embodiments, the elimination half-life of a compound provided herein is such that the compound is suitable for once-daily dosing.

In some embodiments, the subject has a left ventricular wall that is thicker than normal prior to treatment. In some embodiments, the subject has a left ventricular wall thickness that is greater than 15 mm, such as greater than 18 mm, 20 mm, 22 mm, 25 mm, or 30 mm prior to treatment. In some embodiments, the left ventricular wall thickness is reduced by greater than 5%, such as greater than 8%, 10%, 12%, 15%, 20%, or 30% following treatment. Left ventricular wall thickness can be measured by methods known in the art, such as by echocardiography, CT scan, or a cardiac MRI.

In some embodiments, the subject has abnormal cardiac fibrosis prior to treatment. In some embodiments, the abnormal cardiac fibrosis is reduced by greater than 5%, such as greater than 8%, 10%, 12%, 15%, 20%, or 30% following treatment. Cardiac fibrosis can be measured by methods known in the art, such as by biopsy or a cardiac MRI.

In some embodiments, the subject has reduced exercise capacity prior to treatment. In some embodiments, the exercise capacity of the subject is increased by greater than 5%, such as greater than 8%, 10%, 12%, 15%, 20% or 30% following treatment. In some embodiments, the exercise capacity is measured by cardiopulmonary exercise testing (CPET). CPET measures changes in oxygen consumption ($VO_2$ max). Methods of measuring CPET and $VO_2$ max are well known in the art (Malhotra et al., JACC: Heart Failure, 2016, 4(8): 607-616; Guazzi et al., J Amer College Cardiol, 2017, 70 (13): 1618-1636; Rowin et al., JACC: Cariovasc Imaging, 2017, 10(11):1374-1386). In some embodiments, $VO_2$ max is improved by more than 1 $mL/kg/m^2$, such as more than 1.2 $mL/kg/m^2$, 1.4 $mL/kg/m^2$, 1.5 $mL/kg/m^2$, 1.7 $mL/kg/m^2$, 2 $mL/kg/m^2$, 2.2 $mL/kg/m^2$, 2.5 $mL/kg/m^2$, 3 $mL/kg/m^2$, 3.2 $mL/kg/m^2$, or 3.5 $mL/kg/m^2$ following treatment.

In some embodiments, the subject has a New York Heart Association (NYHA) Functional Classification of II, III, or IV prior to treatment. In some embodiments, the subject has a New York Heart Association (NYHA) Functional Classification of III or IV prior to treatment. In some embodiments, the subject has a New York Heart Association (NYHA) Functional Classification of IV prior to treatment. In some embodiments, the subject remains in the same NYHA functional class or has a reduced NYHA functional class following treatment.

In some embodiments, $VO_2$ max is improved by more than 1 $mL/kg/m^2$, such as more than 1.2 $mL/kg/m^2$, 1.4 $mL/kg/m^2$, 1.5 $mL/kg/m^2$, 1.7 $mL/kg/m^2$, or 2 $mL/kg/m^2$ and the subject has a reduced NYHA functional class following treatment. In some embodiments, $VO_2$ max is improved by more than 2.5 $mL/kg/m^2$, 3 $mL/kg/m^2$, 3.2 $mL/kg/m^2$, or 3.5 $mL/kg/m^2$ and the subject remains in the same NYHA functional class or has a reduced NYHA functional class following treatment.

In some embodiments, daily function and/or activity level of the subject is improved following treatment. Improved daily function and/or activity level may be measured, for example, by journaling or actigraphy, such as a FitBit or FitBit-like monitors.

In some embodiments, the subject has one or more of decreased shortness of breath, decreased chest pain, decreased arrhythmia burden, such as atrial fibrillation and ventricular arrhythmias, decreased incidence of heart failure, and decreased ventricular outflow obstruction following treatment.

Dosages

The compounds and compositions disclosed and/or described herein are administered at a therapeutically effective dosage, e.g., a dosage sufficient to provide treatment for the disease state. While human dosage levels have yet to be optimized for the chemical entities described herein, generally, a daily dose ranges from about 0.01 to 100 mg/kg of body weight; in some embodiments, from about 0.05 to 10.0 mg/kg of body weight, and in some embodiments, from about 0.10 to 1.4 mg/kg of body weight. Thus, for administration to a 70 kg person, in some embodiments, the dosage range would be about from 0.7 to 7000 mg per day; in some embodiments, about from 3.5 to 700.0 mg per day, and in some embodiments, about from 7 to 100.0 mg per day. The amount of the chemical entity administered will be dependent, for example, on the subject and disease state being treated, the severity of the affliction, the manner and schedule of administration and the judgment of the prescribing physician. For example, an exemplary dosage range for oral administration is from about 5 mg to about 500 mg per day, and an exemplary intravenous administration dosage is from about 5 mg to about 500 mg per day, each depending upon the compound pharmacokinetics.

A daily dose is the total amount administered in a day. A daily dose may be, but is not limited to be, administered each day, every other day, each week, every 2 weeks, every month, or at a varied interval. In some embodiments, the daily dose is administered for a period ranging from a single day to the life of the subject. In some embodiments, the daily dose is administered once a day. In some embodiments, the daily dose is administered in multiple divided doses, such as in 2, 3, or 4 divided doses. In some embodiments, the daily dose is administered in 2 divided doses.

Administration of the compounds and compositions disclosed and/or described herein can be via any accepted mode of administration for therapeutic agents including, but not limited to, oral, sublingual, subcutaneous, parenteral, intravenous, intranasal, topical, transdermal, intraperitoneal, intramuscular, intrapulmonary, vaginal, rectal, or intraocular administration. In some embodiments, the compound or composition is administered orally or intravenously. In some embodiments, the compound or composition disclosed and/or described herein is administered orally.

Pharmaceutically acceptable compositions include solid, semi-solid, liquid and aerosol dosage forms, such as tablet, capsule, powder, liquid, suspension, suppository, and aerosol forms. The compounds disclosed and/or described herein can also be administered in sustained or controlled release dosage forms (e.g., controlled/sustained release pill, depot injection, osmotic pump, or transdermal (including electrotransport) patch forms) for prolonged timed, and/or pulsed administration at a predetermined rate. In some embodiments, the compositions are provided in unit dosage forms suitable for single administration of a precise dose.

The compounds disclosed and/or described herein can be administered either alone or in combination with one or more conventional pharmaceutical carriers or excipients (e.g., mannitol, lactose, starch, magnesium stearate, sodium saccharine, talcum, cellulose, sodium crosscarmellose, glucose, gelatin, sucrose, magnesium carbonate). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate). Generally, depending on the intended mode of administration, the pharmaceutical composition will contain about 0.005% to 95%, or about 0.5% to 50%, by weight of a compound disclosed and/or described herein. Actual methods of preparing such dosage forms are known, or will be apparent, to those skilled in this art; for example, see *Remington's Pharmaceutical Sciences*, Mack Publishing Company, Easton, Pennsylvania.

In some embodiments, the compositions will take the form of a pill or tablet and thus the composition may contain, along with a compounds disclosed and/or described herein, one or more of a diluent (e.g., lactose, sucrose, dicalcium phosphate), a lubricant (e.g., magnesium stearate), and/or a binder (e.g., starch, gum acacia, polyvinylpyrrolidine, gelatin, cellulose, cellulose derivatives). Other solid dosage forms include a powder, marume, solution or suspension (e.g., in propylene carbonate, vegetable oils or triglycerides) encapsulated in a gelatin capsule.

Liquid pharmaceutically administrable compositions can, for example, be prepared by dissolving, dispersing or suspending etc. a compound disclosed and/or described herein and optional pharmaceutical additives in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of the compound contained in such parenteral compositions depends, for example, on the physical nature of the compound, the activity of the compound and the needs of the subject. However, percentages of active ingredient of 0.01% to 10% in solution are employable, and may be higher if the composition is a solid which will be subsequently diluted to another concentration. In some embodiments, the composition will comprise from about 0.2 to 2% of a compound disclosed and/or described herein in solution.

Pharmaceutical compositions of the compounds disclosed and/or described herein may also be administered to the respiratory tract as an aerosol or solution for a nebulizer, or as a microfine powder for insufflation, alone or in combination with an inert carrier such as lactose. In such a case, the particles of the pharmaceutical composition may have diameters of less than 50 microns, or in some embodiments, less than 10 microns.

In addition, pharmaceutical compositions can include a compound disclosed and/or described herein and one or more additional medicinal agents, pharmaceutical agents, adjuvants, and the like. Suitable medicinal and pharmaceutical agents include those described herein.

Kits

Also provided are articles of manufacture and kits containing any of the compounds or pharmaceutical compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use.

In one aspect, provided herein are kits containing a compound or composition described herein and instructions for use. The kits may contain instructions for use in the treatment of a heart disease in an individual or subject in need thereof. A kit may additionally contain any materials or equipment that may be used in the administration of the compound or composition, such as vials, syringes, or IV bags. A kit may also contain sterile packaging.

Combinations

The compounds and compositions described and/or disclosed herein may be administered alone or in combination with other therapies and/or therapeutic agents useful in the treatment of the aforementioned disorders, diseases, or conditions.

The compounds and compositions described and/or disclosed herein may be combined with one or more other therapies to treat a heart disease, such as HCM or HFpEF. In some embodiments, the one or more therapies include therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors). In some embodiments, the one or more therapies include therapies that improve cardiac function by stimulating cardiac contractility (e.g., positive inotropic agents, such as the β-adrenergic agonist dobutamine or the phosphodiesterase inhibitor milrinone). In other embodiments, the one or more therapies include therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

The compounds and compositions described and/or disclosed herein may be combined with one or more other therapies to treat HCM or HFpEF. In some embodiments, the compounds and/compositions may be combined with a β-blocker, verapamil, and/or disopyramide.

General Synthetic Methods

Compounds of Formula (I), (I-A), (I-A1), (I-B), (I-B1), (I-C), (I-C1), (I-C2), (I-D), or (I-D1) will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate. Unless otherwise specified, the variables are as defined above in reference to Formula (I), (I-A), (I-A1), (I-B), (I-B1), (I-C), (I-C1), (I-C2), (I-D), or (I-D1).

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General methods of preparing compounds described herein are depicted in exemplified methods below. Variable groups in the schemes provided herein are defined as for Formula (I), (I-A), (I-A1), (I-B), (I-B1), (I-C), (I-C1), (I-C2), (I-D), or (I-D1), or any variation thereof. Other compounds described herein may be prepared by similar methods.

In some embodiments, compounds provided herein may be synthesized according to Scheme 1.

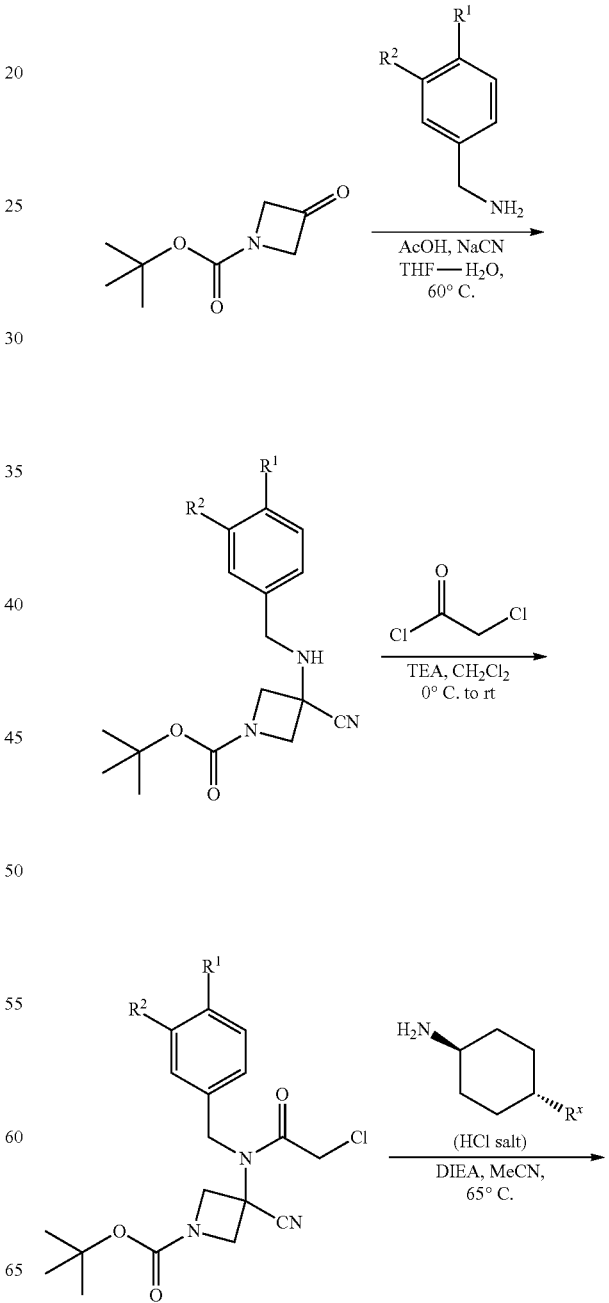

-continued

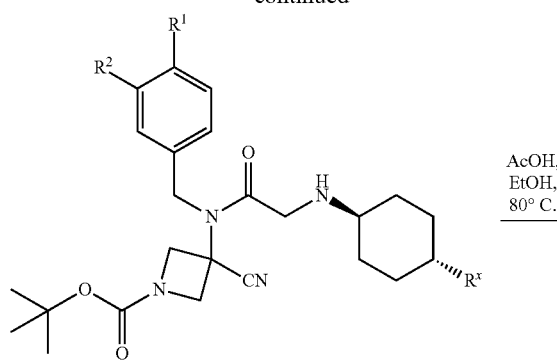

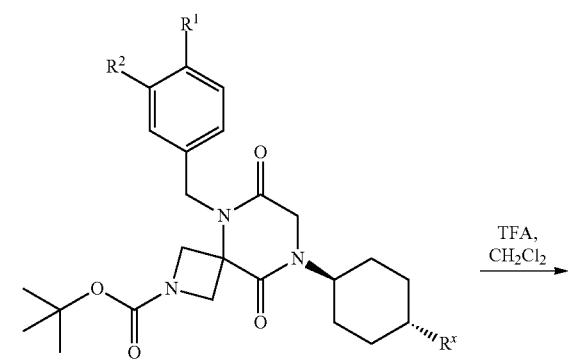

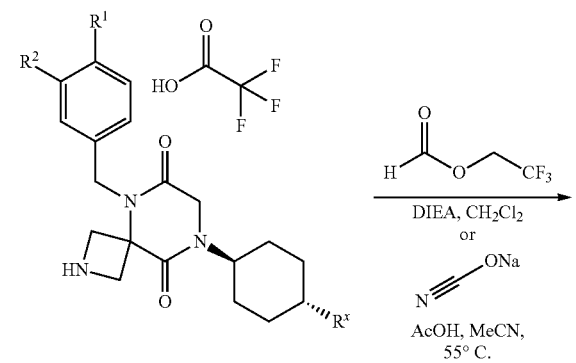

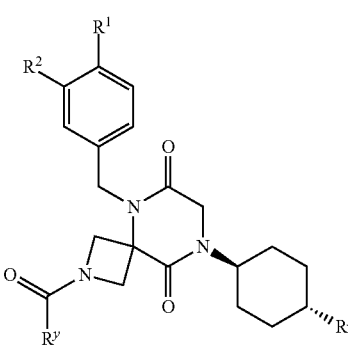

In Scheme 1, $R^1$ and $R^2$ are as defined elsewhere herein for a compound of Formula (I), or any variation or embodiment thereof, or a stereoisomer or tautomer thereof, or a pharmaceutically acceptable salt of any of the foregoing; $R^x$ is $C_{1-6}$alkyl or $C_{1-6}$haloalkyl; and $R^y$ is H or —$NH_2$.

In some embodiments, compounds provided herein may be synthesized according to Scheme 2.

Scheme 2

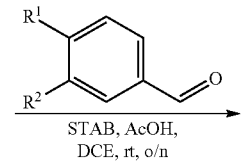
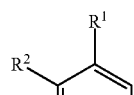
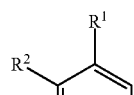
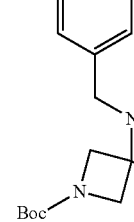
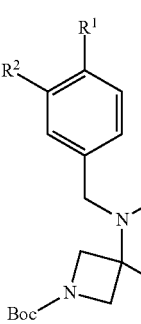
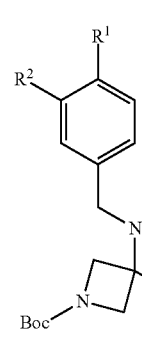
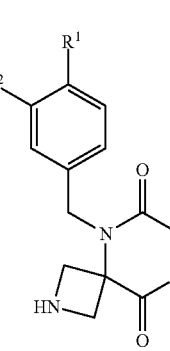
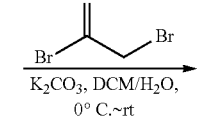
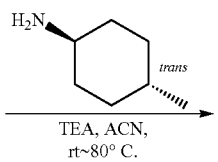
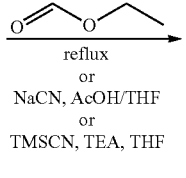

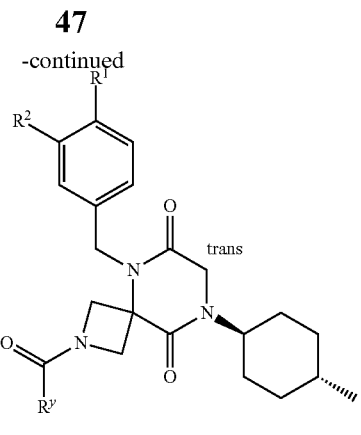
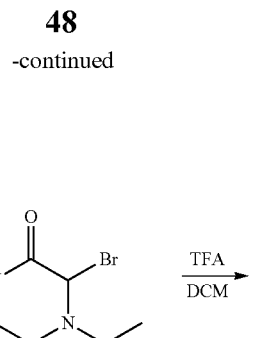
In Scheme 2, $R^1$ and $R^2$ are as defined elsewhere herein for a compound of Formula (I), or any variation or embodiment thereof, or a stereoisomer or tautomer thereof, or a pharmaceutically acceptable salt of any of the foregoing; and $R^y$ is H or —$NH_2$.
In some embodiments, compounds provided herein may be synthesized according to Scheme 3.
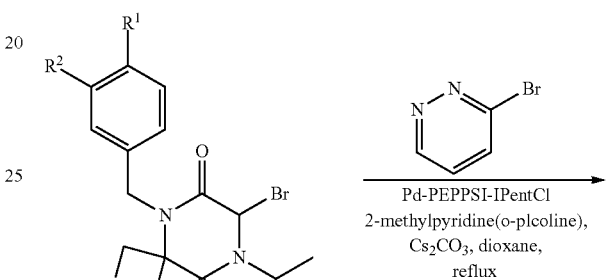
Scheme 3
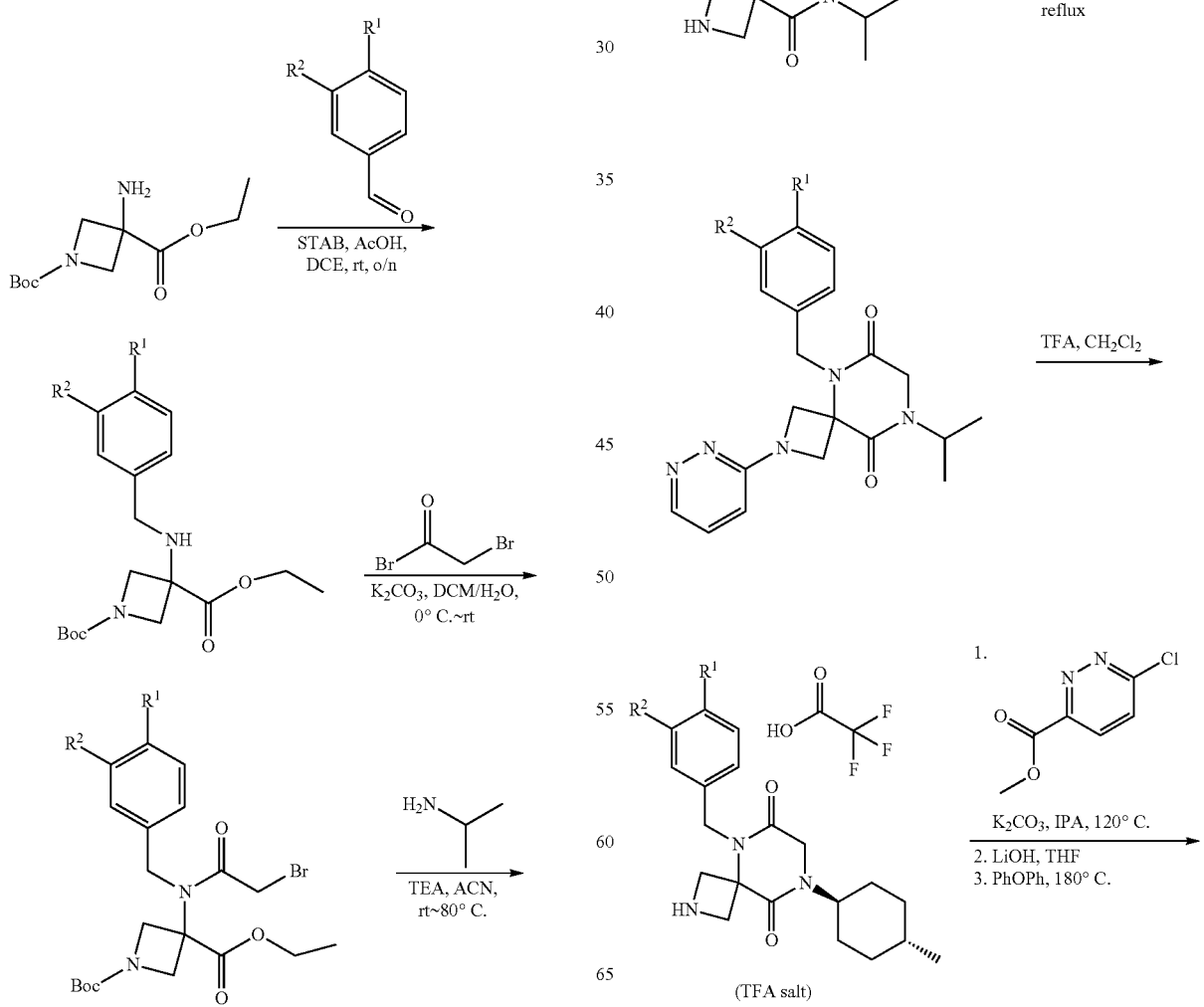

-continued

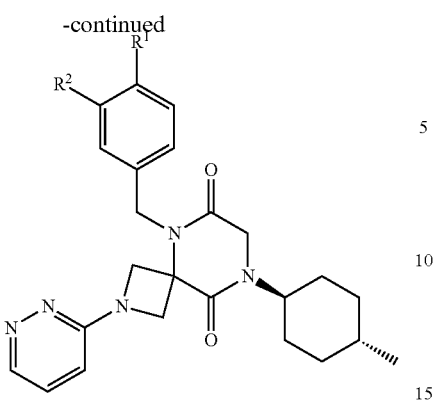

In Scheme 3, $R^1$ and $R^2$ are as defined elsewhere herein for a compound of Formula (I), or any variation or embodiment thereof, or a stereoisomer or tautomer thereof, or a pharmaceutically acceptable salt of any of the foregoing.

Particular non-limiting examples are provided in the Example section below.

EXAMPLES

The following examples are offered to illustrate but not to limit the compositions, uses, and methods provided herein. The compounds are prepared using the general methods described above.

The following abbreviations may be used throughout the Examples: TEA (trimethylamine), DCM (dichloromethane), (Boc)$_2$O (di-tert-butyl decarbonate), EA (Ethyl acetate), PE (Petroleum ether, DMF (N,N-dimethylformamide), DIEA (N-ethyl-N-isopropylpropan-2-amine), HATU (1-[Bis(dimethylamino)methylene]-1H-1,2,3-triazolo[4,5-b]pyridinium 3-oxid hexafluorophosphate), HOAt (1-Hydroxy-7-azabenzotriazole), HOBt (Hydroxybenzotriazole), EDCI (1-Ethyl-3-(3-dimethylaminopropyl)carbodiimide), MeOH (methanol), EtOH (ethanol), IPA (iPrOH; propan-2-ol), NMP (1-methylpyrrolidin-2-one), STAB (sodium triacetoxyhydroborate), ACN (acetonitrile), TFA (trifluoroacetic acid), DPPA (Diphenylphosphoryl azide), DBU (1,8-Diazabicyclo (5.4.0)undec-7-ene), THF (tetrahydrofuran), PPh$_3$ (triphenylphosphane), SM (starting material), Hex (hexane), NCS (N-chlorosuccinimide), r.t. (room temperature), DCE (dichloroethane), FA (formic acid), CHCl$_3$ (Chloroform), BnBr (benzyl bromide), HCl (hydrogen chloride), equiv (equivalent), RT (retention time), SFC (supercritical fluid chromatography), and DSC (bis(2,5-dioxopyrrolidin-1-yl) carbonate).

XRPD diffractograms were collected using the following parameters:

XRPD Machine: Rigaku MiniFlex600 6G Benchtop X-ray Diffraction System; X-ray Generator: Delivering 600 W of Power (40 kV/15 mA); Sealed-off X-ray Tube: Toshiba A-21-Cu Tube w/Normal Focus; X-ray radiation: CuKα; Software: Smartlab Studio II x64 ver. 4.5.352.0 (data collection & analysis); Incident Soller Slit: 2.5°; Divergence Slit:1.25°; Length Limiting Slit: 10; Sample Stage: ASC-8 PM_MF; Filter: Cu_beta_X15; Receiving Soller Slit: 2.5°; Scattering Slit: 8.0 mm; Receiving Slit: 0.3 mm; Detector: High Speed D/tex Utra2 MF RAC; Power: 40 kV/15 mA; Scanning Rate: 2° θ/min; Step: 0.01° θ; Scanning Range: 3°-30° θ or 3°-40° θ; Sample Holder: Zero Background Si Sample Holder w/0.2 mm Indent.

Example 1

Synthesis of 5-(3,4-difluorobenzyl)-8-((1r,4r)-4-methylcyclohexyl)-6,9-dioxo-2,5,8-triazaspiro[3.5]nonane-2-carbaldehyde Compound 4

Step 1: Synthesis of 1-(tert-butyl) 3-ethyl 3-((3,4-difluorobenzyl)amino)azetidine-1,3-dicarboxylate

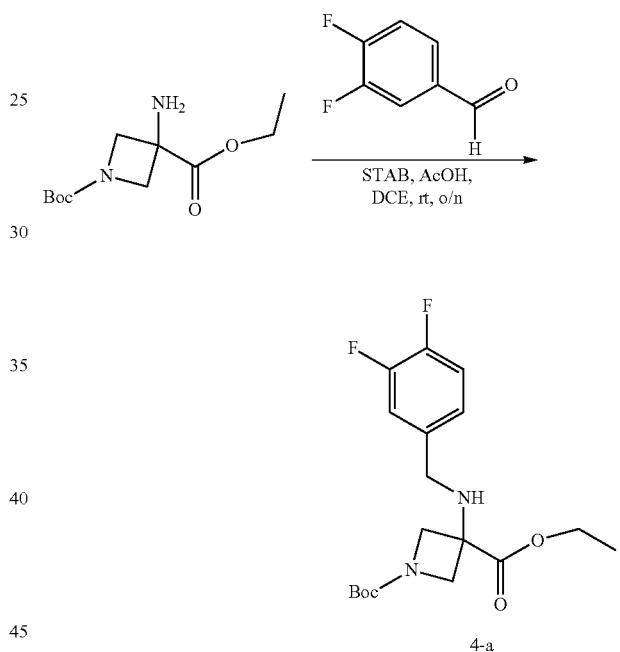

To a solution of 1-tert-butyl 3-ethyl 3-aminoazetidine-1,3-dicarboxylate (4.0 g, 16.4 mmol, 1.0 equiv) and 3,4-difluorobenzaldehyde (2.4 g, 19.6 mmol, 1.2 equiv) in DCE (40.0 mL) at 0° C. were added STAB (7.0 g, 32.8 mmol, 2.0 equiv) and AcOH (2.0 g, 32.8 mmol, 2.0 equiv). The resulting mixture was stirred at r.t. overnight, adjusted the pH to 8 with ammonium hydroxide, added water (50.0 mL) and extracted with DCM (50.0 mL) twice. The combined organic layers were washed with brine (50 mL) twice, dried over anhydrous Na$_2$SO$_4$, and concentrated under reduced pressure to afford 6.0 g of 1-tert-butyl 3-ethyl 3-(3,4-difluorobenzyl)amino)azetidine-1,3-dicarboxylate as a yellow oil. LRMS (ES) m/z 315 (M+H−56).

Step 2: Synthesis of 1-(tert-butyl) 3-ethyl 3-(2-bromo-N-(3,4-difluorobenzyl)acetamido)azetidine-1,3-dicarboxylate Step 3: Synthesis of tert-butyl 5-(3,4-difluorobenzyl)-8-((1r,4r)-4-methylcyclohexyl)-6,9-dioxo-2,5,8-triazaspiro[3.5]nonane-2-carboxylate

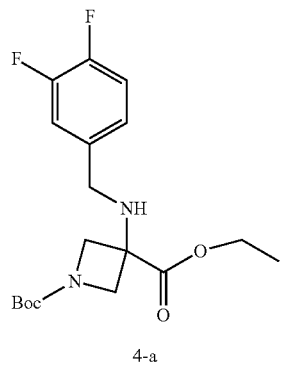

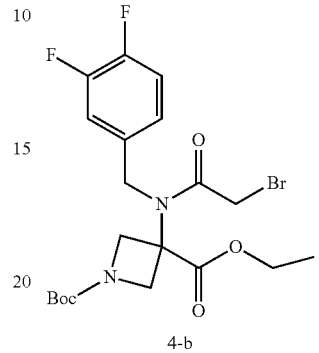

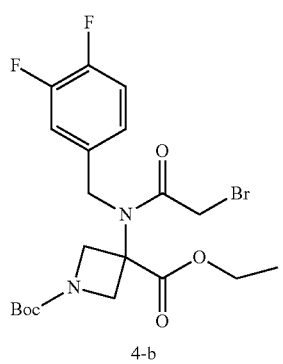

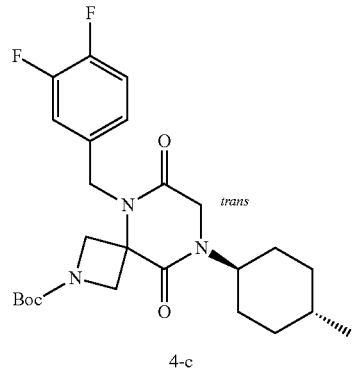

To a solution of 1-tert-butyl 3-ethyl 3-[[(3,4-difluorophenyl)methyl]amino]azetidine-1,3-dicarboxylate (6.0 g, 16.2 mmol, 1.0 equiv) in DCM (60.0 mL) at 0° C. were added a solution of K$_2$CO$_3$ (3.4 g, 24.3 mmol, 1.50 equiv) in water (30 mL), and then bromoacetyl bromide (3.9 g, 19.4 mmol, 1.2 equiv) dropwise over a period of 10 min. The resulting mixture was stirred at r.t. overnight and extracted with DCM (50.0 mL) twice. The combined organic layers were washed with brine (100 mL) twice, dried over anhydrous Na$_2$SO$_4$, and concentrated under reduced pressure to afford 8.0 g of 1-(tert-butyl) 3-ethyl 3-(2-bromo-N-(3,4-difluorobenzyl)acetamido)azetidine-1,3-dicarboxylate as a yellow oil. LRMS (ES) m/z 435 (M+H−56).

To a solution of 1-(tert-butyl) 3-ethyl 3-(2-bromo-N-(3,4-difluorobenzyl)acetamido)azetidine-1,3-dicarboxylate (8.0 g, 16.3 mmol, 1.0 equiv) in ACN (80 mL) were added TEA (4.9 g, 48.4 mmol, 3.0 equiv) and trans-(1r,4r)-4-methylcyclohexan-1-amine (2.8 g, 24.7 mmol, 1.5 equiv). The resulting mixture was stirred at r.t. for 1 h, gradually warmed to 80° C., and stirred at 80° C. overnight. The mixture was cooled to r.t., concentrated under reduced pressure, and triturated with a mixture of PE and EA (7/1; 80 mL) to afford 7 g (~80% purity) of tert-butyl 5-(3,4-difluorobenzyl)-8-((1r,4r)-4-methylcyclohexyl)-6,9-dioxo-2,5,8-triazaspiro[3.5]nonane-2-carboxylate as an off-white solid. LRMS (ES) m/z 422 (M+H−56).

Step 4: Synthesis of 5-(3,4-difluorobenzyl)-8-((1r,4r)-4-methylcyclohexyl)-2,5,8-triazaspiro[3.5]nonane-6,9-dione Step 5: Synthesis of 5-(3,4-difluorobenzyl)-8-((1r,4r)-4-methylcyclohexyl)-6,9-dioxo-2,5,8-triazaspiro[3.5]nonane-2-carbaldehyde (Compound 4)

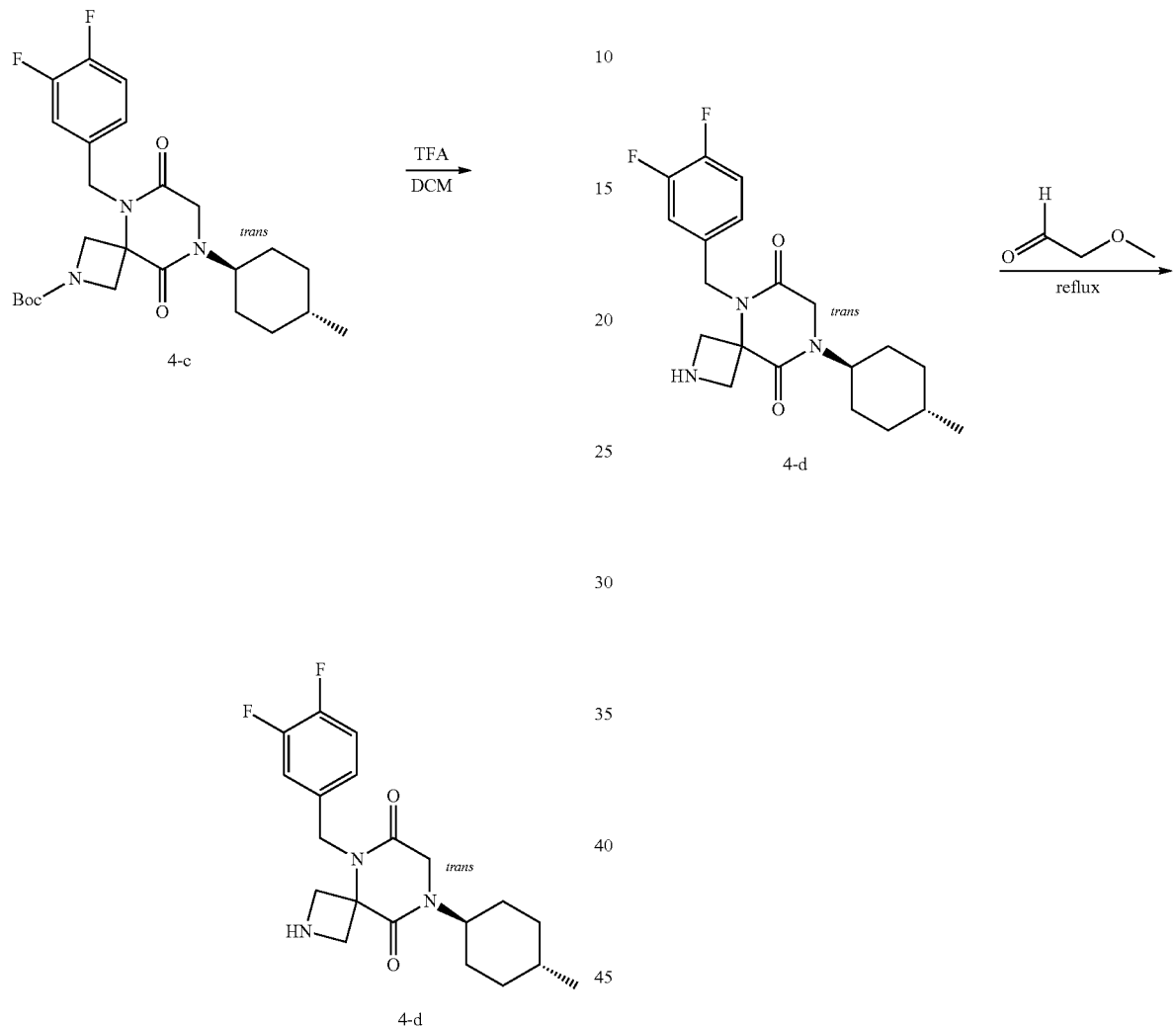

To a stirred solution of tert-butyl 5-(3,4-difluorobenzyl)-8-((1r,4r)-4-methylcyclohexyl)-6,9-dioxo-2,5,8-triazaspiro[3.5]nonane-2-carboxylate (7.0 g, 14.7 mmol, 1.0 equiv) in DCM (70.0 mL) was added TFA (18.0 mL). The resulting mixture was stirred at r.t. for 3 h, diluted with water (100.0 mL), adjusted the pH to 13-14 with aqueous NaOH solution (2 N), and extracted with DCM (100 mL) twice. The combined organic layers were washed with brine (100.0 mL) twice, dried over anhydrous $Na_2SO_4$, and concentrated under reduced pressure to afford 4.5 g (~80% purity) of 5-(3,4-difluorobenzyl)-8-((1r,4r)-4-methylcyclohexyl)-2,5,8-triazaspiro[3.5]nonane-6,9-dione as a yellow semi-solid. LRMS (ES) m/z 378 (M+H).

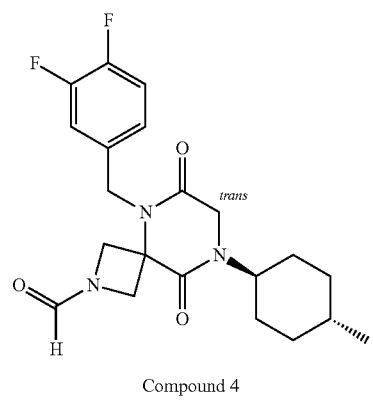

Compound 4

A solution of tert-butyl 5-(3,4-difluorobenzyl)-8-((1r,4r)-4-methylcyclohexyl)-6,9-dioxo-2,5,8-triazaspiro[3.5]nonane-2-carboxylate (1.5 g, 4.0 mmol, 1.0 equiv) in ethyl formate (15.0 mL) was stirred at 80° C. overnight. The mixture was cooled to r.t., concentrated under reduced pressure, and purified by C18 column chromatography, eluted with a mixture of water (0.05% NH$_4$HCO$_3$)/CH$_3$CN (3:2) to afford 1.3 g (81%) of 5-(3,4-difluorobenzyl)-8-((1r,4r)-4-methylcyclohexyl)-6,9-dioxo-2,5,8-triazaspiro[3.5]nonane-2-carbaldehyde as an amorphous white solid. An experimental X-ray powder diffraction (XRPD) pattern of this amorphous white solid is shown in FIG. 1 LRMS (ES) m/z 406 (M+H); $^1$H NMR (300 MHz, DMSO-d6) δ 7.96 (s, 1H), 7.47-7.29 (m, 2H), 7.10 (ddd, J=9.4, 4.4, 2.0 Hz, 1H), 4.82 (s, 2H), 4.50 (d, J=9.6 Hz, 1H), 4.15-4.28 (m, J=3H), 4.01 (s, 2H), 3.96 (d, J=10.8 Hz, 1H), 1.80-1.69 (m, 2H), 1.65-1.48 (m, 4H), 1.35 (d, J=10.9 Hz, 1H), 1.13-0.93 (m, 2H), 0.88 (d, J=6.5 Hz, 3H).

Example 2

Synthesis of 5-(3,4-difluorobenzyl)-8-((1r,4r)-4-methylcyclohexyl)-6,9-dioxo-2,5,8-triazaspiro[3.5]nonane-2-carboxamide Compound 5

Step 1: Synthesis of 5-(3,4-difluorobenzyl)-8-((1r,4r)-4-methylcyclohexyl)-6,9-dioxo-2,5,8-triazaspiro[3.5]nonane-2-carboxamide (Compound 5)

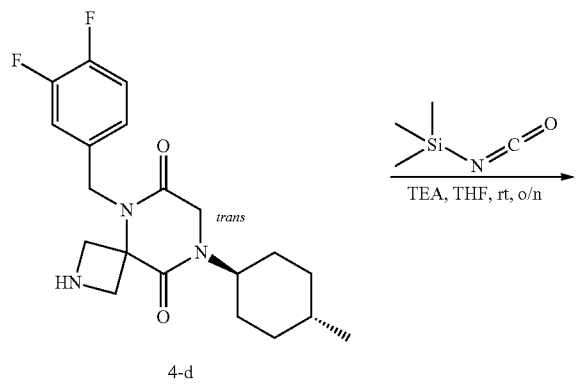

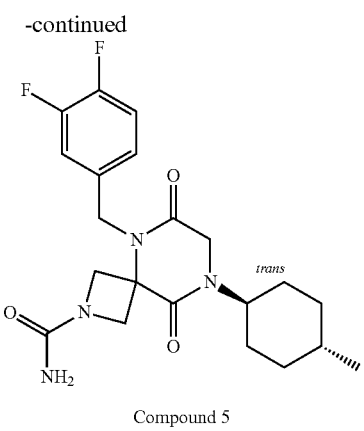

Compound 5

To a stirred solution of tert-butyl 5-(3,4-difluorobenzyl)-8-((1r,4r)-4-methylcyclohexyl)-6,9-dioxo-2,5,8-triazaspiro[3.5]nonane-2-carboxylate (1.5 g, 4.0 mmol, 1.0 equiv) in THF (15.0 mL) at 0° C. were added TEA (1.2 g, 11.9 mmol, 3.0 equiv) and isocyanatotrimethylsilane (685 mg, 6.0 mmol, 1.5 equiv) dropwise over a period of 5 min. The resulting mixture was stirred at r.t. overnight, concentrated under reduced pressure, and triturated first with a mixture of PE and EA (5/1; 20 mL) and then with hexane (20 mL) to afford 1.4 g (84%) of 5-(3,4-difluorobenzyl)-8-((1r,4r)-4-methylcyclohexyl)-6,9-dioxo-2,5,8-triazaspiro[3.5]nonane-2-carboxamide as an off-white solid. LRMS (ES) m/z 421 (M+H); $^1$H NMR (400 MHz, DMSO-d6) δ 7.55-7.30 (m, 2H), 7.09 (dd, J=8.0, 4.3 Hz, 1H), 6.00 (s, 2H), 4.82 (s, 2H), 4.20 (t, J=9.1 Hz, 3H), 3.99 (s, 2H), 3.84 (d, J=9.3 Hz, 2H), 1.74 (d, J=12.9 Hz, 2H), 1.58 (dtt, J=20.6, 12.1, 6.1 Hz, 4H), 1.42-1.29 (m, 1H), 1.04 (qd, J=12.2, 4.5 Hz, 2H), 0.88 (d, J=6.5 Hz, 3H).

Compounds in the following table were prepared in a similar manner as Compound 5.

| No. | Structure | Name and Data |
|---|---|---|
| 1 | (4-chlorobenzyl structure) | 5-(4-chlorobenzyl)-8-((1r,4r)-4-ethylcyclohexyl)-6,9-dioxo-2,5,8-triazaspiro[3.5]nonane-2-carboxamide. LRMS (ES) m/z 433.1 (M + H); $^1$H NMR (400 MHz, Methanol-d4) δ 7.35 (d, J = 8.2 Hz, 2H), 7.28 (d, J = 8.2 Hz, 2H), 4.95 (s, 2H), 4.40 (d, J = 9.4 Hz, 2H), 4.30 (tt, J = 12.3, 3.9 Hz, 1H), 4.10-4.06 (m, 4H), 1.91 (d, J = 12.0 Hz, 2H), 1.78-1.70 (m, 2H), 1.58 (qd, J = 12.0, 2.6 Hz, 2H), 1.27 (p, J = 7.1 Hz, 2H), 1.20-1.02 (m, 3H), 0.92 (t, J = 7.4 Hz, 3H). |

| No. | Structure | Name and Data |
|---|---|---|
| 2 | 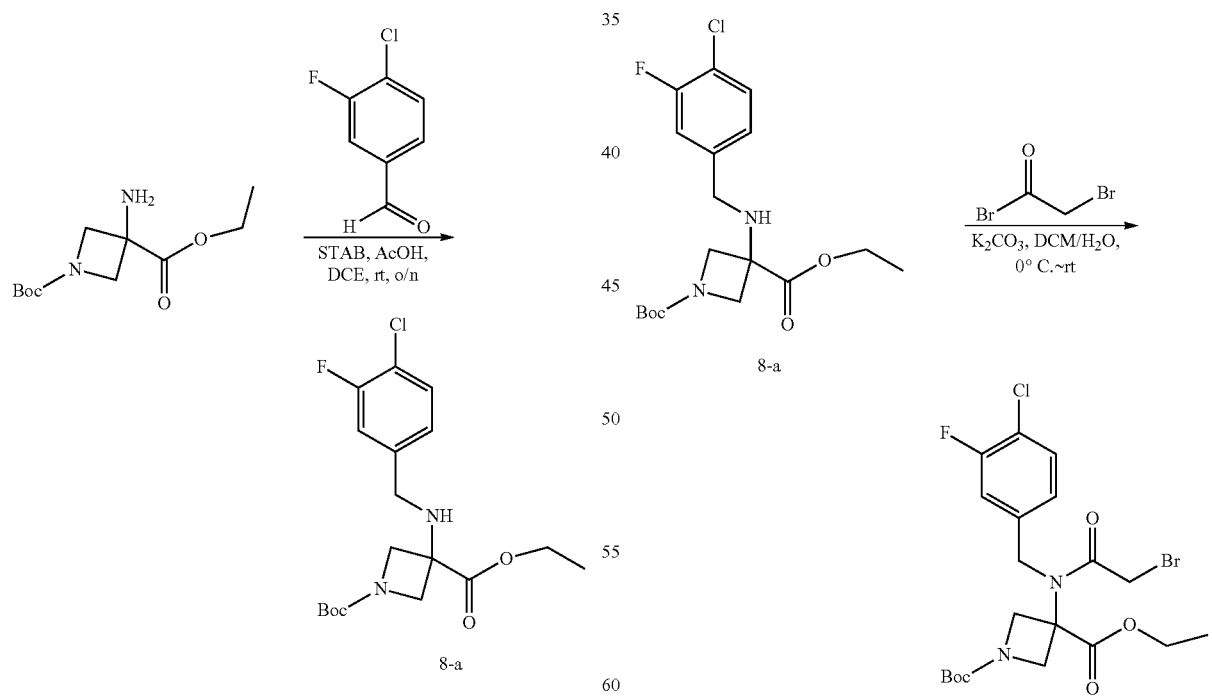 | 8-((1r,4r)-4-ethylcyclohexyl)-5-(4-fluorobenzyl)-6,9-dioxo-2,5,8-triazaspiro[3.5]nonane-2-carboxamide. LRMS (ES) m/z 417.2 (M + H). 1H NMR (400 MHz, Methanol-d4) δ 7.31 (dd, J = 8.4, 5.5 Hz, 2H), 7.07 (t, J = 8.5 Hz, 2H), 4.96 (s, 2H), 4.39 (d, J = 9.4 Hz, 2H), 4.31 (td, J = 12.1, 6.0 Hz, 1H), 4.09 (d, J = 10.1 Hz, 4H), 1.91 (d, J = 12.5 Hz, 2H), 1.74 (d, J = 10.3 Hz, 2H), 1.59 (qd, J = 12.0, 2.8 Hz, 2H), 1.27 (p, J = 7.1 Hz, 2H), 1.21-1.02 (m, 3H), 0.92 (t, J = 7.4 Hz, 3H). |

Example 3

Synthesis of 5-(4-chloro-3-fluorobenzyl)-8-isopropyl-2-(pyridazin-3-yl)-2,5,8-triazaspiro[3.5]nonane-6,9-dione Compound 8

Step 1: Synthesis of 1-(tert-butyl) 3-ethyl 3-(4-chloro-3-fluorobenzyl)amino)azetidine-1,3-dicarboxylate To a solution of 1-tert-butyl 3-ethyl 3-aminoazetidine-1,3-dicarboxylate (2.0 g, 8.2 mmol, 1.0 equiv) and 4-chloro-3-fluorobenzaldehyde (2.0 g, 12.3 mmol, 1.5 equiv) in DCE (20.0 mL) at 0° C. were added AcOH (984 mg, 16.4 mmol, 2.0 equiv.) and STAB (3.5 g, 16.5 mmol, 2.0 equiv) in portions. The resulting mixture was stirred at r.t. overnight, adjusted the pH to 8 with ammonium hydroxide, added water (30.0 mL) and extracted twice with DCM (30.0 mL). The combined organic layers were washed with brine (30.0 mL) twice, dried over anhydrous Na₂SO₄, and concentrated under reduced pressure to afford 3.0 g of 1-tert-butyl 3-ethyl 3-(4-chloro-3-fluorobenzyl)amino)azetidine-1,3-dicarboxylate as a yellow oil. LRMS (ES) m/z 331 (M+H−56).

Step 2: Synthesis of 1-(tert-butyl) 3-ethyl 3-(2-bromo-N-(4-chloro-3-fluorobenzyl)acetamido)azetidine-1,3-dicarboxylate To a stirred solution of 1-tert-butyl 3-ethyl 3-(4-chloro-3-fluorobenzyl)amino)azetidine-1,3-dicarboxylate (3.0 g, 7.8 mmol, 1.0 equiv) in DCM (30.0 mL) at 0° C. were added a solution of K₂CO₃ (1.7 g, 12.3 mmol, 1.50 equiv) in water (15 mL), and then bromoacetyl bromide (1.9 g, 9.4 mmol, 1.2 equiv) dropwise over a period of 5 min. The resulting mixture was stirred at r.t. overnight and extracted with DCM (40.0 mL) twice. The combined organic layers were washed with brine (40 mL) twice, dried over anhydrous Na₂SO₄, concentrated under reduced pressure, and purified by C18 column chromatography, eluted with water (0.5% ammonium carbonate) and ACN (1/4) to afford 3.9 g (89%) of 1-(tert-butyl) 3-ethyl 3-(2-bromo-N-(4-chloro-3-fluorobenzyl)acetamido)azetidine-1,3-dicarboxylate as a yellow oil. LRMS (ES) m/z 451 (M+H−56).

Step 3: Synthesis of tert-butyl 5-(4-chloro-3-fluorobenzyl)-8-isopropyl-6,9-dioxo-2,5,8-triazaspiro[3.5]nonane-2-carboxylate

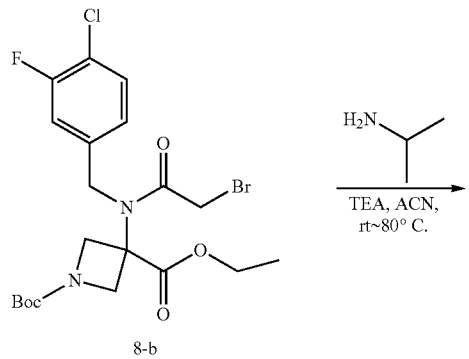

8-b

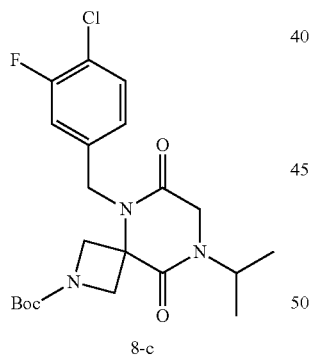

8-c

To a solution of 1-(tert-butyl) 3-ethyl 3-(2-bromo-N-(4-chloro-3-fluorobenzyl)acetamido)azetidine-1,3-dicarboxylate (1.5 g, 3.0 mmol, 1.0 equiv) in ACN (20 mL) were added TEA (898 mg, 8.9 mmol, 3.0 equiv) and isopropylamine (262 mg, 4.4 mmol, 1.5 equiv). The resulting mixture was stirred at r.t. for 1 h, gradually warmed to 80° C., and stirred at 80° C. overnight. The mixture was cooled to r.t. and added water while stirring. The precipitated solids were collected by filtration and washed with water (50.0 mL) to afford 1.1 g (85%) of tert-butyl 5-(4-chloro-3-fluorobenzyl)-8-isopropyl-6,9-dioxo-2,5,8-triazaspiro[3.5]nonane-2-carboxylate as an off-white solid. LRMS (ES) m/z 384 (M+H−56).

Step 4: Synthesis of 5-(4-chloro-3-fluorobenzyl)-8-isopropyl-2,5,8-triazaspiro[3.5]nonane-6,9-dione

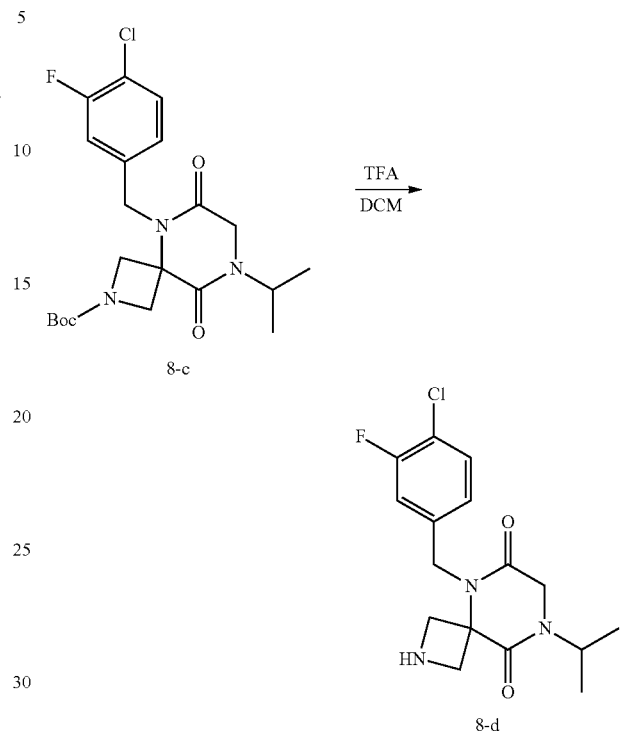

To a stirred solution of tert-butyl 5-(4-chloro-3-fluorobenzyl)-8-isopropyl-6,9-dioxo-2,5,8-triazaspiro[3.5]nonane-2-carboxylate (1.1 g, 2.4 mmol, 1.0 equiv) in DCM (12.0 mL) was added TFA (3.0 mL). The resulting mixture was stirred at r.t. for 3 h, diluted with water (20.0 mL), adjusted the pH to 13-14 with aqueous NaOH solution (2N), and extracted with DCM (20 mL) twice. The combined organic layers were washed with brine (20.0 mL) twice, dried over anhydrous Na₂SO₄, and concentrated under reduced pressure to afford 950 mg of 5-(4-chloro-3-fluorobenzyl)-8-isopropyl-2,5,8-triazaspiro[3.5]nonane-6,9-dione as a yellow solid. LRMS (ES) m/z 340 (M+H).

Step 5: Synthesis of 5-(4-chloro-3-fluorobenzyl)-8-isopropyl-2-(pyridazin-3-yl)-2,5,8-triazaspiro[3.5]nonane-6,9-dione (Compound 8)

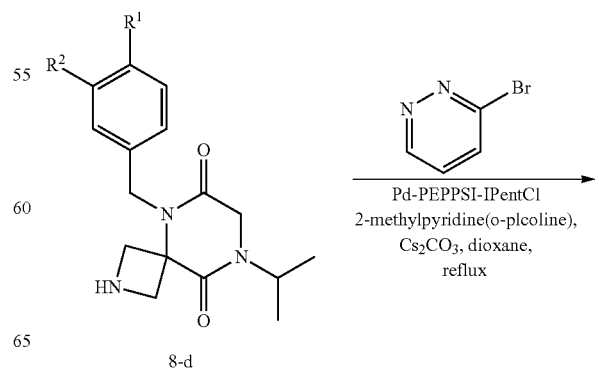

8-d

-continued

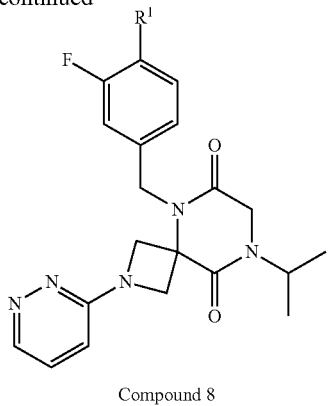

Compound 8

To a stirred solution of 5-(4-chloro-3-fluorobenzyl)-8-isopropyl-2,5,8-triazaspiro[3.5]nonane-6,9-dione (950 mg, 2.8 mmol, 1.0 equiv) and 3-bromopyridazine (662.2 mg, 4.2 mmol, 1.5 equiv) in dioxane (10 mL) were added Cs$_2$CO$_3$ (1.8 g, 5.5 mmol, 2.0 equiv) and Pd-PEPPSI-IPentCl 2-methylpyridine (o-picoline) (117.6 mg, 0.14 mmol, 0.05 equiv). The resulting mixture was stirred at 90° C. overnight under nitrogen atmosphere. The mixture was allowed to cool down to r.t., filtered to remove solids, and purified by C18 column chromatography, eluted with water (0.05% ammonium carbonate)/ACN (2:1) to afford 695 mg (59%) of 5-(4-chloro-3-fluorobenzyl)-8-isopropyl-2,5,8-triazaspiro[3.5]nonane-6,9-dione as a yellow solid. LRMS (ES) m/z 418 (M+H); $^1$H NMR (400 MHz, DMSO-d6) δ 8.59 (dd, J=4.6, 1.3 Hz, 1H), 7.53 (t, J=8.0 Hz, 1H), 7.43-7.34 (m, 2H), 7.14 (dd, J=8.3, 2.0 Hz, 1H), 6.84 (dd, J=9.0, 1.4 Hz, 1H), 4.95 (s, 2H), 4.60 (h, J=6.8 Hz, 1H), 4.47 (d, J=9.5 Hz, 2H), 4.18 (d, J=9.5 Hz, 2H), 4.03 (s, 2H), 1.15 (d, J=6.8 Hz, 6H).

Compounds in the following table were prepared in a similar manner as Compound 8.

| No. | Structure | Name and Data |
|---|---|---|
| 9 | 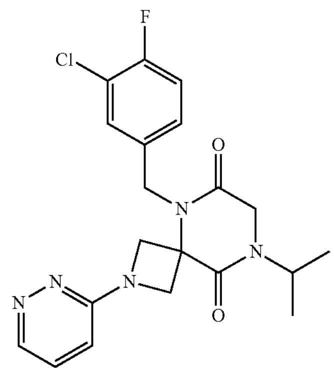 [SMILES: CC(C)N1CC(=O)N(Cc2ccc(F)c(Cl)c2)C2(CN(c3cccnn3)C2)C1=O] | 5-(3-chloro-4-fluorobenzyl)-8-isopropyl-2-(pyridazin-3-yl)-2,5,8-triazaspiro[3.5]nonane-6,9-dione. LRMS (ES) m/z 418.1 (M + H). $^1$H NMR (400 MHz, DMSO-d6) δ 8.59 (dd, J = 4.5, 1.3 Hz, 1H), 7.51 (dd, J = 7.0, 2.2 Hz, 1H), 7.38 (dd, J = 9.0, 4.5 Hz, 1H), 7.35 (t, J = 9.1 Hz, 1H), 7.29-7.24 (m, 1H), 6.84 (dd, J = 8.9, 1.3 Hz, 1H), 4.93 (s, 2H), 4.65-4.54 (m, 1H), 4.46 (d, J = 9.5 Hz, 2H), 4.18 (d, J = 9.5 Hz, 2H), 4.03 (s, 2H), 1.14 (d, J = 6.8 Hz, 6H). |
| 13 | 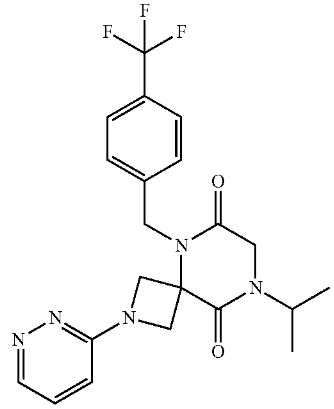 [SMILES: CC(C)N1CC(=O)N(Cc2ccc(C(F)(F)F)cc2)C2(CN(c3cccnn3)C2)C1=O] | 8-isopropyl-2-(pyridazin-3-yl)-5-(4-(trifluoromethyl)benzyl)-2,5,8-triazaspiro[3.5]nonane-6,9-dione. LRMS (ES) m/z 434.1 (M + H). $^1$H NMR (400 MHz, Methanol-d4) δ 8.58 (s, 1H), 7.64 (d, J = 8.1 Hz, 2H), 7.51 (d, J = 8.1 Hz, 2H), 7.46 (s, 1H), 6.89 (d, J = 9.0 Hz, 1H), 5.17 (s, 2H), 4.75 (h, J = 6.9 Hz, 1H), 4.63 (d, J = 9.5 Hz, 2H), 4.33 (d, J = 9.5 Hz, 2H), 4.15 (s, 2H), 1.26 (d, J = 6.8 Hz, 6H). |

| No. | Structure | Name and Data |
|---|---|---|
| 14 | 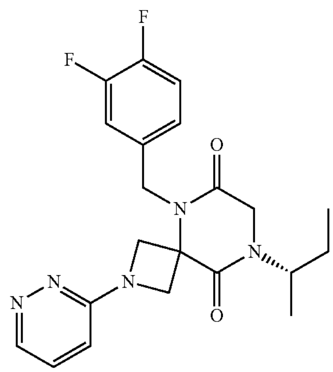 | (S)-8-(sec-butyl)-5-(3,4-difluorobenzyl)-2-(pyridazin-3-3yl)-2,5,8-triazaspiro[3.5]nonane-6,9-dione. LRMS (ES) m/z 416.1 (M + H). ¹H NMR (400 MHz, Methanol-d4) δ 8.58 (s, 1H), 7.47 (dd, J = 9.5, 4.2 Hz, 1H), 7.29-7.17 (m, 2H), 7.14-7.07 (m, 1H), 6.92 (d, J = 9.0 Hz, 1H), 5.06 (s, 2H), 4.63 (dd, J = 9.5, 5.8 Hz, 2H), 4.59-4.49 (m, 1H), 4.37 (dd, J = 11.3, 9.5 Hz, 2H), 4.09 (q, J = 15.8 Hz, 2H), 1.72-1.52 (m, 2H), 1.23 (d, J = 6.9 Hz, 3H), 0.92 (t, J = 7.4 Hz, 3H). |
| 15 | 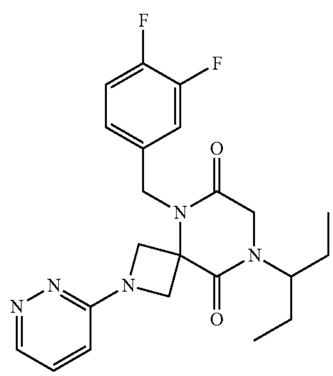 [SMILES: CCC(CC)N1CC(=O)N(Cc2ccc(F)c(F)c2)C2(CN(c3cccnn3)C2)C1=O] | 5-(3,4-difluorobenzyl)-8-(pentan-3-yl)-2-(pyridazin-3-3-yl)-2,5,8-triazaspiro[3.5]nonane-6,9-dione. LRMS (ES) m/z 430.1 (M + H). ¹H NMR (400 MHz, Methanol-d4) δ 8.57 (d, J = 4.6 Hz, 1H), 7.46 (dd, J = 9.1, 4.5 Hz, 1H), 7.25-7.16 (m, 2H), 7.08 (ddd, J = 9.0, 4.2, 1.9 Hz, 1H), 6.92 (dd, J = 9.1, 1.3 Hz, 1H), 5.07 (s, 2H), 4.65 (d, J = 9.5 Hz, 2H), 4.45-4.35 (m, 1H), 4.40 (d, J = 9.5 Hz, 2H), 4.04 (s, 2H), 1.70-1.52 (m, 4H), 0.91 (t, J = 7.4 Hz, 6H). |
| 16 | 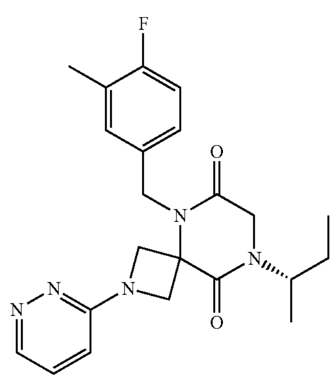 [SMILES: CC[C@H](C)N1CC(=O)N(Cc2ccc(F)c(C)c2)C2(CN(c3cccnn3)C2)C1=O] | (S)-8-(sec-butyl)-5-(4-fluoro-3-methylbenzyl)-2-(pyridazin-3-yl)-2,5,8-triazaspiro[3.5]nonane-6,9-dione. LRMS (ES) m/z 412.1 (M + H). ¹H NMR (400 MHz, Methanol-d4) δ 8.57 (s, 1H), 7.53 (dd, J = 9.1, 4.4 Hz, 1H), 7.15 (dd, J = 7.1, 2.2 Hz, 1H), 7.14-7.08 (m, 1H), 7.01-6.93 (m, 2H), 5.06 (d, J = 16.2 Hz, 1H), 5.00 (d, J = 16.2 Hz, 1H), 4.63 (d, J = 9.7 Hz, 2H), 4.60-4.50 (m, 1H), 4.46-4.38 (m, 2H), 4.16-4.01 (m, 2H), 2.20 (d, J = 1.9 Hz, 3H), 1.73-1.54 (m, 2H), 1.23 (d, J = 6.9 Hz, 3H), 0.92 (t, J = 7.4 Hz, 3H). |
| 17 | 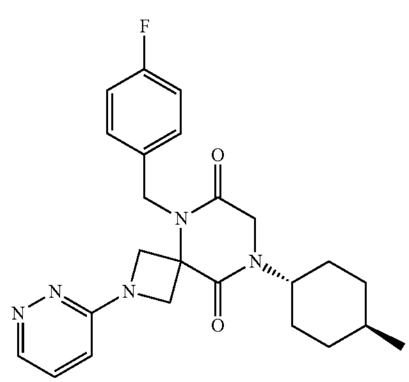 [SMILES: C[C@H]1CC[C@H](N2CC(=O)N(Cc3ccc(F)cc3)C3(CN(c4cccnn4)C3)C2=O)CC1] | 5-(4-fluorobenzyl)-8-((1r,4r)-4-methylcyclohexyl)-2-(pyridazin-3-yl)-2,5,8-triazaspiro[3.5]nonane-6,9-dione. LRMS (ES) m/z 438.2 (M + H). ¹H NMR (400 MHz, Methanol-d4) δ 8.62-8.50 (m, 1H), 7.45 (dd, J = 9.1, 4.5 Hz, 1H), 7.36-7.29 (m, 2H), 7.08-7.00 (m, 2H), 6.89 (dd, J = 9.1, 1.2 Hz, 1H), 5.06 (s, 2H), 4.60 (d, J = 9.5 Hz, 2H), 4.35 (d, J = 9.5 Hz, 3H), 4.14 (s, 2H), 1.88-1.81 (m, 2H), 1.78-1.71 (m, 2H), 1.64 (qd, J = 12.3, 3.6 Hz, 2H), 1.49-1.34 (m, 1H), 1.12 (qd, J = 12.7, 3.6 Hz, 2H), 0.94 (d, J = 6.6 Hz, 3H). |

| No. | Structure | Name and Data |
|---|---|---|
| 19 | 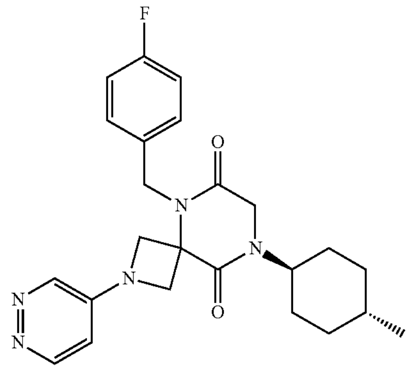 [SMILES: C[C@H]1CC[C@H](N2CC(=O)N(Cc3ccc(F)cc3)C3(CN(c4ccnnc4)C3)C2=O)CC1] | 5-(4-fluorobenzyl)-8-((1r,4r)-4-methylcyclohexyl)-2-(pyridazin-4-yl)-2,5,8-triazaspiro[3.5]nonane-6,9-dione. LRMS (ES) m/z 438.2 (M + H). $^1$H NMR (400 MHz, DMSO-d6) δ 8.61 (d, J = 6.0 Hz, 1H), 8.47 (d, J = 2.9 Hz, 1H), 7.27 (dd, J = 8.5, 5.6 Hz, 2H), 7.17-7.10 (m, 2H), 6.53 (dd, J = 6.1, 3.0 Hz, 1H), 4.89 (s, 2H), 4.38 (d, J = 9.5 Hz, 2H), 4.22-4.11 (m, 1H), 4.20 (d, J = 9.4 Hz, 2H), 4.03 (s, 2H), 1.77-1.68 (m, 2H), 1.64-1.51 (m, 4H), 1.39-1.27 (m, 1H), 1.01 (qd, J = 12.4, 11.8, 5.3 Hz, 2H), 0.87 (d, J = 6.5 Hz, 3H). |
| 20 | 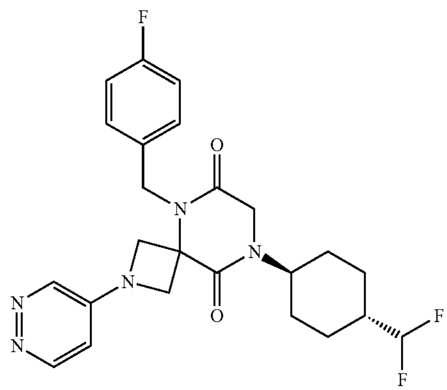 [SMILES: O=C1CN([C@H]2CC[C@H](C(F)F)CC2)C(=O)C2(CN(c3ccnnc3)C2)N1Cc1ccc(F)cc1] | 8-((1r,4r)-4-(difluoromethyl)cyclohexyl)-5-(4-fluorobenzyl)-2-(pyridazin-4-yl)-2,5,8-triazaspiro[3.5]nonane-6,9-dione. LRMS (ES) m/z 474.2 (M + H). $^1$H NMR (400 MHz, DMSO-d6) δ 8.61 (dd, J = 6.1, 0.9 Hz, 1H), 8.47 (dd, J = 3.1, 1.0 Hz, 1H), 7.30-7.24 (m, 2H), 7.17-7.10 (m, 2H), 6.53 (dd, J = 6.1, 3.1 Hz, 1H), 5.87 (td, J = 57.2, 4.3 Hz, 1H), 4.89 (s, 2H), 4.38 (d, J = 9.5 Hz, 2H), 4.22-4.12 (m, 1H), 4.20 (d, J = 9.4 Hz, 2H), 4.05 (s, 2H), 1.87-1.56 (m, 7H), 1.30-1.18 (qd, J = 12.5, 3.2 Hz, 2H). |

Example 4

Synthesis of 5-(3,4-difluorobenzyl)-8-((1r,4r)-4-methylcyclohexyl)-2-(pyridazin-3-yl)-2,5,8-triazaspiro[3.5]nonane-6,9-dione Compound 12

Step 1: Synthesis of tert-butyl 3-cyano-3-((3,4-difluorobenzyl)amino)azetidine-1-carboxylate

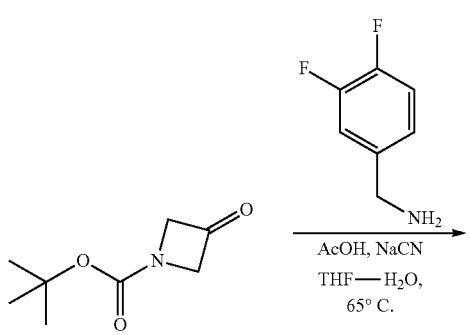

-continued

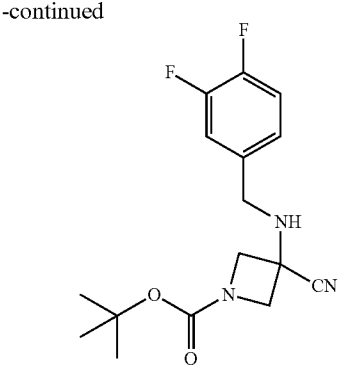

To a solution of tert-butyl 3-oxoazetidine-1-carboxylate (3.1 g, 18.2 mmol, 1.3 equiv) in THF (12.0 mL) were added acetic acid (1.0 g, 16.8 mmol, 1.2 equiv) and (3,4-difluorophenyl)methanamine (2.0 g, 14.0 mmol, 1.0 equiv) in water (6.0 mL). After stirring at r.t. for 5 minutes, to the mixture was added a solution of sodium cyanide (5.7 g, 116.9 mmol, 1.0 equiv) in water (2.8 mL). The mixture was heated at 60° C. for 15 h in an oil bath, cooled to rt, neutralized by addition of a saturated aqueous solution of sodium bicarbonate, and extracted with ethyl acetate (30.0 mL×2). The combined organic layers were washed with brine, dried over magnesium sulfate, and concentrated under reduced pressure. To the resulting yellow solid was added diethyl ether (30.0 mL), sonicated for 1 minute, cooled to 0° C., and filtered. The resulting white precipitate was washed with ice cold diethyl ether (15.0 mL) and dried overnight to provide 3.4 g (76%)

of tert-butyl 3-cyano-3-((3,4-difluorobenzyl)amino)azetidine-1-carboxylate. LRMS (ES) m/z 297.1 (M+H−27).

Step 2: Synthesis of tert-butyl 3-(2-chloro-N-(3,4-difluorobenzyl)acetamido)-3-cyanoazetidine-1-carboxylate

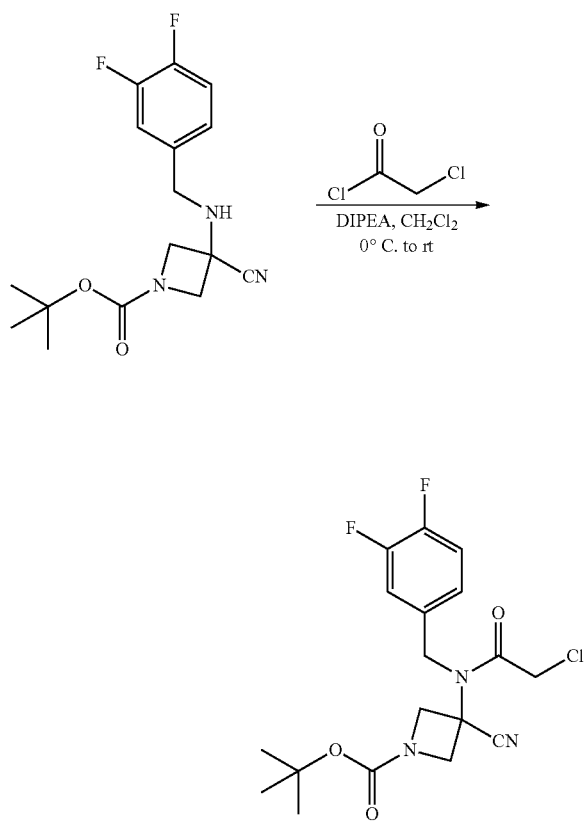

To a solution of tert-butyl 3-cyano-3-((3,4-difluorobenzyl)amino)azetidine-1-carboxylate (3.1 g, 9.7 mmol, 1.0 equiv) and N,N-diisopropylethylamine (5.0 mL, 29.0 mmol, 3.0 equiv) in DCM (125.0 mL) cooled to 0° C. was added chloroacetyl chloride (1.9 mL, 24.2 mmol, 2.5 equiv) dropwise over 20 minutes. The mixture was stirred at 0° C. for 15 min, warmed to rt, and stirred for 2 hours, diluted with saturated sodium bicarbonate, and extracted with DCM. The combined organic layers were dried over sodium sulfate, concentrated, and purified by silica gel column chromatography (0%-40% EtOAc/hexanes gradient) to provide 3.3 g (86%) of tert-butyl 3-(2-chloro-N-(3,4-difluorobenzyl)acetamido)-3-cyanoazetidine-1-carboxylate. LRMS (ES) m/z 400.1 (M+H).

Step 3: Synthesis of tert-butyl 3-cyano-3-(N-(3,4-difluorobenzyl)-2-(((1r,4r)-4-methylcyclohexyl)amino)acetamido)azetidine-1-carboxylate

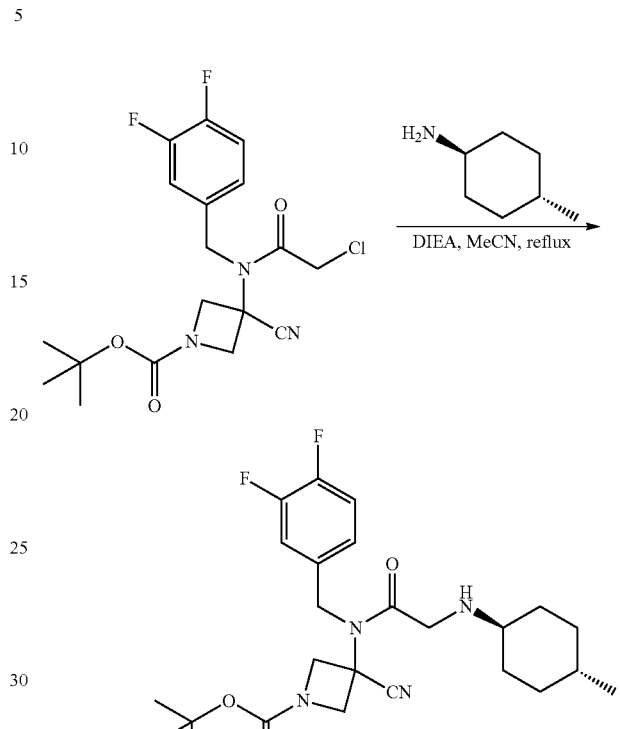

To a solution of tert-butyl 3-(2-chloro-N-(3,4-difluorobenzyl)acetamido)-3-cyanoazetidine-1-carboxylate (1.5 g, 3.8 mmol, 1.0 equiv) in acetonitrile (15.0 mL) were added (1r,4r)-4-methylcyclohexan-1-amine (641.6 mg, 5.7 mmol, 1.5 equiv) and DIPEA (2.0 mL, 11.3 mmol, 3.0 equiv). The solution was heated at 75° C. for 2 hours, concentrated and purified by silica gel chromatography using a gradient of 30 to 100% EtOAc in hexanes as eluent to provide 1.3 g (70%) of tert-butyl 3-cyano-3-(N-(3,4-difluorobenzyl)-2-(((1r,4r)-4-methylcyclohexyl)amino)acetamido)azetidine-1-carboxylate. LRMS (ES) m/z 477.3 (M+H).

Step 4: Synthesis of tert-butyl 5-(3,4-difluorobenzyl)-8-((1r,4r)-4-methylcyclohexyl)-6,9-dioxo-2,5,8-triazaspiro[3.5]nonane-2-carboxylate

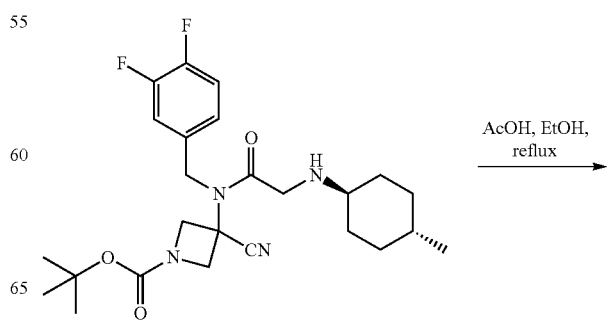

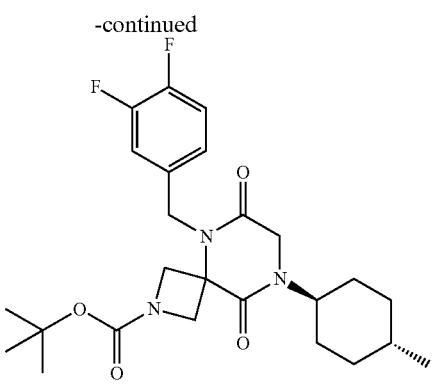

To a solution of tert-butyl 3-cyano-3-(N-(3,4-difluorobenzyl)-2-(((1r,4r)-4-methylcyclohexyl)amino)acetamido)azetidine-1-carboxylate (1.3 g, 2.6 mmol, 1.0 equiv) in ethanol (15.0 mL) was added acetic acid (2.3 mL, 40.0 mmol, 15.0 equiv). The reaction was heated at 75° C. for 15 h, then 90° C. for 3 h, cooled to rt, and sonicated for 10 minutes. The precipitates were collected by filtration, washed with ice cold ethanol, and dried to afford 953.9 mg (76%) of tert-butyl 5-(3,4-difluorobenzyl)-8-((1r,4r)-4-methylcyclohexyl)-6,9-dioxo-2,5,8-triazaspiro[3.5]nonane-2-carboxylate. LRMS (ES) m/z 422.2 (M+H−56).

Step 5: Synthesis of 5-(3,4-difluorobenzyl)-8-((1r,4r)-4-methylcyclohexyl)-2,5,8-triazaspiro[3.5]nonane-6,9-dione 2,2,2-trifluoroacetate

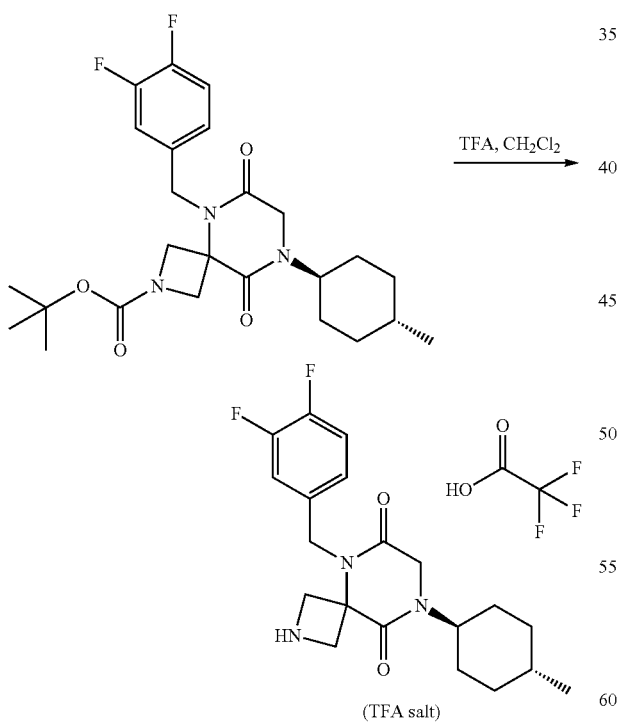

To a solution of tert-butyl 5-(3,4-difluorobenzyl)-8-((1r,4r)-4-methylcyclohexyl)-6,9-dioxo-2,5,8-triazaspiro[3.5]nonane-2-carboxylate (953.9 mg, 2.0 mmol, 1.0 equiv) in DCM (2.0 mL) was added TFA (2.0 mL) at r.t. The mixture was stirred for 30 minutes, concentrated, and dried under high vacuum to afford 981.0 mg (99%) of 5-(3,4-difluorobenzyl)-8-((1r,4r)-4-methylcyclohexyl)-2,5,8-triazaspiro[3.5]nonane-6,9-dione 2,2,2-trifluoroacetate. LRMS (ES) m/z 378.20 (M+H).

Step 6: Synthesis of 5-(3,4-difluorobenzyl)-8-((1r,4r)-4-methylcyclohexyl)-2-(pyridazin-3-yl)-2,5,8-triazaspiro[3.5]nonane-6,9-dione (Compound 12)

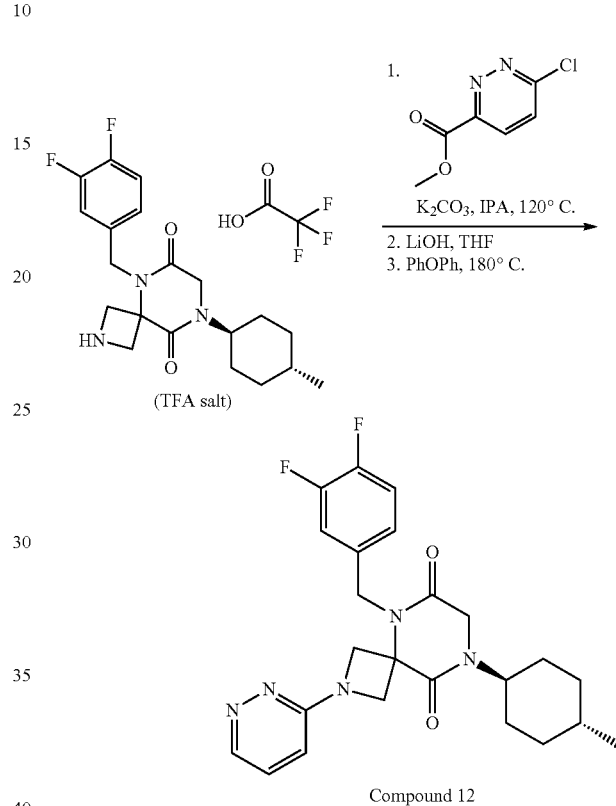

To a solution of 5-(3,4-difluorobenzyl)-8-((1r,4r)-4-methylcyclohexyl)-2,5,8-triazaspiro[3.5]nonane-6,9-dione 2,2,2-trifluoroacetate (302.8 mg, 0.62 mmol, 1.0 equiv) in IPA (4.0 mL) were added potassium carbonate (171.5 mg, 1.2 mmol, 2.0 equiv) and methyl 6-chloropyridazine-3-carboxylate (159.5 mg, 0.92 mmol, 1.5 equiv). The reaction vial was capped, heated at 120° C. for 30 min, and cooled to r.t. To the mixture was added LiOH solution (1 M, 1.8 mL, 1.8 mmol, 3.0 equiv) and the mixture was stirred for 10 minutes, diluted with water, acidified with HCl (1.0 M) to pH 3, and extracted with DCM. The combined organic layers were dried over sodium sulfate and concentrated. To the resulting solid was added diphenyl ether (4.0 mL) and the mixture was heated at 180° C. for 5 min, cooled to rt, and purified by silica gel column chromatography using a gradient of 0 to 10% MeOH in DCM to provide 75.1 mg (27%) of 5-(3,4-difluorobenzyl)-8-((1r,4r)-4-methylcyclohexyl)-2-(pyridazin-3-yl)-2,5,8-triazaspiro[3.5]nonane-6,9-dione. LRMS (ES) m/z 456.2 (M+H). $^1$H NMR (400 MHz, DMSO-$d_6$) δ 8.58 (dd, J=4.5, 1.3 Hz, 1H), 7.41-7.32 (m, 3H), 7.12-7.06 (m, 1H), 6.83 (dd, J=9.0, 1.4 Hz, 1H), 4.92 (s, 2H), 4.45 (d, J=9.5 Hz, 2H), 4.20-7.11 (m, 1H), 4.18 (d, J=9.5 Hz, 2H), 4.04 (s, 2H), 1.73 (d, J=13.1 Hz, 2H), 1.64-1.49 (m, 4H), 1.40-1.28 (m, 1H), 1.01 (qd, J=12.1, 4.6 Hz, 2H), 0.87 (d, J=6.5 Hz, 3H).

Compounds in the following table were prepared in a similar manner as Compound 12.

| No. | Structure | Name and Data |
|---|---|---|
| 10 | 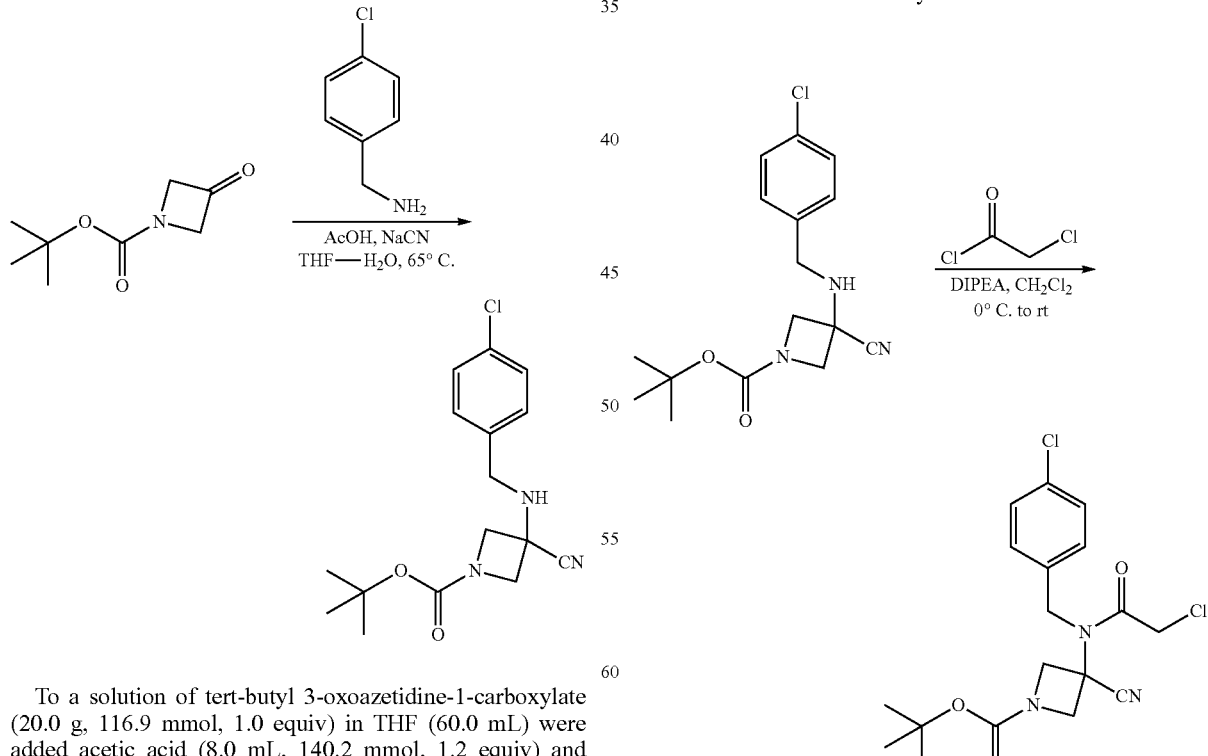 | 5-(4-chlorobenzyl)-8-((1r,4r)-4-methylcyclohexyl)-2-(pyridazin-3-yl)-2,5,8-triazaspiro[3.5]nonane-6,9-dione. LRMS (ES) m/z 454.20 (M + H). 1H NMR (400 MHz, DMSO-d6) δ 8.59 (dd, J = 4.6, 1.3 Hz, 1H), 7.41-7.33 (m, 3H), 7.26 (d, J = 8.4 Hz, 2H), 6.82 (dd, J = 9.0, 1.3 Hz, 1H), 4.93 (s, 2H), 4.45 (d, J = 9.5 Hz, 2H), 4.22-4.11 (m, 1H), 4.19 (d, J =9.7 Hz, 2H), 4.04 (s, 2H), 1.73 (d, J = 12.2 Hz, 2H), 1.63-1.51 (m, 4H), 1.40-1.28 (m, 1H), 1.01 (ddd, J = 23.9, 12.3, 4.9 Hz, 2H), 0.87 (d, J = 6.5 Hz, 3H). |

Example 5

Synthesis of 5-(4-chlorobenzyl)-8-((1r,4r)-4-methylcyclohexyl)-6,9-dioxo-2,5,8-triazaspiro[3.5]nonane-2-carboxamide Compound 18

Step 1: Synthesis of tert-butyl 3-((4-chlorobenzyl)amino)-3-cyanoazetidine-1-carboxylate To a solution of tert-butyl 3-oxoazetidine-1-carboxylate (20.0 g, 116.9 mmol, 1.0 equiv) in THF (60.0 mL) were added acetic acid (8.0 mL, 140.2 mmol, 1.2 equiv) and (4-chlorophenyl)methanamine (17.1 mL, 140.2 mmol, 1.2 equiv) in water (45.0 mL). After stirring at r.t. for 5 minutes, to the mixture was added a solution of sodium cyanide (5.7 g, 116.9 mmol, 1.0 equiv) in water (10.0 mL). The mixture was heated at 65° C. for 15 h in an oil bath, cooled to rt, neutralized by addition of a saturated aqueous solution of sodium bicarbonate, and extracted with ethyl acetate (150.0 mL×3). The combined organic layers were washed with brine, dried over sodium sulfate, filtered, and concentrated under reduced pressure. To the resulting yellow solid was added diethyl ether/hexanes (140.0 mL, 2:1) and the solution was sonicated for 5 minutes, cooled to 0° C., and filtered. The resulting white precipitate was washed with ice cold diethyl ether (50.0 mL) and dried overnight to provide 29.7 g (92%) of tert-butyl 3-((4-chlorobenzyl)amino)-3-cyanoazetidine-1-carboxylate. LRMS (ES) m/z 295.2 (M+H–27).

Step 2: Synthesis of tert-butyl 3-(2-chloro-N-(4-chlorobenzyl)acetamido)-3-cyanoazetidine-1-carboxylate To a solution of tert-butyl 3-((4-chlorobenzyl)amino)-3-cyanoazetidine-1-carboxylate (14.0 g, 43.5 mmol, 1.0 equiv)

and N,N-diisopropylethylamine (22.8 mL, 130.1 mmol, 3.0 equiv) in DCM (150.0 mL) cooled to 0° C. was added 2-chloroacetyl chloride (8.7 mL, 108.8 mmol, 2.5 equiv) in DCM (50.0 mL) dropwise over 25 minutes. The mixture was stirred at 0° C. for 15 min, warmed to rt, and stirred for 20 h. The reaction mixture was diluted with saturated sodium bicarbonate and extracted with DCM. The combined organic layers were dried over sodium sulfate, concentrated and purified by silica gel column chromatography (0%-40% EtOAc/hexanes gradient) to provide 14.1 g (81%) of tert-butyl 3-(2-chloro-N-(4-chlorobenzyl)acetamido)-3-cyano-azetidine-1-carboxylate. LRMS (ES) m/z 398.1 (M+H).

Step 3: Synthesis of tert-butyl 3-(N-(4-chlorobenzyl)-2-(((1r,4r)-4-methylcyclohexyl)amino)acetamido)-3-cyanoazetidine-1-carboxylate

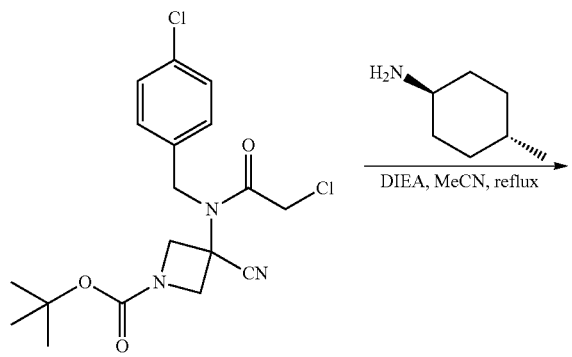

To a solution of tert-butyl tert-butyl 3-(2-chloro-N-(4-chlorobenzyl)acetamido)-3-cyanoazetidine-1-carboxylate (11.0 g, 27.6 mmol, 1 equiv) in acetonitrile (90.0 mL) were added (1r,4r)-4-methylcyclohexan-1-amine (3.6 g, 30.4 mmol, 1.0 equiv) and DIPEA (9.6 mL, 69.1 mmol, 2.5 equiv). The solution was heated at reflux temperature for 3.5 h and more (1r,4r)-4-methylcyclohexan-1-amine (362.1 mg, 3.0 mmol, 0.1 equiv) was added. The mixture was heated with stirring for 1 hour, cooled, diluted with water, and extracted with ethyl acetate. The combined organic layers were washed with brine, dried over sodium sulfate, and concentrated to provide 12.6 g (96%) of tert-butyl 3-(N-(4-chlorobenzyl)-2-(((1r,4r)-4-methylcyclohexyl)amino)acetamido)-3-cyanoazetidine-1-carboxylate. LRMS (ES) m/z 475.2 (M+H).

Step 4: Synthesis of tert-butyl 5-(4-chlorobenzyl)-8-((1r,4r)-4-methylcyclohexyl)-6,9-dioxo-2,5,8-triazaspiro[3.5]nonane-2-carboxylate

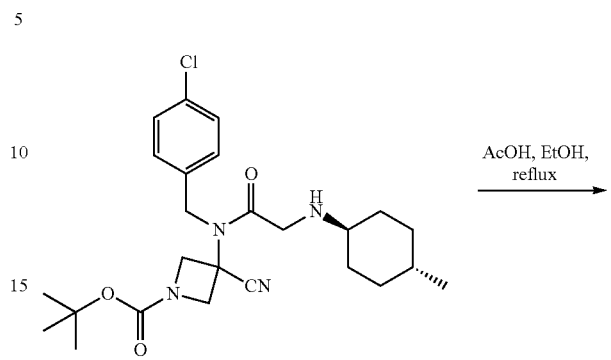

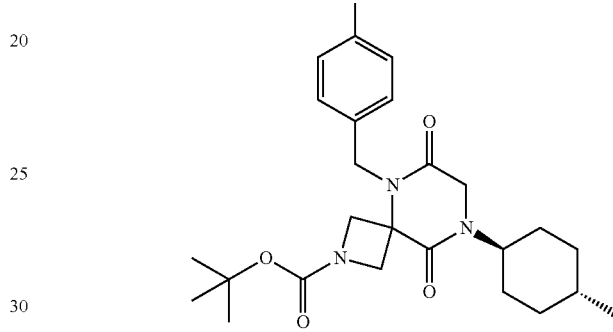

To a solution of tert-butyl 3-(N-(4-chlorobenzyl)-2-(((1r,4r)-4-methylcyclohexyl)amino)acetamido)-3-cyanoazetidine-1-carboxylate (12.6 g, 26.4 mmol, 1.0 equiv) in ethanol (88.0 mL) was added acetic acid at 0 h (15.1 mL, 264.7 mmol, 10.0 equiv), 14.5 h (7.6 mL, 132.4 mmol, 5.0 equiv), and 20.5 h (7.6 mL, 132.4 mmol, 5.0 equiv). The reaction was stirred at reflux temperature for a total of 21 h, cooled to rt, and sonicated for 10 minutes. The solid was filtered, washed with ice cold ethanol, and dried. The filtrate was concentrated, dissolved in ethanol, and sonication/filtration was repeated 3 more times (4 in total) to obtain 9.8 g (78%) of tert-butyl 5-(4-chlorobenzyl)-8-((1r,4r)-4-methylcyclohexyl)-6,9-dioxo-2,5,8-triazaspiro[3.5]nonane-2-carboxylate. LRMS (ES) m/z 420.1 (M+H−56).

Step 5: Synthesis of 5-(4-chlorobenzyl)-8-((1r,4r)-4-methylcyclohexyl)-2,5,8-triazaspiro[3.5]nonane-6,9-dione 2,2,2-trifluoroacetate

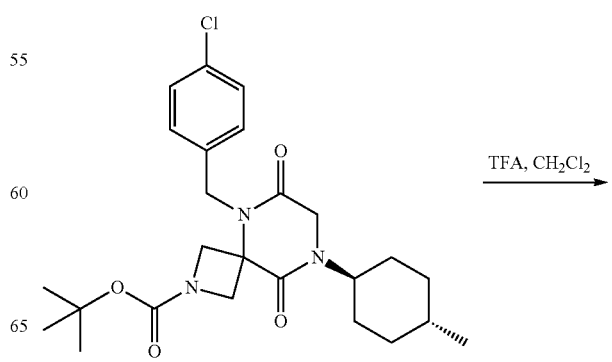

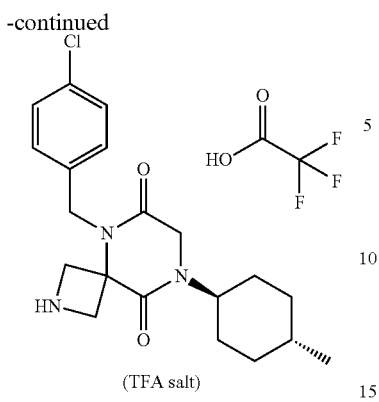

(TFA salt)

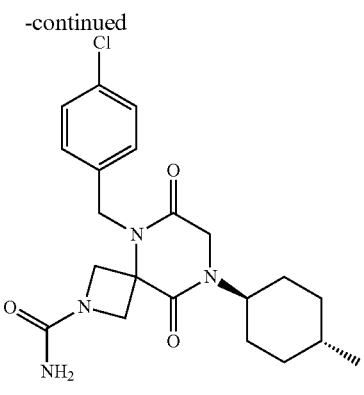

Compound 18

To a solution of tert-butyl 5-(4-chlorobenzyl)-8-((1r,4r)-4-methylcyclohexyl)-6,9-dioxo-2,5,8-triazaspiro[3.5]nonane-2-carboxylate (15.1 g, 31.8 mmol, 1.0 equiv) in DCM (55.0 mL) was added TFA (55.0 mL) at r.t. The mixture was stirred for 30 minutes, concentrated, and dried under high vacuum to afford 15.6 g (99%) of 5-(4-chlorobenzyl)-8-((1r,4r)-4-methylcyclohexyl)-2,5,8-triazaspiro[3.5]nonane-6,9-dione 2,2,2-trifluoroacetate. LRMS (ES) m/z 376.2 (M+H).

Step 6: Synthesis of 5-(4-chlorobenzyl)-8-((1r,4r)-4-methylcyclohexyl)-6,9-dioxo-2,5,8-triazaspiro[3.5]nonane-2-carboxamide (Compound 18)

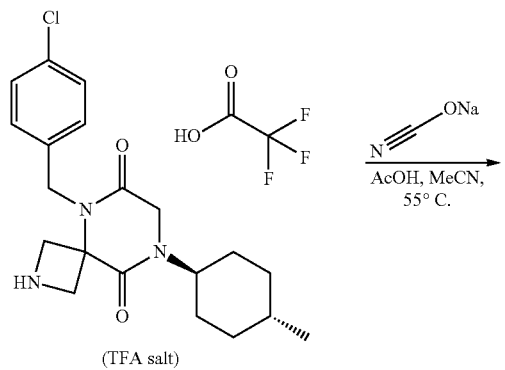

To a solution of 5-(4-chlorobenzyl)-8-((1r,4r)-4-methylcyclohexyl)-2,5,8-triazaspiro[3.5]nonane-6,9-dione 2,2,2-trifluoroacetate (15.6 g, 31.8 mmol, 1.0 equiv) in acetonitrile (102.0 mL) were added acetic acid (175.0 µL, 3.1 mmol, 0.1 equiv) and sodium cyanate (4.0 g, 61.2 mmol, 1.9 equiv). The mixture was heated at 55° C. for 80 min, cooled to rt, diluted with water and saturated sodium bicarbonate, and extracted with ethyl acetate. The combined organic layers were washed with brine, dried over sodium sulfate, and concentrated to afford precipitates which was sonicated in ether (100.0 mL). The resulting precipitates were collected by filtration, washed with ice cold ether, and dried to give a white solid, which was sonicated again in ethanol (100.0 mL). The precipitates were collected again by filtration, washed with ice cold ether, and dried to provide 8.7 g (65%) of 5-(4-chlorobenzyl)-8-((1r,4r)-4-methylcyclohexyl)-6,9-dioxo-2,5,8-triazaspiro[3.5]nonane-2-carboxamide as a white solid. LRMS (ES) m/z 419.2 (M+H). $^1$H NMR (400 MHz, DMSO-$d_6$) δ 7.39 (d, J=8.4 Hz, 2H), 7.24 (d, J=8.4 Hz, 2H), 6.01 (s, 2H), 4.82 (s, 2H), 4.22-4.12 (m, 1H), 4.19 (d, J=9.3 Hz, 2H), 3.99 (s, 2H), 3.83 (d, J=9.3 Hz, 2H), 1.77-1.69 (m, 2H), 1.63-1.48 (m, 4H), 1.41-1.27 (m, 1H), 1.03 (qd, J=12.3, 4.1 Hz, 2H), 0.87 (d, J=6.4 Hz, 3H).

Compounds in the following table were prepared in a similar manner as Compound 18.

| No. | Structure | Name and Data |
|---|---|---|
| 3 | ![structure] | 5-(4-chloro-3-fluorobenzyl)-8-((1r,4r)-4-methylcyclohexyl)-6,9-dioxo-2,5,8-triazaspiro[3.5]nonane-2-carboxamide. LRMS (ES) m/z 437.15 (M + H). $^1$H NMR (400 MHz, DMSO-d6) δ 7.55 (t, J = 8.0 Hz, 1H), 7.35 (dd, J = 10.6, 2.0 Hz, 1H), 7.11 (dd, J = 8.3, 1.5 Hz, 1H), 5.99 (s, 2H), 4.83 (s, 2H), 4.20 (d, J = 9.2 Hz, 2H), 4.17 (tt, J = 11.4, 4.7 Hz, 1H), 3.98 (s, 2H), 3.82 (d, J = 9.3 Hz, 2H), 1.73 (d, J = 12.8 Hz, 2H), 1.66-1.52 (m, 4H), 1.39-1.27 (m, 1H), 1.04 (td, J = 12.3, 4.2 Hz, 2H), 0.87 (d, J = 6.5 Hz, 3H). |

| No. | Structure | Name and Data |
|---|---|---|
| 6 | 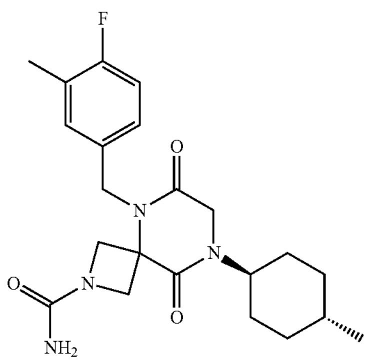 | 5-(4-fluoro-3-methylbenzyl)-8-((1r,4r)-4-methylcyclohexyl)-6,9-dioxo-2,5,8-triazaspiro[3.5]nonane-2-carboxamide. LRMS (ES) m/z 417.20 (M + H). $^1$H NMR (400 MHz, DMSO-d6) δ 7.16-7.10 (m, 1H), 7.08 (d, J = 9.3 Hz, 1H), 7.05-6.99 (m, 1H), 6.00 (s, 2H), 4.78 (s, 2H), 4.20-4.12 (m, 1H), 4.18 (d, J = 9.3 Hz, 2H), 3.98 (s, 2H), 3.86 (d, J = 9.2 Hz, 2H), 2.20 (d, J = 1.9 Hz, 3H), 1.73 (d, J = 13.0 Hz, 2H), 1.66-1.47 (m, 4H), 1.39-1.27 (m, 1H), 1.10-0.96 (m, 2H), 0.87 (d, J = 6.5 Hz, 3H). |
| 7 | 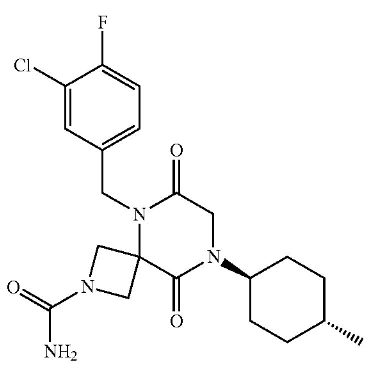 [SMILES: C[C@H]1CC[C@H](N2CC(=O)N(Cc3ccc(F)c(Cl)c3)C3(CN(C(N)=O)C3)C2=O)CC1] | 5-(3-chloro-4-fluorobenzyl)-8-((1r,4r)-4-methylcyclohexyl)-6,9-dioxo-2,5,8-triazaspiro[3.5]nonane-2-carboxamide. LRMS (ES) m/z 437.20 (M + H). $^1$H NMR (400 MHz, DMSO-d6) δ 7.50 (dd, J = 7.1, 2.2 Hz, 1H), 7.38 (t, J = 8.9 Hz, 1H), 7.23 (ddd, J = 8.5, 4.6, 2.0 Hz, 1H), 6.00 (s, 2H), 4.81 (s, 2H), 4.20 (d, J = 9.3 Hz, 2H), 4.22-4.12 (m, 1H), 3.98 (s, 2H), 3.83 (d, J = 9.3 Hz, 2H), 1.73 (d, J = 12.8 Hz, 2H), 1.63-1.49 (m, 4H), 1.39-1.28 (m, 1H), 1.04 (ddd, J = 12.8, 8.5, 3.9 Hz, 2H), 0.87 (d, J = 6.5 Hz, 3H). |
| 11 | 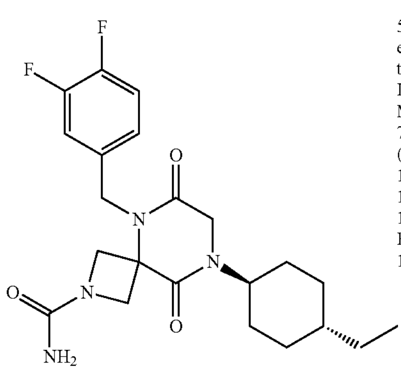 | 5-(3,4-difluorobenzyl)-8-((1r,4r)-4-ethylcyclohexyl)-6,9-dioxo-2,5,8-triazaspiro[3.5]nonane-2-carboxamide. LRMS (ES) m/z 435.20 (M + H). $^1$H NMR (400 MHz, DMSO-d6) δ 7.48-7.31 (m, 2H), 7.10-7.04 (m, 1H), 6.00 (s, 2H), 4.81 (s, 2H), 4.20 (d, J = 9.3 Hz, 2H), 4.18 (tt, J = 12.2, 3.7 Hz, 1H), 3.98 (s, 2H), 3.82 (d, J = 9.3 Hz, 2H), 1.80 (d, J = 12.5 Hz, 2H), 1.67-1.58 (m, 4H), 1.52 (qd, J = 12.3, 2.7 Hz, 2H), 1.21 (p, J = 7.0 Hz, 2H), 1.15-1.05 (m, 1H), 0.99 (qd, J = 11.0, 2.8 Hz, 2H), 0.86 (t, J = 7.3 Hz, 3H). |

Example 6
Synthesis of 5-(4-chlorobenzyl)-8-(2,4-difluorophenyl)-6,9-dioxo-2,5,8-triazaspiro[3.5]nonane-2-carbaldehyde
Comparator A
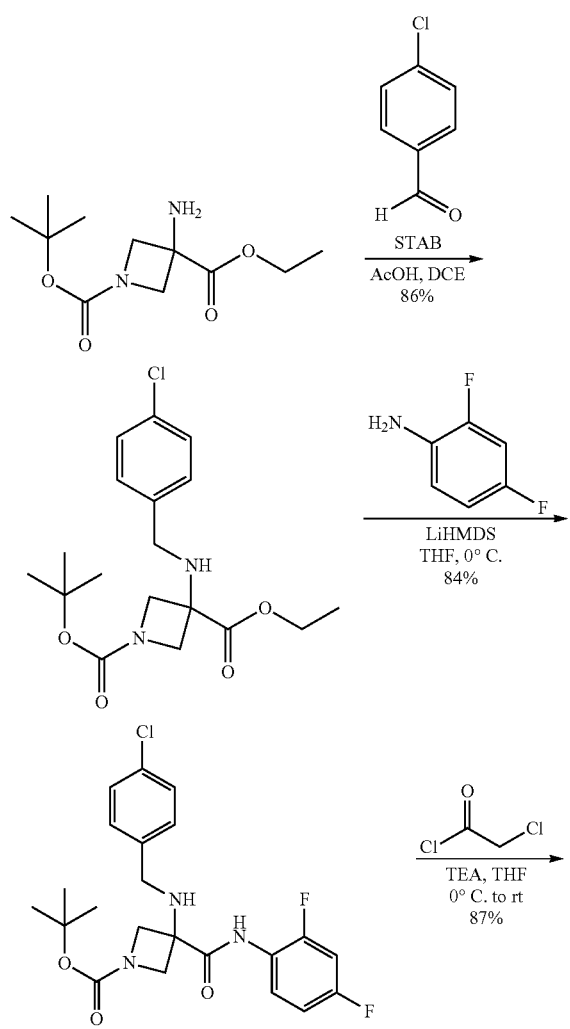
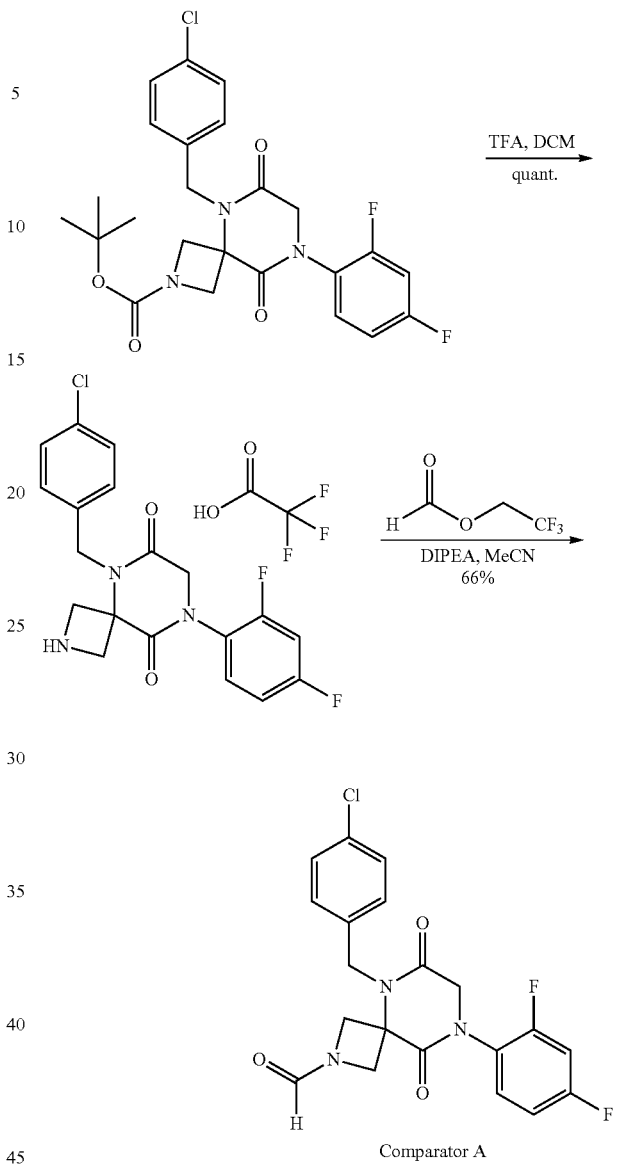
Step 1: Synthesis of 1-(tert-butyl) 3-ethyl 3-((4-chlorobenzyl)amino)azetidine-1,3-dicarboxylate
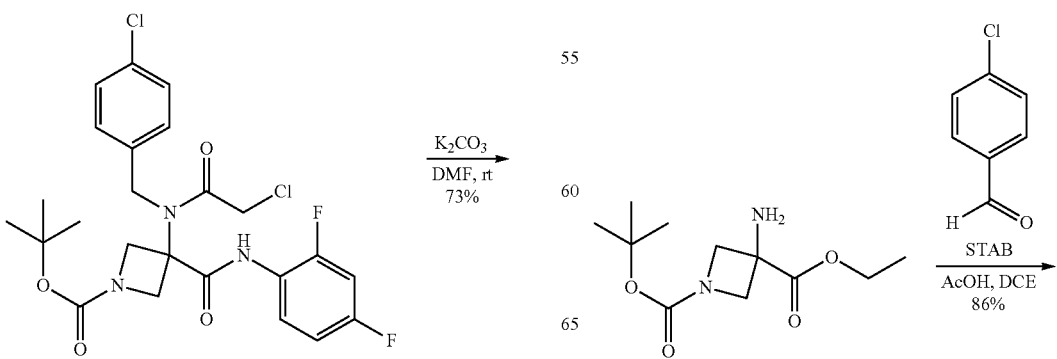

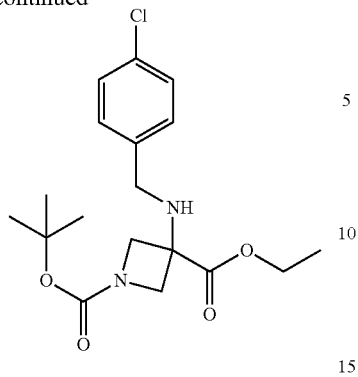

To a solution of 1-tert-butyl 3-ethyl 3-aminoazetidine-1,3-dicarboxylate (10.6 g, 43.3 mmol, 1.0 equiv) and 4-chlorobenzaldehyde (6.1 g, 43.3 mmol, 1.0 equiv) in DCE (120.0 mL) at 0° C. were added AcOH (5.0 mL). Upon warming to r.t. and stirred at rt, to the mixture was added additional AcOH (5.0 mL) twice at 4 h, 8.5 h, and 9 h (total of 20.0 mL). To this mixture was added STAB (11.0 g, 52.0 mmol, 1.2 equiv.). The mixture was stirred at r.t. overnight, diluted with aqueous sodium bicarbonate, and extracted with DCM three times. The combined organic layers were dried over sodium sulfate and concentrated. The obtained oil was dissolved in warmed hexanes and EA (dropwise until the mixture went into homogeneous solution) at 60° C. with stirring. The mixture was then cooled to 0° C. and precipitation was collected by filtration and washed with cold hexanes. The filtrate was concentrated and repeated the process again. The combined solid was dried under vacuum to afford 13.8 g (86%) of 1-(tert-butyl) 3-ethyl 3-((4-chlorobenzyl)amino)azetidine-1,3-dicarboxylate as a white solid. LRMS (ES) m/z 313.1 (M+H−56).

Step 2: Synthesis of tert-butyl 3-((4-chlorobenzyl)amino)-3-((2,4-difluorophenyl)carbamoyl)azetidine-1-carboxylate

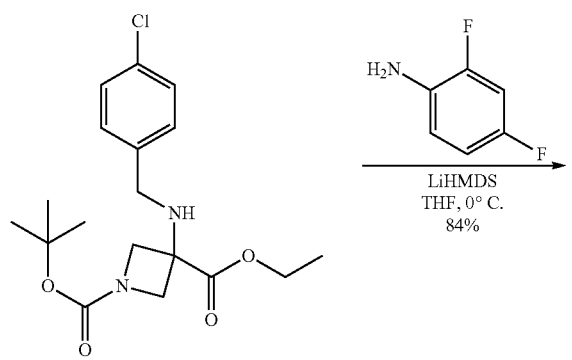

To a stirred solution of 1-(tert-butyl) 3-ethyl 3-((4-chlorobenzyl)amino)azetidine-1,3-dicarboxylate (10.0 g, 27.1 mmol, 1.0 equiv) and 2,4-difluoroaniline (3.0 mL, 29.8 mmol, 1.1 equiv.) in THF (200.0 mL) at 0° C. under $N_2$ were added a solution of LHMDS (54.2 mL, 1 M in THF, 54.2 mmol, 2.0 equiv) dropwise over a period of 20 min. The mixture was stirred at 0° C. for 20 min, quenched with water (50 mL), acidified to pH 5 using aqueous HCl (0.5 N), and extracted with EA (100 mL) twice. The combined organic layer were washed with brine, dried over sodium sulfate, concentrated to afford 11.3 g of tert-butyl 3-((4-chlorobenzyl)amino)-3-((2,4-difluorophenyl)carbamoyl)azetidine-1-carboxylate, which was used for next step without purification. LRMS (ES) m/z 396.1 (M+H−56).

Step 3: Synthesis of tert-butyl 3-(2-chloro-N-(4-chlorobenzyl)acetamido)-3-((2,4-difluorophenyl)carbamoyl)azetidine-1-carboxylate

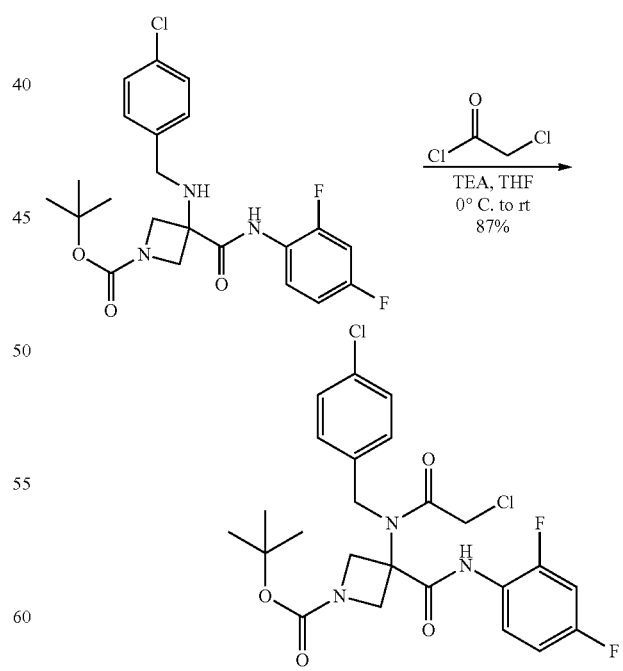

To a solution of tert-butyl 3-((4-chlorobenzyl)amino)-3-((2,4-difluorophenyl)carbamoyl)azetidine-1-carboxylate (11.3 g, 23.2 mmol, 1.0 equiv) in THF (20 mL) cooled to 0° C. were added TEA (4.8 mL, 34.7 mmol, 1.5 equiv) and 2-chloroacetyl chloride (1.5 mL, 27.8 mmol, 1.2 equiv). Upon stirring at 0° C. for 30 min, additional TEA (4.8 mL, 34.7 mmol, 1.5 equiv) and 2-chloroacetyl chloride (1.8 mL, 23.2 mmol, 1.0 equiv) were added into the mixture and the mixture was stirred at 0° C. for 30 min. To this mixture was added additional 2-chloroacetyl chloride (0.6 mL, 6.9 mmol, 0.3 equiv). The mixture was gradually warmed to rt, stirred for 45 min, cooled to 0° C., and quenched with aqueous sodium bicarbonate. The mixture was extracted with EA three times. The combined organic layers were washed with bring, dried over sodium sulfate, and concentrated to afford 13.2 g of tert-butyl 3-(2-chloro-N-(4-(trifluoromethyl)benzyl)acetamido)-3-((2,4-difluorophenyl)carbamoyl)azetidine-1-carboxylate, which was used for next step without further purification. LRMS (ES) m/z 528.1 (M+H).

Step 4: Synthesis of tert-butyl 5-(4-chlorobenzyl)-8-(2,4-difluorophenyl)-6,9-dioxo-2,5,8-triazaspiro[3.5]nonane-2-carboxylate

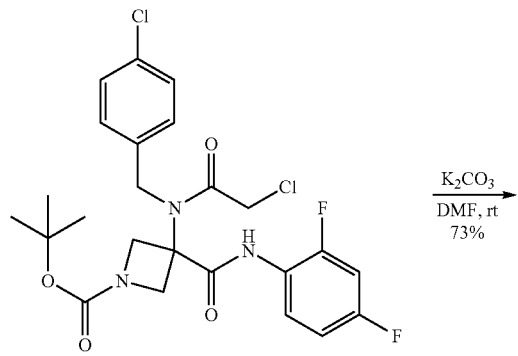

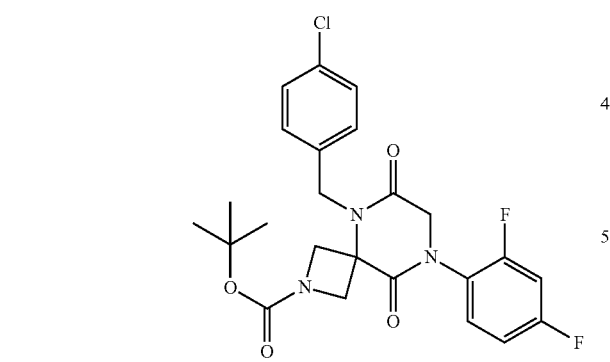

To a stirred solution of tert-butyl 3-(2-chloro-N-(4-(trifluoromethyl)benzyl)acetamido)-3-((2,4-difluorophenyl)carbamoyl)azetidine-1-carboxylate (13.2 g, 20.1 mmol, 1.0 equiv) in DMF (40.0 mL) under N₂ was added K₂CO₃ (4.2 g, 30.1 mmol, 1.5 equiv.). The resulting mixture was stirred at r.t. for 3.5 h, diluted with water, and extracted with EA twice. The combined organic layers were washed with water twice and brine once, dried over sodium sulfate, and concentrated to afford 11.7 g of tert-butyl 5-(4-chlorobenzyl)-8-(2,4-difluorophenyl)-6,9-dioxo-2,5,8-triazaspiro[3.5]nonane-2-carboxylate. LRMS (ES) m/z 436.1 (M+H−56).

Step 5: Synthesis of 5-(4-chlorobenzyl)-8-(2,4-difluorophenyl)-2,5,8-triazaspiro[3.5]nonane-6,9-dione 2,2,2-trifluoroacetate

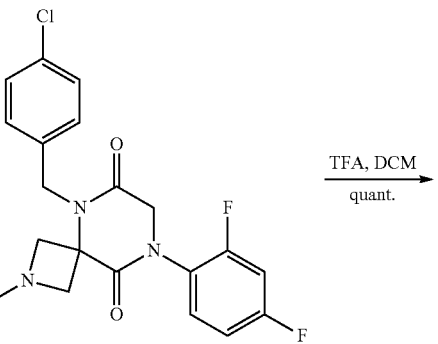

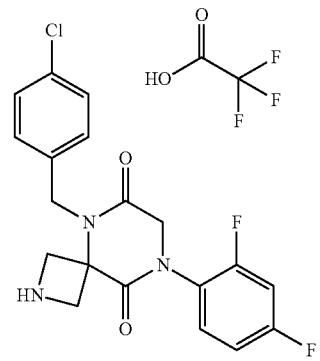

To a stirred solution of tert-butyl 5-(4-chlorobenzyl)-8-(2,4-difluorophenyl)-6,9-dioxo-2,5,8-triazaspiro[3.5]nonane-2-carboxylate (14.7 g, 29.8 mmol, 1.0 equiv) in DCM (50.0 mL) was added TFA (25.0 mL). The resulting mixture was stirred at r.t. for 3 h and concentrated to dryness to afford 15.1 g of 5-(4-chlorobenzyl)-8-(2,4-difluorophenyl)-2,5,8-triazaspiro[3.5]nonane-6,9-dione 2,2,2-trifluoroacetate, which was used for next step without further purification. LRMS (ES) m/z 392.1 (M+H).

Step 6: Synthesis of 5-(4-chlorobenzyl)-8-(2,4-difluorophenyl)-6,9-dioxo-2,5,8-triazaspiro[3.5]nonane-2-carbaldehyde

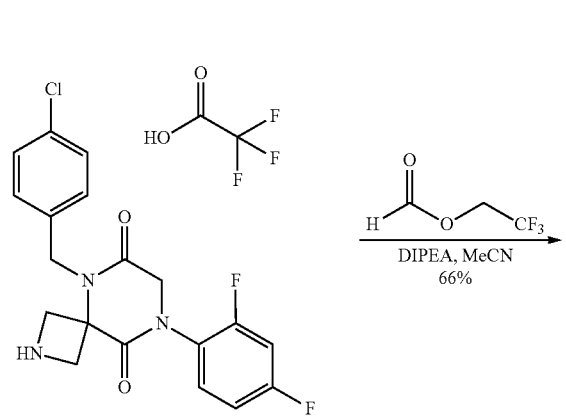

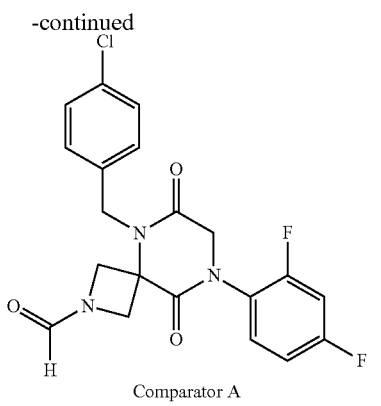

Comparator A

To a solution of 5-(4-chlorobenzyl)-8-(2,4-difluorophenyl)-2,5,8-triazaspiro[3.5]nonane-6,9-dione 2,2,2-trifluoroacetate (15.1 g, 29.9 mmol, 1 equiv) and N,N-diisopropylethylamine (15.7 mL, 89.7 mmol, 3 equiv) in ACN (50 mL) was added 2,2,2-trifluoroethyl formate (5.8 mL, 59.8 mmol, 2 equiv). The reaction was stirred at r.t. for 1 hour, diluted with water, and extracted with DCM. The combined organic layers were dried over sodium sulfate, concentrated, and purified by silica gel chromatography using 0 to 100% EtOAc gradient, then 0-10% MeOH, DCM gradient. The solid was suspended in EtOH/MTBE 1:1, heated to 80° C., cooled on ice, filtered, washed with MTBE, and dried to afford 8.3 g (66%) of 5-(4-chlorobenzyl)-8-(2,4-difluorophenyl)-6,9-dioxo-2,5,8-triazaspiro[3.5]nonane-2-carbaldehyde LRMS (ES) m/z 420.1 (M+H). $^1$H NMR (400 MHz, DMSO-$d_6$) δ 7.98 (s, 1H), 7.65 (td, J=8.8, 6.0 Hz, 1H), 7.48-7.41 (m, 1H), 7.43 (d, J=8.5 Hz, 2H), 7.34 (d, J=8.4 Hz, 2H), 7.22 (td, J=8.4, 2.4 Hz, 1H), 4.91 (s, 2H), 4.55 (d, J=9.7 Hz, 1H), 4.43 (d, J=1.6 Hz, 2H), 4.37 (d, J=9.8 Hz, 1H), 4.28 (d, J=10.8 Hz, 1H), 4.08 (d, J=10.8 Hz, 1H).

Example 7

Synthesis of 8-(2,4-difluorophenyl)-6,9-dioxo-5-(4-(trifluoromethyl)benzyl)-2,5,8-triazaspiro[3.5]nonane-2-carbaldehyde Comparator B

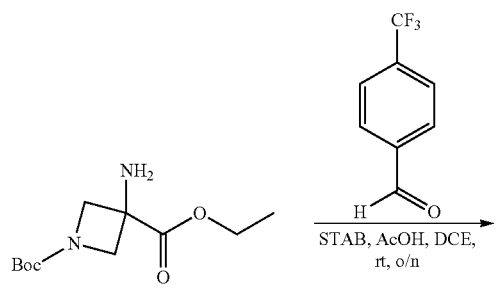

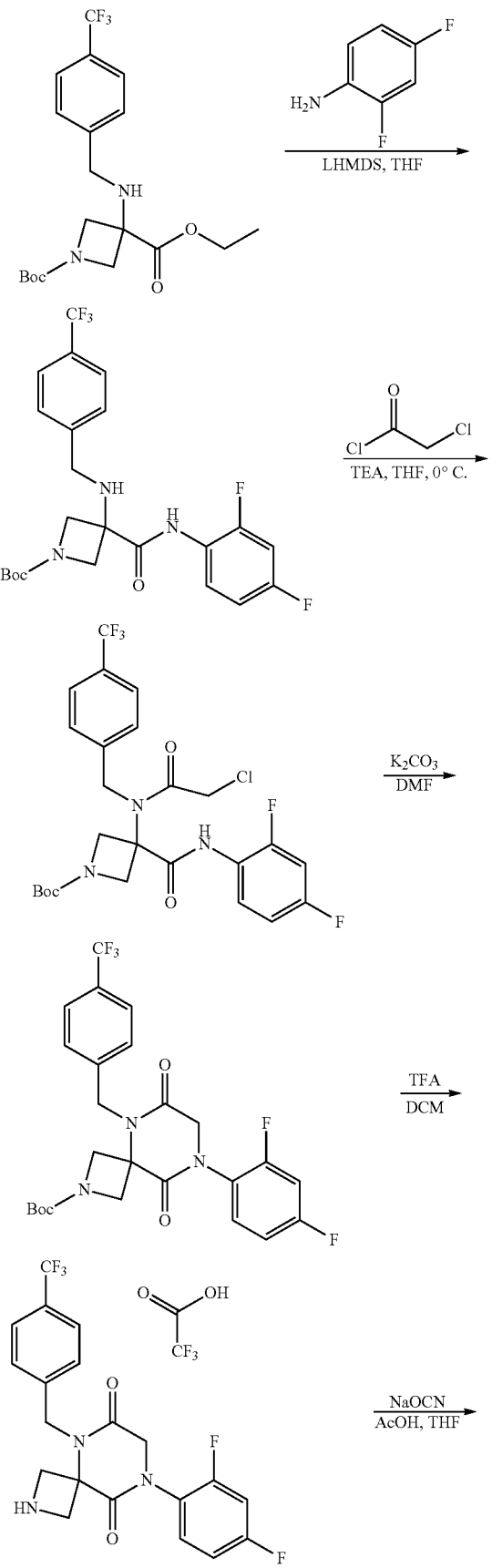

87

-continued

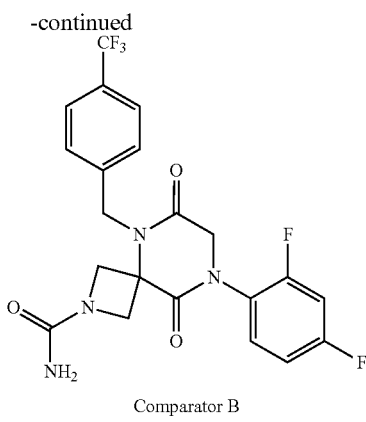

Comparator B

Synthesis of 1-(tert-butyl) 3-ethyl 3-((4-(trifluoromethyl)benzyl)amino)azetidine-1,3-dicarboxylate

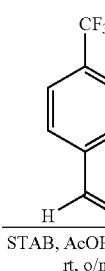
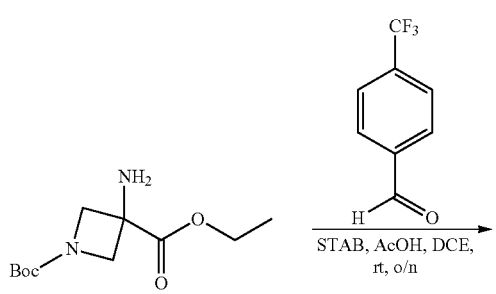

To a solution of 1-tert-butyl 3-ethyl 3-aminoazetidine-1,3-dicarboxylate (15.0 g, 61.4 mmol, 1.0 equiv) and 4-(trifluoromethyl)benzaldehyde (11.8 g, 67.5 mmol, 1.1 equiv) in DCE (60.0 mL) at 0° C. were added AcOH (7.4 g, 122.8 mmol, 2.0 equiv.) and STAB (19.5 g, 92.1 mmol, 1.5 equiv) in portions. The resulting mixture was stirred at r.t. overnight, adjusted the pH to 8 with ammonium hydroxide, added water (100.0 mL) and extracted twice with DCM (300.0 mL). The combined organic layers were washed with brine twice, dried over anhydrous Na$_2$SO$_4$, and concentrated under reduced pressure to afford 29.6 g of 1-(tert-butyl) 3-ethyl 3-((4-(trifluoromethyl)benzyl)amino)azetidine-1,3-dicarboxylate, which was sued for next step without purification. LRMS (ES) m/z 347.1 (M+H−56)

88

Synthesis of tert-butyl 3-((2,4-difluorophenyl)carbamoyl)-3-((4-(trifluoromethyl)benzyl)amino)azetidine-1-carboxylate

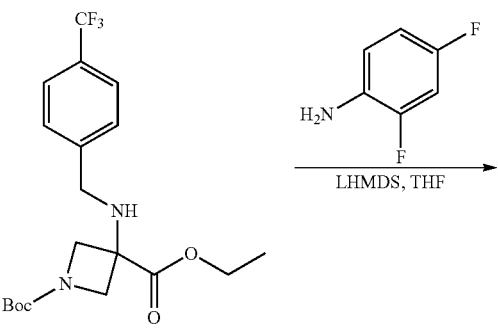

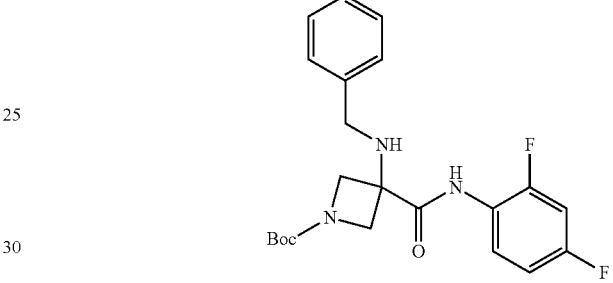

To a stirred solution of 1-(tert-butyl) 3-ethyl 3-((4-(trifluoromethyl)benzyl)amino)azetidine-1,3-dicarboxylate (29.6 g, 44.1 mmol, 1.0 equiv) and 2,4-difluoroaniline (4.9 mL, 48.5 mmol, 1.1 equiv.) in THF (200.0 mL) at 0° C. under N$_2$ were added a solution of LHMDS (88.3 mL, 1 M in THF, 88.3 mmol, 2.0 equiv) dropwise over a period of 20 min. The mixture was stirred at 0° C. for 20 min, quenched with water (50 mL, acidified to pH 5 using aqueous HCl (3N), and extracted with EA (100 mL) twice. The combined organic layer were washed with brine, dried over sodium sulfate, concentrated to afford 36.2 g of tert-butyl 3-((2,4-difluorophenyl)carbamoyl)-3-((4-(trifluoromethyl)benzyl)amino)azetidine-1-carboxylate, which was used for next step without purification. LRMS (ES) m/z 430.1 (M+H−56).

Synthesis of tert-butyl 3-(2-chloro-N-(4-(trifluoromethyl)benzyl)acetamido)-3-((2,4-difluorophenyl)carbamoyl)azetidine-1-carboxylate

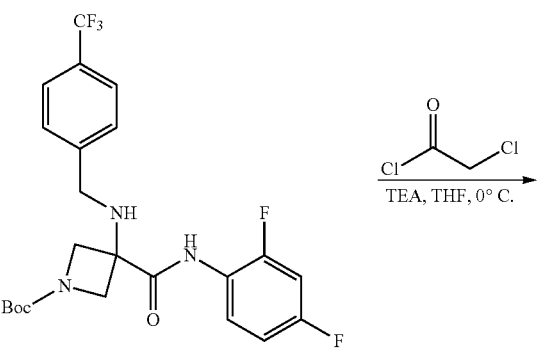

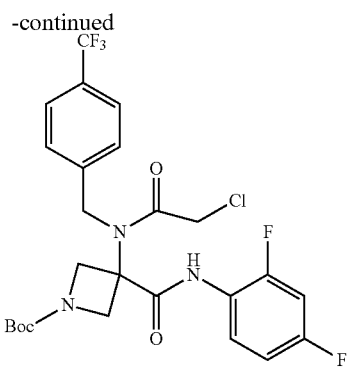

To a solution of tert-butyl 3-((2,4-difluorophenyl)carbamoyl)-3-((4-(trifluoromethyl)benzyl)amino)azetidine-1-carboxylate (36.2 g, 40.6 mmol, 1.0 equiv) in THF (100 mL) cooled to 0° C. were added TEA (8.5 mL, 60.9 mmol, 1.5 equiv) and 2-chloroacetyl chloride (3.9 mL, 48.7 mmol, 1.2 equiv). Upon stirring at 0° C. for 30 min, additional TEA (8.5 mL, 60.9 mmol, 1.5 equiv) and 2-chloroacetyl chloride (3.3 mL, 40.6 mmol, 1.0 equiv) were added into the mixture and the mixture was stirred at 0° C. for 30 min. To this mixture was added additional 2-chloroacetyl chloride (1.0 mL, 12.2 mmol, 0.3 equiv). The mixture was gradually warmed to rt, stirred for 45 min, cooled to 0° C., and quenched with aqueous sodium bicarbonate. The mixture was extracted with EA three times. The combined organic layers were washed with bring, dried over sodium sulfate, and concentrated to afford 42.0 g of tert-butyl 3-(2-chloro-N-(4-(trifluoromethyl)benzyl)acetamido)-3-((2,4-difluorophenyl)carbamoyl)azetidine-1-carboxylate, which was used for next step without further purification. LRMS (ES) m/z 562.1 (M+H).

Synthesis of tert-butyl 8-(2,4-difluorophenyl)-6,9-dioxo-5-(4-(trifluoromethyl)benzyl)-2,5,8-triazaspiro[3.5]nonane-2-carboxylate

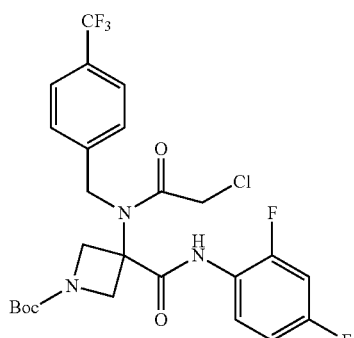

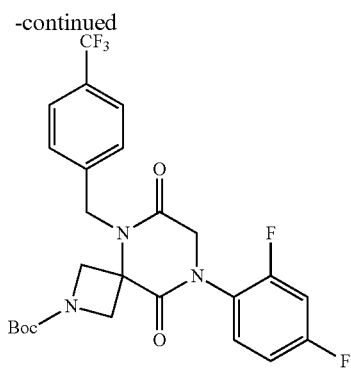

To a stirred solution of tert-butyl 3-(2-chloro-N-(4-(trifluoromethyl)benzyl)acetamido)-3-((2,4-difluorophenyl)carbamoyl)azetidine-1-carboxylate (42.0 g, 33.4 mmol, 1.0 equiv) in DMF (80.0 mL) under $N_2$ was added $K_2CO_3$ (7.0 g, 50.1 mmol, 1.5 equiv.). The resulting mixture was stirred at r.t. for 3.5 h, diluted with water, and extracted with EA twice. The combined organic layers were washed with water twice and brine once, dried over sodium sulfate, concentrated, and purified by silica gel using a gradient of 0-60% EA in hexanes as eluent to afford 12.0 g (37% over 4 steps) of tert-butyl 8-(2,4-difluorophenyl)-6,9-dioxo-5-(4-(trifluoromethyl)benzyl)-2,5,8-triazaspiro[3.5]nonane-2-carboxylate. LRMS (ES) m/z 469.7 (M+H−56).

Synthesis of 8-(2,4-difluorophenyl)-5-(4-(trifluoromethyl)benzyl)-2,5,8-triazaspiro[3.5]nonane-6,9-dione 2,2,2-trifluoroacetate

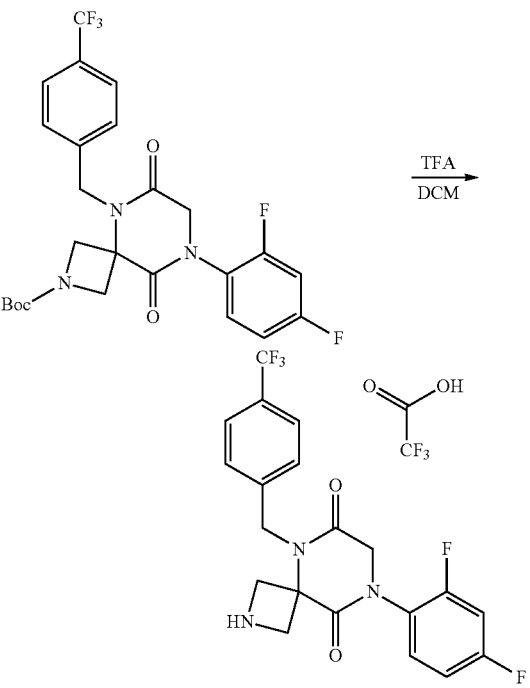

To a stirred solution of tert-butyl 8-(2,4-difluorophenyl)-6,9-dioxo-5-(4-(trifluoromethyl)benzyl)-2,5,8-triazaspiro[3.5]nonane-2-carboxylate (12.0 g, 22.8 mmol, 1.0 equiv) in DCM (12.0 mL) was added TFA (40.0 mL). The resulting mixture was stirred at r.t. for 3 h and concentrated to dryness to afford 12.3 g of 8-(2,4-difluorophenyl)-5-(4-(trifluoromethyl)benzyl)-2,5,8-triazaspiro[3.5]nonane-6,9-dione 2,2,2-trifluoroacetate, which was used for next step without further purification. LRMS (ES) m/z 426.1 (M+H).

Synthesis of 8-(2,4-difluorophenyl)-6,9-dioxo-5-(4-(trifluoromethyl)benzyl)-2,5,8-triazaspiro[3.5]nonane-2-carbaldehyde

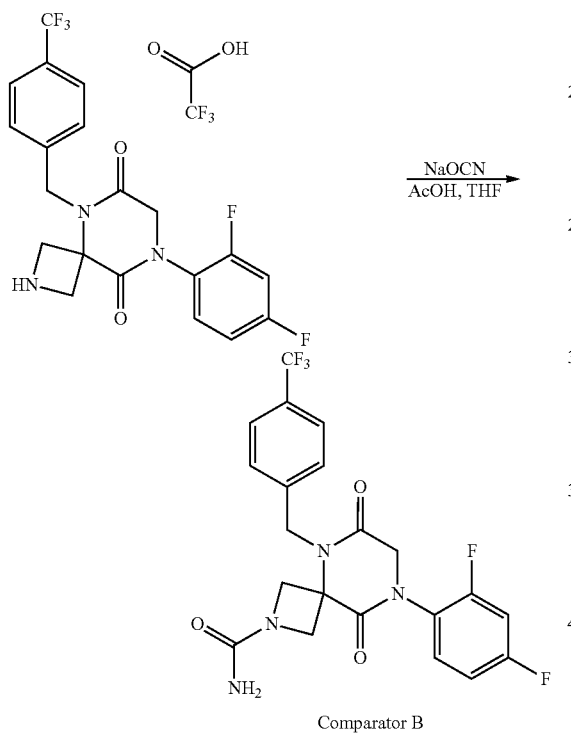

Comparator B

To a stirred solution of 8-(2,4-difluorophenyl)-5-(4-(trifluoromethyl)benzyl)-2,5,8-triazaspiro[3.5]nonane-6,9-dione 2,2,2-trifluoroacete (12.3 g, 22.8 mmol, 1.0 equiv) in THF (50.0 mL) were added sodium cyanate (4.4 g, 68.4 mmol, 3.0 equiv.) and a few drops of acetic acid. The mixture was stirred at r.t. for 30 min, concentrated, and purified by silica column chromatography using a gradient of 0-10% MeOH in DCM as eluent to afford 8.8 g (73% over two steps) of 8-(2,4-difluorophenyl)-6,9-dioxo-5-(4-(trifluoromethyl)benzyl)-2,5,8-triazaspiro[3.5]nonane-2-carbaldehyde. LRMS (ES) m/z 469.1 (M+H); $^1$H NMR (400 MHz, Methanol-d4) δ 7.70 (d, J=8.1 Hz, 2H), 7.61-7.53 (m, 3H), 7.20 (ddd, J=10.4, 8.8, 2.8 Hz, 1H), 7.12 (dddd, J=9.1, 8.0, 2.8, 1.4 Hz, 1H), 5.15 (s, 2H), 4.53-4.49 (m, 4H), 4.20 (d, J=9.5 Hz, 2H).

Example 8

Synthesis of 8-((1r,4r)-4-(difluoromethyl)cyclohexyl)-6,9-dioxo-5-(4-(trifluoromethyl)benzyl)-2,5,8-triazaspiro[3.5]nonane-2-carbaldehyde Comparator E Step 1: Synthesis of tert-butyl 3-cyano-3-((4-(trifluoromethyl)benzyl)amino)azetidine-1-carboxylate To a solution of tert-butyl 3-oxoazetidine-1-carboxylate (25 g, 146.0 mmol, 1.0 equiv) in THF (90 mL) were added acetic acid (10.5 g, 175.2 mmol, 1.2 equiv) and (4-(trifluoromethyl)phenyl)methanamine (31.7 g, 181.1 mmol, 1.2 equiv) in water (40.0 mL). After stirring at r.t. for 5 minutes, to the mixture was added a solution of sodium cyanide (7.2 g, 146.0 mmol, 1.0 equiv) in water (10 mL) was added. The mixture was heated at 60° C. for 18 h in an oil bath, cooled to rt, neutralized by addition of a saturated aqueous solution of sodium bicarbonate, and extracted with ethyl acetate (150 mL×2). The combined organic layers were washed with brine, dried over magnesium sulfate, and concentrated under reduced pressure. To the resulting yellow solid was added diethyl ether/hexanes (200 mL, 1:2) and the solution was sonicated for a minute, cooled to 0° C., and filtered. The resulting white precipitate was washed with ice cold diethyl ether (50 mL) and dried overnight to provide tert-butyl 3-cyano-3-((4-(trifluoromethyl)benzyl)amino)azetidine-1-carboxylate (43.9 g, 85% yield). LRMS (ES) m/z 329.2 (M+H−27). $^1$H NMR (400 MHz, DMSO-d$_6$) δ 7.71 (d, J=8.0 Hz, 2H), 7.60 (d, J=8.0 Hz, 2H), 4.16 (d, J=8.8 Hz, 2H), 3.92 (t, J=7.2 Hz, 1H), 3.84 (d, J=9.2 Hz, 2H), 3.81 (dd, J=7.3 Hz, 2H), 1.39 (s, 9H).

Step 2: Synthesis of tert-butyl 3-(2-chloro-N-(4-(trifluoromethyl)benzyl)acetamido)-3-cyanoazetidine-1-carboxylate Step 3: Synthesis of tert-butyl 3-cyano-3-(2-(((1r,4r)-4-(difluoromethyl)cyclohexyl)amino)-N-(4-(trifluoromethyl)benzyl)acetamido)azetidine-1-carboxylate

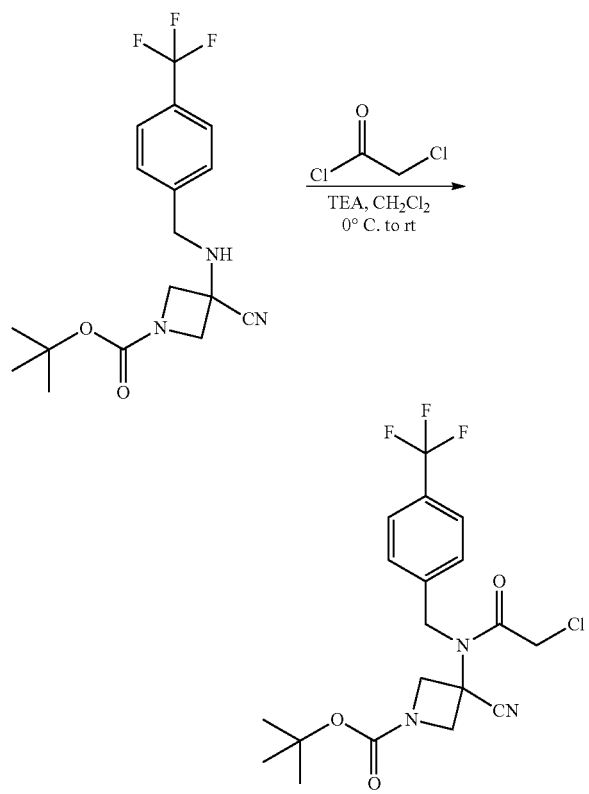

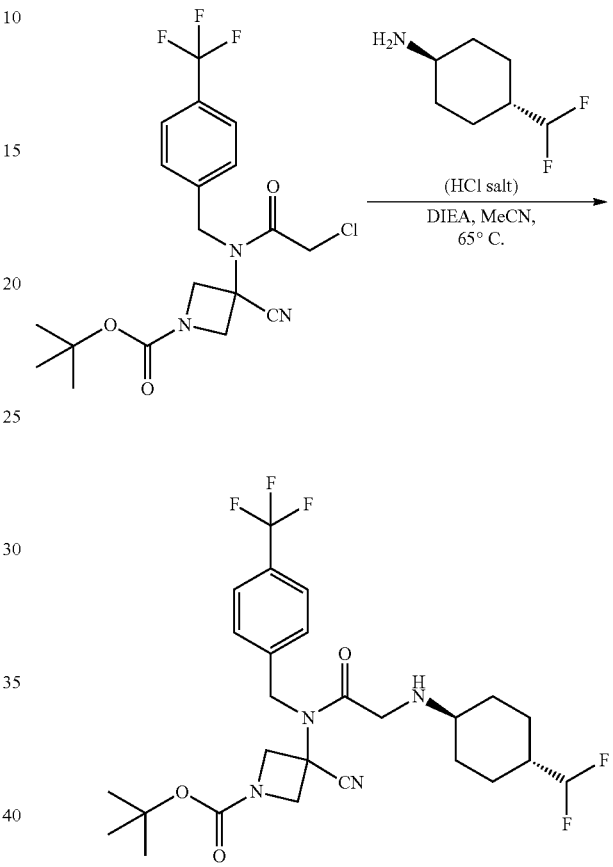

To a solution of tert-butyl 3-cyano-3-((4-(trifluoromethyl)benzyl)amino)azetidine-1-carboxylate (3.0 g, 8.4 mmol, 1.0 equiv) and triethylamine (1.3 g, 12.7 mmol, 1.5 equiv) in DCM (0.2 M) cooled to 0° C. was added chloroacetyl chloride (0.95 g, 8.4 mmol, 1.0 equiv). The mixture was stirred at 0° C. for 15 min, warmed to rt, and stirred for 2 h. To the mixture were added additional 2-chloroacetyl chloride (0.95 g, 8.4 mmol, 1.0 equiv) and triethylamine (1.3 g, 12.7 mmol, 1.5 equiv). The reaction was stirred for 2 h, quenched with a saturated aqueous solution of ammonium chloride, and separated the layers. The aqueous layer was extracted with DCM once. The combined organic layers were dried over magnesium sulfate, concentrated, and purified by silica gel column chromatography (5%-70% EtOAc/hexanes, $R_f$=0.24 (20% EtOAc/hexanes) to afford 3.4 g (92%) of tert-butyl 3-(2-chloro-N-(4-(trifluoromethyl)benzyl)acetamido)-3-cyanoazetidine-1-carboxylate. LRMS (ES) m/z 432.1 (M+H). $^1$H NMR (400 MHz, DMSO-$d_6$) δ 7.77 (d, J=8.1 Hz, 2H), 7.60 (d, J=8.0 Hz, 2H), 4.95 (s, 2H), 4.52 (s, 2H), 4.15 (s, 4H), 1.35 (s, 9H).

To a solution of tert-butyl 3-(2-chloro-N-(4-(trifluoromethyl)benzyl)acetamido)-3-cyanoazetidine-1-carboxylate (0.8 g, 1.9 mmol, 1 equiv) in acetonitrile (15 mL) were added (1r,4r)-4-(difluoromethyl)cyclohexan-1-amine hydrochloride (0.51 g, 2.8 mmol, 1.5 equiv) and DIPEA (1.2 g, 9.3 mmol, 5 equiv). The solution was heated at 65° C. for 4 h at which point LCMS indicated completion of reaction. The reaction was diluted with ethyl acetate and water (1:1, 80 mL) and the aqueous layer was extracted with ethyl acetate. The combined organic layers were washed with brine, dried over magnesium sulfate, concentrated, and purified with silica gel chromatography using a gradient of 25% to 100% ethyl acetate in hexanes as eluent to afford 0.65 g (64%) of tert-butyl 3-cyano-3-(2-(((1r,4r)-4-(difluoromethyl)cyclohexyl)amino)-N-(4-(trifluoromethyl)benzyl)acetamido)azetidine-1-carboxylate as a pale yellow oil. $R_f$=0.55 (100% ethyl acetate, silica). LRMS (ES) m/z 545.0 (M+H).

Step 4: Synthesis of tert-butyl 8-((1r,4r)-4-(difluoromethyl)cyclohexyl)-6,9-dioxo-5-(4-(trifluoromethyl)benzyl)-2,5,8-triazaspiro[3.5]nonane-2-carboxylate Step 5: Synthesis of 8-((1r,4r)-4-(difluoromethyl)cyclohexyl)-5-(4-(trifluoromethyl)benzyl)-2,5,8-triazaspiro[3.5]nonane-6,9-dione 2,2,2-trifluoroacetate

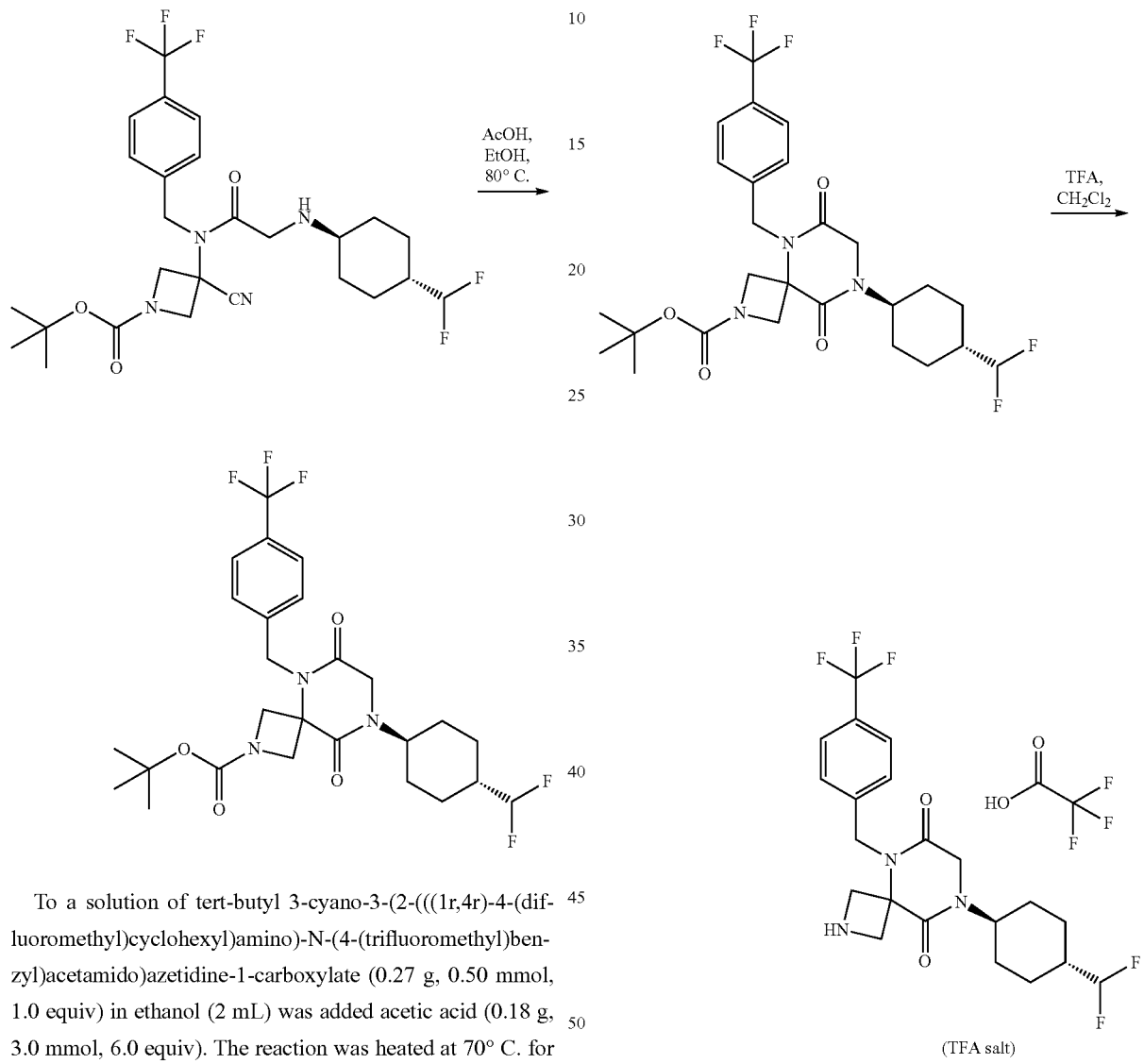

(TFA salt)

To a solution of tert-butyl 3-cyano-3-(2-(((1r,4r)-4-(difluoromethyl)cyclohexyl)amino)-N-(4-(trifluoromethyl)benzyl)acetamido)azetidine-1-carboxylate (0.27 g, 0.50 mmol, 1.0 equiv) in ethanol (2 mL) was added acetic acid (0.18 g, 3.0 mmol, 6.0 equiv). The reaction was heated at 70° C. for 15 hours, cooled to rt, and diluted with hexanes (1.0 mL). The precipitation was collected by filtration, washed with ethanol-hexanes (1:2, 2 mL), and dried to afford 186 mg (69%) of tert-butyl 8-((1r,4r)-4-(difluoromethyl)cyclohexyl)-6,9-dioxo-5-(4-(trifluoromethyl)benzyl)-2,5,8-triazaspiro[3.5]nonane-2-carboxylate as a pale yellow solid. LRMS (ES) m/z 490.2 (M+H−56). $^1$H NMR (400 MHz, DMSO-d$_6$) δ 7.71 (d, J=8.1 Hz, 2H), 7.48 (d, J=8.0 Hz, 2H), 5.89 (td, J=56.7, 3.8 Hz, 1H), 4.93 (s, 2H), 4.29-4.15 (m, 3H), 4.02 (s, 2H), 3.93 (d, J=9.5 Hz, 2H), 1.91-1.55 (m, 7H), 1.35 (s, 9H), 1.38-1.20 (m, 2H).

To a solution of tert-butyl 8-((1r,4r)-4-(difluoromethyl)cyclohexyl)-6,9-dioxo-5-(4-(trifluoromethyl)benzyl)-2,5,8-triazaspiro[3.5]nonane-2-carboxylate (200 mg, 0.37 mmol, 1.0 equiv) in DCM (1.5 mL) was added TFA (1.5 mL) at r.t. The mixture was stirred at r.t. for 1 h, concentrated under reduced pressure, and dried under high vacuum to afford 190 mg (94%) of 8-((1r,4r)-4-(difluoromethyl)cyclohexyl)-5-(4-(trifluoromethyl)benzyl)-2,5,8-triazaspiro[3.5]nonane-6,9-dione 2,2,2-trifluoroacetate, which was used without further purification. LRMS (ES) m/z 446.2 (M+H).

Step 6: Synthesis of 8-((1r,4r)-4-(difluoromethyl)cyclohexyl)-6,9-dioxo-5-(4-(trifluoromethyl)benzyl)-2,5,8-triazaspiro[3.5]nonane-2-carbaldehyde (Comparator E)

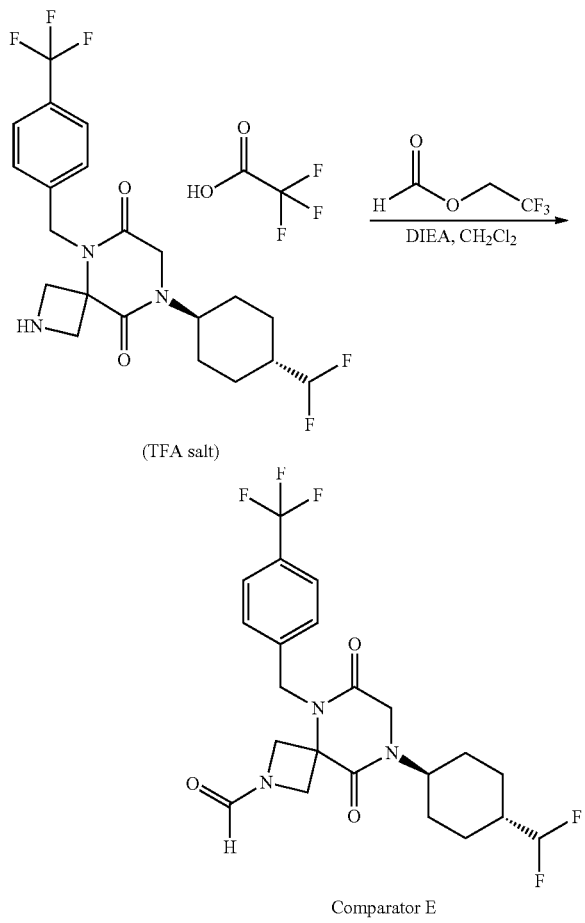

Comparator E

To a solution of 8-((1r,4r)-4-(difluoromethyl)cyclohexyl)-5-(4-(trifluoromethyl)benzyl)-2,5,8-triazaspiro[3.5]nonane-6,9-dione 2,2,2-trifluoroacetate (54.0 mg, 0.10 mmol) in acetonitrile (0.6 mL) were added DIPEA (37.0 mg, 0.29 mmol, 3.0 equiv) and 2,2,2-trifluoroethyl formate (124.0 mg, 0.97 mmol, 10.0 equiv). The mixture was heated in a microwave reactor at 110° C. for 20 min, concentrated, and purified by HPLC using a gradient of 10% to 100% ACN in water (both with 0.1% HCOOH) as eluent to afford 21.0 mg (46%) of 8-((1r,4r)-4-(difluoromethyl)cyclohexyl)-6,9-dioxo-5-(4-(trifluoromethyl)benzyl)-2,5,8-triazaspiro[3.5]nonane-2-carbaldehyde as a foam. LRMS (ES) m/z 473.9 (M+H). $^1$H NMR (400 MHz, DMSO-$d_6$) δ 7.96 (s, 1H), 7.71 (d, J=8.0 Hz, 2H), 7.47 (d, J=8.0 Hz, 2H), 5.89 (td, J=56.4, 4.5 Hz, 1H), 4.94 (s, 2H), 4.51 (d, J=9.6 Hz, 1H), 4.30-4.15 (m, 3H), 4.04 (s, 2H), 3.96 (d, J=10.7 Hz, 1H), 1.95-1.49 (m, 7H), 1.41-1.06 (m, 2H).

Biological Example B-1: Myofibril Assay

To evaluate the effect of compounds on the ATPase activity of full-length cardiac myosin in the context of the native sarcomere, skinned myofibril assays were performed. Bovine cardiac myofibrils were obtained by homogenizing bovine cardiac left ventricular tissue in the presence of a detergent such as triton X-100. Such treatment removes membranes and a majority of the soluble cytoplasmic proteins but leaves intact the cardiac sarcomeric acto-myosin apparatus. Myofibril preparations retain the ability to hydrolyze ATP in a $Ca^{2+}$ regulated manner. ATPase activities of such myofibril preparations in the presence and absence of compounds were assayed at $Ca^{2+}$ concentrations activating to a defined fraction of the maximal rate (i.e., 25%, 75%). Small molecule agents were assessed for their ability to inhibit the steady-state ATPase activity of bovine cardiac myofibrils using pyruvate kinase and lactate dehydrogenase (PK/LDH)-coupled enzyme system. This assay regenerates myosin-produced ADP into ATP by oxidizing NADH, producing an absorbance change at 340 nm. Prior to testing small molecule agents, the bovine cardiac myofibrils were assessed for their calcium responsiveness and the calcium concentration that achieves either a 50% ($pCa_{50}$) or 75% ($pCa_{75}$) activation of the myofibril system was chosen as the final condition for assessing the inhibitory activity of the small molecule agents. All enzymatic activity was measured in a buffered solution containing 12 mM PIPES (piperazine-N,N'-bis(2-ethanesulfonic acid), 2 mM magnesium chloride at pH 6.8 (PM 12 buffer). Final assay conditions were 1 mg/mL of bovine cardiac myofibrils, 4 U/mL pyruvate kinase, 6 U/mL lactate dehydrogenase, 50 μM ATP, 0.1 mg/mL BSA (bovine serum albumin), 10 ppm antifoam, 1 mM DTT, 0.5 mM NADH, 1.5 mM PEP, 0.6 mM EGTA, and an amount of $CaCl_2$ sufficient to achieve either 50% or 75% activation of the myofibril ATPase activity. Results for compounds tested are provided in Table A. Compounds tested were prepared in accordance with the synthetic procedures described herein.

TABLE A

| Compound No. | CDMF $IC_{15}$ (μM) |
| --- | --- |
| 1 | 0.80 |
| 2 | 2.1 |
| 3 | 0.7 |
| 4 | 1.5 |
| 5 | 1.3 |
| 6 | 1.4 |
| 7 | 0.8 |
| 8 | 1.3 |
| 9 | 1.6 |
| 10 | 0.3 |
| 11 | 0.7 |
| 12 | 0.4 |
| 13 | 2.0 |
| 14 | 1.3 |
| 15 | 1.4 |
| 16 | 0.9 |
| 17 | 0.9 |
| 18 | 1.2 |
| Comparator A | 1.8 |
| Comparator B | 1.1 |
| Comparator C | 1.1 |
| Comparator D | 1.1 |
| Comparator E | 1.3 |

Comparator C and Comparator D have the following structures:

| Compound | Structure | Name |
|---|---|---|
| Comparator C | 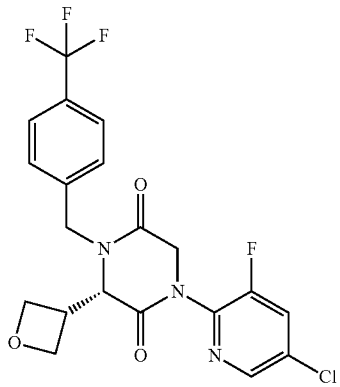 [SMILES: O=C1[C@H](C2COC2)N(Cc2ccc(C(F)(F)F)cc2)C(=O)CN1c1ncc(Cl)cc1F] | (S)-1-(5-chloro-3-fluoropyridin-2-yl)-3-(oxetan-3-yl)-4-(4-(trifluoromethyl)benzyl)piperazine-2,5-dione |
| Comparator D | 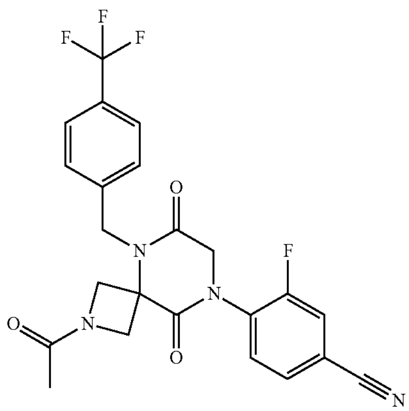 [SMILES: CC(=O)N1CC2(C1)C(=O)N(c1ccc(C#N)cc1F)CC(=O)N2Cc1ccc(C(F)(F)F)cc1] | 4-(2-acetyl-6,9-dioxo-5-(4-(trifluoromethyl)benzyl)-2,5,8-triazaspiro[3.5]nonan-8-yl)-3-fluorobenzonitrile |

The preparation of Comparator C and Comparator D is described in WO2020/047447A1.

Biological Example B-2: Pharmacokinetics Single Dose Studies

Mouse Single Dose Studies

Male C57BL/6 mice (18-25 g, 6-8 weeks old) were obtained from Zhejiang Vital River Laboratory Animal Technology Co., Ltd. All animals for IV administration had free access to food and water. The IV dosing was performed through tail vein. The IV dose solution for the Test Articles was prepared in 10% DMA/20% PG/70% HPβCD solution (40% w/v aqueous HPβCD) at a concentration of 0.1 mg/mL. The oral dosing suspension was prepared by suspending Test Article in 0.5% HPMC/0.1% Tween 80 in water at a concentration 0.2 mg/mL. Concentrations of IV and PO doses were measured at the end of the study. Pharmacokinetic (PK) parameters were calculated using the nominal dose values if the measured values were within 20% of the nominal values. A group of 15 mice received the IV dose where the volume was 5 mL/kg. Another group of 15 mice received by oral gavage of Test Article at 1 mg/kg. The oral dose volume was 5 mL/kg. Sparse blood samples were collected from groups of three mice via retro-orbital bleeding, placed into a $K_2$EDTA microtainer tube and maintained on ice until centrifugation to obtain plasma. Each designated group of mice were bled at two-time points. The time points were predose (PO only), 5 (IV only), 15, 30 minutes, 1, 2, 4, 6, 8 and 24 hours postdose. Blood samples were centrifuged and the collected plasma was stored at −80° C. until analysis. Plasma samples were analyzed for Test Article concentrations using an LC/MS/MS method. Briefly, a 50 µL aliquot of each plasma sample was mixed with 100 µL of acetonitrile that contained an internal standard (IS). The mixture was vortexed and centrifuged. Ten (10) µL of the resulting solution was injected onto a reverse-phase C18 column and the resultant peaks detected on a LC/MS/MS equipped with a turbo ionspray ionization source. Sample concentrations below the limit of quantification (BLQ) were treated as zero for PK calculations. Composite PK parameters were estimated from a maximum of two sampling points per mouse and three mice per sampling point and the sparse data option of WinNonlin was used for noncompartmental analysis of the concentration-time data (Phoenix WinNonLin software, version 64; Pharsight, Mountain View, CA). The elimination rate constant (k) was calculated as the absolute value of the slope of the linear regression of logarithm of the concentration versus time for the last three data points of the concentration-time profiles. Apparent elimination half-life ($t_{1/2}$) values were calculated as ln(2)/k. Area under the concentration-time curve (AUC) values were estimated using linear trapezoidal method. $AUC_t$ values were calculated from the dosing time to the last measurable concentration. $AUC_\infty$ values were calculated as the sum of the corresponding $AUC_t$ and the ratio of the last detectable concentration divided by k. Plasma clearance (CL) was calculated from Dose/$AUC_\infty$. Mean resident time (MRT) was estimated by moment analysis. Volume of distribution at steady state ($V_{ss}$) was calculated from $MRT_\infty \times CL$. Maximum concentration ($C_{max}$) and time to reach $C_{max}$ ($t_{max}$) were recorded as observed. Bioavailability was calculated $dAUC_{\infty,po}/dAUC_{\infty,iv} \times 100\%$ where dAUC was the dose normalized AUC value. Data for compounds tested are provided in Table B. Compounds tested were prepared in accordance with the synthetic procedures described herein.

TABLE B

| Compound No. | CL (mL/min/kg) | t½ (h) | $V_{ss}$ (L/kg) |
|---|---|---|---|
| 4 | 28.4 | 1.77 | 4.2 |
| 5 | 18.9 | 3.08 | 4.08 |
| 6 | 28.2 | 1.27 | 2.52 |
| 7 | 15 | 2.5 | 2.95 |
| 8 | 132 | 0.66 | 5.14 |
| 13 | 101 | 0.46 | 2.25 |
| 18 | 21 | 1.18 | 2.95 |
| Comparator B | 21.45 | 2.96 | 4.51 |
| Comparator C | 4.67 | 2.6 | 1.39 |
| Comparator E | 11.6 | 2.8 | 3.28 |

Rat Single Dose Studies

Male Sprague Dawley rats were obtained from Zhejiang Vital River Laboratory Animal Technology Co., Ltd. The animals in IV group had free access to water and food. The animals in PO group were fasted overnight before dosing and provided with food 2 hours post dosing. The IV dose solution was prepared in 10% DMA/50% PG/40% HPβCD solution (40% w/v aqueous HPβCD) at a concentration of 1 mg/mL. The oral dosing suspension was prepared by suspending Test Article in 0.5% HPMC/0.1% Tween 80 in water at a concentration 0.2 mg/mL. Concentrations of IV and PO doses were measured at the end of the study. Pharmacokinetic parameters were calculated using the nominal dose values if the measured values were within 20% of the nominal values. Three rats were dosed IV via a bolus injection via caudal vein. Three rats per dose group were dosed by oral gavage. Blood samples were collected from the jugular vein cannula at predose, 5 (IV only), 15, 30 minutes, and 1, 2, 4, 6, and 24 hours post-dose. Blood volumes were replaced with an equal amount of sterile 0.9% saline. Blood samples were centrifuged and the collected plasma was stored at −80° C. for subsequent analysis. Plasma samples were analyzed for Test Article concentrations using a LC/MS/MS method. Briefly, a 50 µL aliquot of each plasma sample was mixed with 100 µL of acetonitrile that contained an internal standard. The mixture was vortexed and centrifuged. Ten (10) L of the resulting solution was injected onto a reverse-phase C18 column and the resultant peaks detected on a LC/MS/MS equipped with a turbo ionspray ionization source. Sample concentrations below the limit of quantification (BLQ) were treated as zero for pharmacokinetic calculations. Pharmacokinetic parameters were estimated from individual animals using noncompartmental analysis of the concentration-time data (Phoenix WinNonLin software, version 64; Pharsight, Mountain View, CA). The elimination rate constant (k) was calculated as the absolute value of the slope of the linear regression of logarithm (log) of the concentration versus time for the last three data points of the concentration-time profiles. Apparent elimination half-life ($t_{1/2}$) values were calculated as ln(2)/k. Area under the concentration-time curve (AUC) values were estimated using linear trapezoidal method. $AUC_t$ values were calculated from the dosing time to the last measurable concentration. $AUC_\infty$ values were calculated as the sum of the corresponding $AUC_t$ and the ratio of the last detectable concentration divided by k ($AUC_{t-\infty}$). Plasma clearance (CL) was calculated from $Dose/AUC_\infty$. Mean resident time (MRT) was estimated by moment analysis. Volume of distribution at steady state ($V_{ss}$) was calculated from $MRT_\infty \times CL$. Maximum concentration ($C_{max}$) and time to reach $C_{max}$ ($t_{max}$) were recorded as observed. Bioavailability was calculated from the ratio of dose normalized $AUC_{\infty,po}$ of individual rats/mean $dAUC_{\infty,iv} \times 100\%$ where dAUC was the dose normalized AUC value. Data for compounds tested are provided in Table C. Compounds tested were prepared in accordance with the synthetic procedures described herein.

TABLE C

| Compound No. | CL (mL/min/kg) | t½(h) | $V_{ss}$ (L/kg) |
|---|---|---|---|
| 3 | 78.49 | 2.6 | 14.7 |
| 4 | 52.57 | 3.34 | 12.98 |
| 5 | 71.07 | 3.04 | 13.7 |
| 6 | 76.6 | 2 | 10.1 |
| 7 | 61.93 | 2.1 | 12.6 |
| 8 | 79.91 | 1.2 | 5.22 |
| 9 | 27.4 | 0.925 | 1.64 |
| 13 | 38.9 | 0.95 | 2.17 |
| 18 | 63.6 | 2.15 | 9.48 |
| Comparator A | 29.59 | 6.48 | 15.05 |
| Comparator B | 41.86 | 5.87 | 16.58 |
| Comparator C | 20.23 | 3.3 | 5.2 |
| Comparator D | 8.23 | 4.84 | 2.98 |
| Comparator E | 18.75 | 5.4 | 8.23 |

Dog Single Dose Studies

Non-naïve male beagle dogs (8 months-3 years of age, body weight 8-13 kg) were used in this study. All animals for IV administration had free access to food and water; all animals for PO were fasted overnight prior to dosing and were fed approximately 6 hours after dosing. For the animals in PO group, pentagastrin (6.0 µg/kg, i.m.) was administrated 20 minutes before dosing PO formulation and 1.5 hours after the first pentagastrin dosing. The dosing volume was 0.024 mL/kg, the concentration was 250 µg/mL in DMSO/1 N NaOH/PBS. 10 mL of 0.001 N HCl was used to wash the gavage catheter for each animal. The IV dose solution was prepared in 10% DMA/50% PG/40% HPβCD solution (40% w/v aqueous HPβCD) at a concentration of 1.0 mg/mL. The oral dose suspension was prepared by suspending the compound in 0.5% HPMC/0.1% Tween 80 in distilled water at a concentration of 0.2 mg/mL. Concentrations of IV and PO doses were measured at the end of the study. PK parameters were calculated using the nominal dose values if the measured values were within 20% of the nominal values. Blood samples were collected by venipuncture of peripheral veins except the dosing vein at pre-dose, 5 15, 30 min, 1, 2, 4, 6, 8, 24 and 48 h post-dose. Blood samples were centrifuged and resultant plasma was frozen for bioanalysis. Plasma samples were stored at −80° C. before analysis. Plasma samples were analyzed for compound concentrations using the LC/MS/MS method. Briefly, a 50 µL aliquot of each plasma sample was mixed with 100 µL of acetonitrile that contained an internal standard. The mixture was vortexed and centrifuged. Ten (10) µL of the resulting solution was injected onto a reverse-phase C18 column and the resultant peaks detected on a LC/MS/MS equipped with a turbo ionspray ionization source. Sample concentrations below the limit of quantification (BLQ) were treated as zero for PK calculations. PK parameters were estimated from individual animals using noncompartmental analysis of the concentration-time data (Phoenix WinNon- Lin software, version 64; Pharsight, Mountain View, CA). The elimination rate constant (k) was calculated as the absolute value of the slope of the linear regression of logarithm (log) of the concentration versus time for the last three data points of the concentration-time profiles. Apparent elimination half-life ($t_{1/2}$) values were calculated as ln(2)/k. Area under the concentration-time curve (AUC) values were estimated using linear trapezoidal method. $AUC_t$ values were calculated from the dosing time to the last measurable concentration. $AUC_\infty$ values were calculated as the sum of the corresponding $AUC_t$ and the ratio of the last detectable concentration divided by k. Plasma clearance (CL) was calculated from Dose/$AUC_\infty$. Mean resident time extrapolated to infinity ($MRT_\infty$) was estimated by moment analysis. $V_{ss}$ was calculated from $MRT_\infty \times CL$. Maximum concentration ($C_{max}$) and time to reach $C_{max}$ ($t_{max}$) were recorded as observed. As this was a cross-over study, bioavailability was calculated $dAUC_{\infty,po}/dAUC_{\infty,iv} \times 100\%$ where dAUC was the dose normalized AUC value from the same animal given IV and PO dose. Data for compounds tested are provided in Table D. Compounds tested were prepared in accordance with the synthetic procedures described herein.

TABLE D

| Compound No. | CL (mL/min/kg) | t½ (h) | $V_{ss}$ (L/kg) |
|---|---|---|---|
| 4 | 7.57 | 9.54 | 4.23 |
| 13 | 7.45 | 6.44 | 2.85 |
| 18 | 18.8 | 5.8 | 5.73 |
| Comparator A | 1.59 | 39.17 | 5.2 |
| Comparator B | 2.39 | 45.88 | 6.51 |
| Comparator C | 4.92 | 14.66 | 5.91 |
| Comparator D | 3.55 | 23.69 | 6.7 |
| Comparator E | 1.49 | 33.1 | 4.1 |

Monkey Single Dose Studies

Non-naïve Male Cynomolgus Monkey (2-5 years of age, body weight 2-5 kg) used in this study were obtained from Topgene Biotechnology. All animals for IV administration had free access to food and water; all animals for PO were fasted overnight prior to dosing and were fed approximately 6 hours after dosing. The IV dose solution was prepared in 10% DMA/50% PG/40% HPβCD solution (40% w/v aqueous HPβCD) at a concentration of 1.0 mg/mL. The oral dose suspension was prepared by suspending the compound in 0.5% HPMC/0.1% Tween 80 in distilled water at a concentration of 0.2 mg/mL. Concentrations of IV and PO doses were measured at the end of the study. PK parameters were calculated using the nominal dose values if the measured values were within 20% of the nominal values. Blood samples were collected by venipuncture of peripheral veins except the dosing vein at pre-dose, 5 15, 30 min, 1, 2, 4, 6, 8, 24 and 48 h post-dose. Blood samples were centrifuged and resultant plasma was frozen for bioanalysis. Plasma samples were stored at −80° C. before analysis. Plasma samples were analyzed for compound concentrations using the LC/MS/MS method. Briefly, a 50 μL aliquot of each plasma sample was mixed with 100 μL of acetonitrile that contained an internal standard. The mixture was vortexed and centrifuged. Ten (10) μL of the resulting solution was injected onto a reverse-phase C18 column and the resultant peaks detected on a LC/MS/MS equipped with a turbo ionspray ionization source. Sample concentrations below the limit of quantification (BLQ) were treated as zero for PK calculations. PK parameters were estimated from individual animals using noncompartmental analysis of the concentration-time data (Phoenix WinNonLin software, version 64; Pharsight, Mountain View, CA). The elimination rate constant (k) was calculated as the absolute value of the slope of the linear regression of logarithm (log) of the concentration versus time for the last three data points of the concentration-time profiles. Apparent elimination half-life ($t_{1/2}$) values were calculated as ln(2)/k. Area under the concentration-time curve (AUC) values were estimated using linear trapezoidal method. $AUC_t$ values were calculated from the dosing time to the last measurable concentration. $AUC_\infty$ values were calculated as the sum of the corresponding $AUC_t$ and the ratio of the last detectable concentration divided by k. Plasma clearance (CL) was calculated from Dose/$AUC_\infty$. Mean resident time extrapolated to infinity ($MRT_\infty$) was estimated by moment analysis. $V_{ss}$ was calculated from $MRT_\infty \times CL$. Maximum concentration ($C_{max}$) and time to reach $C_{max}$ ($t_{max}$) were recorded as observed. As this was a cross-over study, bioavailability was calculated $dAUC_{\infty,po}/dAUC_{\infty,iv} \times 100\%$ where dAUC was the dose normalized AUC value from the same animal given IV and PO dose. Data for compounds tested are provided in Table E. Compounds tested were prepared in accordance with the synthetic procedures described herein.

TABLE E

| Compound No. | CL (mL/min/kg) | t½ (h) | $V_{ss}$ (L/kg) |
|---|---|---|---|
| 4 | 11.6 | 9.94 | 8.89 |
| 13 | 25.8 | 2.05 | 3.98 |
| 18 | 7.91 | 10.9 | 6.08 |
| Comparator B | 8.72 | 16.22 | 9.96 |
| Comparator C | 13.78 | 11.56 | 12.03 |
| Comparator D | 6.92 | 18.12 | 12.43 |
| Comparator E | 3.4 | 16 | 4.35 |

Projected Single-Dose CL and $V_{ss}$ Values in Humans

Allometric scaling for the prediction of human Clearance and Volume of Distribution was based on interspecies simple allometric scaling of mouse, rat, dog, and cynomolgus monkey intravenous pharmacokinetic parameters (Boxenbaum, J Pharmacokinet Biopharm 10:201-27, 1982). Prediction of human CL was performed by extrapolating preclinical species' plasma intravenous clearance. The 'rule of exponents' (Mahmood & Balian, Life Sci 59:579-85, 1996) was examined in this prediction, where it has been proposed that, when the exponent of simple allometry lies between 0.71 and 0.99, a correction factor based on Maximum Life Span (MLP) of this species can be applied and, when the exponent of simple allometry is greater than 1.0, a correction factor based on Brain Weight (BrW) can be applied, or a protein binding correction can be applied when available. In a similar manner, simple allometric scaling was employed to predict human Volume of Distribution. This method has been used successfully for varied drugs (Ward & Smith, Drug Metab Dispos 32:612-19, 2004; McGinnity et al., Curr Drug Metab 8:463-79, 2007). Projected data for selected compounds are provided in Table F.

TABLE F

| Compound No. | Projected CL (mL/min/kg) | Projected t½ (h) | Projected t½ Method | Projected $V_{ss}$ (L/kg) |
| --- | --- | --- | --- | --- |
| 4 | 1.84 | 28.3 | SA, ROE, MLP correction, fu correction | 4.51 |
| 13 | 4.66 | 8.51 | SA, ROE, fu correction | 3.43 |
| 18 | 3.3 | 25 | SA, ROE, BrW correction | 7.1 |
| Comparator A | 1.44 | 38.7 | SA, fu correction | 41.2 |
| Comparator B | 1.96 | 54.5 | SA, ROE, fu correction | 9.25 |
| Comparator C | 3.9 | 41 | SA, ROE, MLP correction, fu correction | 13.9 |
| Comparator D | 0.96 | 62 | SA, ROE, MLP correction, fu correction | 5.16 |
| Comparator E | 1.2 | 51.7 | SA, ROE, fu correction | 5.5 |

Key for Table F:
SA = Simple Allometry;
ROE = Rule of Exponents;
fu correction = function unbound in plasma correction;
MLP correction = Maximum Life Span Correction;
BrW correction = Brain Weight correction Dog Cassette Dosing Non-naïve male beagle dogs (8 months to 3 years of age, body weight 8-14 kg) sourced from Jiangsu Johnsen Bioresource CO. and/or Beijing Rixinkeji CO., LTD and/or Beijing Marshall Biotechnology CO., LTD were used in this study. All animals for IV administration had free access to food and water. The IV dose solution was prepared in 10% DMA/50% PG/40% HPβCD solution (40% w/v aqueous HPβCD) at a concentration of 0.2 mg/mL. Concentrations of IV dose was measured at the end of the study. PK parameters were calculated using the nominal dose values if the measured values were within 20% of the nominal values. Blood samples were collected by venipuncture of peripheral veins except the dosing vein at pre-dose, 5 15, 30 min, 1, 2, 4, 6, 8 and 24 h post-dose. Blood samples were centrifuged and resultant plasma was frozen for bioanalysis. Plasma samples were stored at –80° C. before analysis. Plasma samples were analyzed for compound concentrations using the LC/MS/MS method. Briefly, a 50 µL aliquot of each plasma sample was mixed with 100 µL of acetonitrile that contained an internal standard. The mixture was vortexed and centrifuged. Ten (10) µL of the resulting solution was injected onto a reverse-phase C18 column and the resultant peaks detected on a LC/MS/MS equipped with a turbo ionspray ionization source. Sample concentrations below the limit of quantification (BLQ) were treated as zero for PK calculations. PK parameters were estimated from individual animals using noncompartmental analysis of the concentration-time data (Phoenix WinNonLin software, version 64; Pharsight, Mountain View, CA). The elimination rate constant (k) was calculated as the absolute value of the slope of the linear regression of logarithm (log) of the concentration versus time for the last three data points of the concentration-time profiles. Apparent elimination half-life ($t_{1/2}$) values were calculated as ln(2)/k. Area under the concentration-time curve (AUC) values were estimated using linear trapezoidal method. $AUC_t$ values were calculated from the dosing time to the last measurable concentration. $AUC_\infty$ values were calculated as the sum of the corresponding $AUC_t$ and the ratio of the last detectable concentration divided by k. Plasma clearance (CL) was calculated from Dose/$AUC_\infty$. Mean resident time extrapolated to infinity ($MRT_\infty$) was estimated by moment analysis. $V_{ss}$ was calculated from $MRT_\infty \times CL$. Maximum concentration ($C_{max}$) and time to reach $C_{max}$ ($t_{max}$) were recorded as observed. As this was a cross-over study, bioavailability was calculated $dAUC_{\infty,po}$/$dAUC_{\infty,iv} \times 100\%$ where dAUC was the dose normalized AUC value from the same animal given IV and PO dose. Data for compounds tested are provided in Table G. Compounds tested were prepared in accordance with the synthetic procedures described herein.

TABLE G

| Compound No. | CL (mL/min/kg) | t½ (h) | $V_{ss}$ (L/kg) |
| --- | --- | --- | --- |
| 1 | 3.65 | 12.5 | 3.44 |
| 2 | 4.06 | 7.34 | 1.99 |
| 3 | 7.16 | 13.1 | 6.9 |
| 4 | 5.12 | 11.8 | 4.48 |
| 5 | 9.26 | 9.86 | 6.17 |
| 6 | 9.08 | 7.11 | 3.98 |
| 7 | 9.22 | 10.9 | 6.33 |
| 8 | 15.6 | 5.66 | 6.26 |
| 9 | 13.9 | 3.65 | 3.08 |
| 10 | 36.3 | 9.38 | 18.6 |
| 11 | 6.3 | 9.66 | 4.42 |
| 12 | 34.4 | 7.39 | 17.8 |
| 13 | 11.5 | 4.16 | 3.72 |
| 14 | 36.5 | 2.43 | 6.44 |
| 15 | 24.2 | 1.49 | 2.84 |
| 16 | 33 | 3.07 | 7.08 |
| 17 | 41.9 | 3.02 | 8.25 |
| 18 | 7.07 | 9.08 | 4.29 |

Monkey Cassette Dosing

Non-naïve male beagle dogs (2-5 years of age, body weight 2-5 kg) sourced from Topgene Biotechnology were used in this study. All animals for IV administration had free access to food and water. The IV dose solution was prepared in 10% DMA/50% PG/40% HPβCD solution (40% w/v aqueous HPβCD) at a concentration of 0.2 mg/mL. Concentrations of IV dose was measured at the end of the study.

PK parameters were calculated using the nominal dose values if the measured values were within 20% of the nominal values. Blood samples were collected by venipuncture of peripheral veins except the dosing vein at pre-dose, 5 15, 30 min, 1, 2, 4, 6, 8 and 24 h post-dose. Blood samples were centrifuged and resultant plasma was frozen for bioanalysis. Plasma samples were stored at −80° C. before analysis. Plasma samples were analyzed for compound concentrations using the LC/MS/MS method. Briefly, a 50 µL aliquot of each plasma sample was mixed with 100 µL of acetonitrile that contained an internal standard. The mixture was vortexed and centrifuged. Ten (10) µL of the resulting solution was injected onto a reverse-phase C18 column and the resultant peaks detected on a LC/MS/MS equipped with a turbo ionspray ionization source. Sample concentrations below the limit of quantification (BLQ) were treated as zero for PK calculations. PK parameters were estimated from individual animals using noncompartmental analysis of the concentration-time data (Phoenix WinNonLin software, version 64; Pharsight, Mountain View, CA). The elimination rate constant (k) was calculated as the absolute value of the slope of the linear regression of logarithm (log) of the concentration versus time for the last three data points of the concentration-time profiles. Apparent elimination half-life ($t_{1/2}$) values were calculated as ln(2)/k. Area under the concentration-time curve (AUC) values were estimated using linear trapezoidal method. $AUC_t$ values were calculated from the dosing time to the last measurable concentration. $AUC_\infty$ values were calculated as the sum of the corresponding $AUC_t$ and the ratio of the last detectable concentration divided by k. Plasma clearance (CL) was calculated from Dose/$AUC_\infty$. Mean resident time extrapolated to infinity ($MRT_\infty$) was estimated by moment analysis. $V_{ss}$ was calculated from $MRT_\infty \times CL$. Maximum concentration ($C_{max}$) and time to reach $C_{max}$ ($t_{max}$) were recorded as observed. As this was a cross-over study, bioavailability was calculated $dAUC_{\infty,po}/dAUC_{\infty,iv} \times 100\%$ where dAUC was the dose normalized AUC value from the same animal given IV and PO dose. Data for compounds tested are provided in Table H. Compounds tested were prepared in accordance with the synthetic procedures described herein.

TABLE H

| Compound No. | CL (mL/min/kg) | t½ (h) | $V_{ss}$ (L/kg) |
|---|---|---|---|
| 4 | 13.1 | 8.69 | 8.8 |
| 5 | 19 | 8.2 | 10.2 |
| 6 | 12.3 | 8.07 | 6.29 |
| 7 | 10.2 | 12.5 | 9.12 |
| 8 | 20.2 | 3.72 | 4.76 |
| 9 | 15.2 | 1.59 | 1.88 |
| 11 | 33.1 | 3.03 | 7.26 |
| 13 | 21.4 | 1.83 | 3.15 |
| 14 | 17.1 | 1.1 | 1.48 |
| 18 | 12.5 | 8.04 | 10.2 |

Projected Cassette-Dosing CL and $V_{ss}$ Values in Humans

For PK data derived from Cassette IV dosing, predictions of Human Clearance and Volume of Distribution were performed using Single Species allometry. In this case values were predicted from plasma intravenous Clearance of Dog and Monkey PK by applying protein binding correction (Tang, Drug Metab Dispos 33:1294-96, 2005; Patel, Journal of Pharmaceutical Research International, 22(3): 1-7, 2018). Projected data for selected compounds are provided in Table J and Table K.

TABLE J

| Compound No. | Projected Human Single Species Allometry: Dog CL (mL/min/kg) | Projected Human Single Species Allometry: Dog t½ V (h) | Projected Human Single Species Allometry: Dog $V_{ss}$ (L/kg) |
|---|---|---|---|
| 1 | 1.5 | 11.2 | 24.1 |
| 2 | 1.3 | 5.8 | 10.8 |
| 3 | 3.2 | 28.8 | 52.5 |
| 4 | 1.5 | 25.8 | 22 |
| 5 | 4.6 | 19.8 | 52 |
| 6 | 1.5 | 13.2 | 11.1 |
| 7 | 3.6 | 20.4 | 42 |
| 8 | 5.98 | 12.00 | 41 |
| 9 | 5 | 2.6 | 18.8 |
| 10 | 14.9 | 6.1 | 130.2 |
| 11 | 2.6 | 8.3 | 30.9 |
| 12 | 14.1 | 6.1 | 124.6 |
| 13 | 4.8 | 9.6 | 26.8 |
| 14 | 15 | 2.1 | 45.1 |
| 15 | 9.92 | 1.4 | 19.9 |
| 16 | 13.51 | 2.5 | 49.6 |
| 17 | 17.17 | 2.3 | 57.8 |
| 18 | 3.6 | 18.00 | 36.9 |

TABLE K

| Compound No. | Projected Human Single Species Allometry: Monkey CL (mL/min/kg) | Projected Human Single Species Allometry: Monkey t½(h) | Projected Human Single Species Allometry: Monkey $V_{ss}$ (L/kg) |
|---|---|---|---|
| 4 | 3.1 | 15.84 | 71 |
| 5 | 6.4 | 12.72 | 118 |
| 6 | 1.9 | 12.24 | 32.6 |
| 7 | 3.5 | 21.36 | 108 |
| 8 | 6.8 | 5.52 | 55 |
| 9 | 4.8 | 2.88 | 20.3 |
| 11 | 13.5 | 5.2 | 101.6 |
| 13 | 6.7 | 3.6 | 33.6 |
| 14 | 7 | 2.1 | 20.7 |
| 18 | 4.3 | 19.44 | 121.4 |

Biological Example B-3: Echocardiography Assessment of Acute Pharmacodynamic Effect in Rat Cardiac Contractility Assessment of in vivo cardiac function by echocardiography was performed in male Sprague Dawley rats under isoflurane (1-3%) anesthesia. 2-D M-mode images of the left ventricle were acquired in the parasternal long-axis view before, during, and after administration of compounds. In vivo fractional shortening was determined by M-mode image analysis with the following calculation: ((End diastolic diameter−end systolic diameter)! end diastolic diameter×100). Three pre-dose baseline M-Mode images were taken at 1-minute intervals prior to compound administration. Compounds were formulated in a 0.5% hydroxypropyl methylcellulose 2910 (HPMC 2910): 0.1% Tween 80 suspension and delivered as a single dose (5 mL/kg) by oral gavage. At one and four hours post-dose, rats were lightly anesthetized for M-mode echocardiography measurement. Concurrent with echocardiography measurements, blood samples were taken to determine the corresponding compound plasma concentrations. The resulting plasma concentrations were used to estimate the $IC_{50}$ and $IC_{10}$ values, which is the concentration at which fractional shortening is 50% and 10% of the pre-dose baseline contractility, respectively.

TABLE L

IC50, IC10 values and IC50/IC10 ratio

| Compound No. | IC$_{10}$ (μM) | IC$_{50}$ (μM) | IC$_{50}$/IC$_{10}$ |
|---|---|---|---|
| 4 | 0.284 | 2.763 | 9.73 |
| 5 | 1.17 | 4.439 | 3.79 |
| 8 | 0.508 | 2.253 | 4.44 |
| 13 | 0.317 | 1.172 | 3.7 |
| 18 | 0.892 | 2.835 | 3.18 |

Biological Example B-4: In Vitro Determination of Time-Dependent Inhibition of CYP450 Enzymes An assessment of the time-dependent Inhibitory Potential of the test compounds against Principal Human Cytochrome P450 Isozymes using Human Liver Microsomes was also carried out using standard methods (Grimm et al, *Drug Metab. Dispos.*, July; 37(7):1355-70. doi: 10.1124/dmd.109.026716, 2009). Pooled human microsomes and selective CYP probe substrates were used for in vitro assessment of test compounds at 25 and 50 μM as time-dependent inhibitors of seven human hepatic cytochrome P450 isozymes (CYP1A2, 2B6, 2C9, 2C19, 2D6, and 3A4). LC-MS/MS was used to quantify metabolite formation. The inhibition of each P450 enzyme in human liver microsomes was measured as the percentage decrease in the activity of marker metabolite formation as measured by LC-MS/MS compared to non-inhibited controls (=100% activity) at time zero and after 30 minutes incubation. The occurrence of any time dependent inhibition was then expressed as the fold change in enzyme activity at time zero relative to the activity after 30 minutes incubation.

TABLE M

Time Dependent Inhibition for tested compounds against CYP1A2, CYP2B6, CYP2C8, CYP2C9, CYP2C19, CYP2D6, CYP3A4-M and CYP3A4-T

| Compound No. | Conc (μM) | % Activity NADPH T0 | % Activity NADPH T30 | (% Activity NADPH T0)/(% Activity NADPH T30) | % Activity NADPH T0 | % Activity NADPH T30 | (% Activity NADPH T0)/(% Activity NADPH T30) |
|---|---|---|---|---|---|---|---|
| | | CYP1A2 | | | CYP2B6 | | |
| Comparator C | 25 | NA | NA | NA | NA | NA | NA |
| | 50 | NA | NA | NA | NA | NA | NA |
| 18 | 25 | 85 | 99 | 0.9 | 80 | 103 | 0.8 |
| | 50 | 92 | 90 | 1.0 | 76 | 83 | 0.9 |
| 5 | 25 | 89 | 87 | 1.0 | 79 | 78 | 1.0 |
| | 50 | 99 | 88 | 1.1 | 83 | 76 | 1.1 |
| 4 | 25 | 95 | 90 | 1.1 | 95 | 84 | 1.1 |
| | 50 | 86 | 85 | 1.0 | 76 | 76 | 1.0 |
| 6 | 25 | 97 | 85 | 1.1 | 95 | 83 | 1.1 |
| | 50 | 95 | 99 | 1.0 | 87 | 77 | 1.1 |
| 7 | 25 | 81 | 95 | 0.9 | 70 | 74 | 0.9 |
| | 50 | 79 | 100 | 0.8 | 78 | 70 | 1.1 |
| 8 | 25 | 82 | 96 | 0.9 | 83 | 97 | 0.9 |
| | 50 | 86 | 101 | 0.9 | 88 | 100 | 0.9 |
| 13 | 25 | 88 | 99 | 0.9 | 102 | 116 | 0.9 |
| | 50 | 92 | 110 | 0.8 | 90 | 81 | 1.1 |
| | | CYP2C9 | | | CYP2C19 | | |
| Comparator C | 25 | NA | NA | NA | NA | NA | NA |
| | 50 | NA | NA | NA | NA | NA | NA |
| 18 | 25 | 44 | 47 | 0.9 | 103 | 99 | 1.0 |
| | 50 | 32 | 27 | 1.2 | 91 | 84 | 1.1 |
| 5 | 25 | 62 | 79 | 0.8 | 101 | 83 | 1.2 |
| | 50 | 62 | 64 | 1.0 | 102 | 77 | 1.3 |
| 4 | 25 | 83 | 84 | 1.0 | 117 | 86 | 1.4 |
| | 50 | 63 | 71 | 0.9 | 84 | 75 | 1.1 |
| 6 | 25 | 48 | 41 | 1.2 | 105 | 89 | 1.2 |
| | 50 | 34 | 33 | 1.0 | 100 | 92 | 1.1 |
| 7 | 25 | 94 | 75 | 1.3 | 87 | 87 | 1.0 |
| | 50 | 87 | 61 | 1.4 | 82 | 83 | 1.0 |
| 8 | 25 | 104 | 107 | 1.0 | 94 | 99 | 0.9 |
| | 50 | 112 | 109 | 1.0 | 93 | 92 | 1.0 |
| 13 | 25 | 107 | 114 | 0.9 | 108 | 108 | 1.0 |
| | 50 | 111 | 109 | 1.0 | 113 | 119 | 0.9 |
| | | CYP2D6 | | | CYP2C8 | | |
| Comparator C | 25 | NA | NA | NA | NA | NA | NA |
| | 50 | NA | NA | NA | NA | NA | NA |
| 18 | 25 | 103 | 105 | 1.0 | 65 | 100 | 0.7 |
| | 50 | 104 | 91 | 1.1 | 100 | 76 | 1.3 |
| 5 | 25 | 98 | 89 | 1.1 | 87 | 88 | 1.0 |
| | 50 | 94 | 84 | 1.1 | 104 | 53 | 2.0 |
| 4 | 25 | 118 | 90 | 1.3 | 79 | 80 | 1.0 |
| | 50 | 93 | 88 | 1.1 | 97 | 79 | 1.2 |
| 6 | 25 | 112 | 87 | 1.3 | 79 | 88 | 0.9 |
| | 50 | 107 | 92 | 1.2 | 86 | 80 | 1.1 |

TABLE M-continued

Time Dependent Inhibition for tested compounds against CYP1A2, CYP2B6, CYP2C8, CYP2C9, CYP2C19, CYP2D6, CYP3A4-M and CYP3A4-T

| Compound No. | Conc (µM) | % Activity NADPH T0 | % Activity NADPH T30 | (% Activity NADPH T0)/(% Activity NADPH T30) | % Activity NADPH T0 | % Activity NADPH T30 | (% Activity NADPH T0)/(% Activity NADPH T30) |
|---|---|---|---|---|---|---|---|
| 7 | 25 | 80 | 88 | 0.9 | 72 | 64 | 1.1 |
|   | 50 | 87 | 95 | 0.9 | 109 | 103 | 1.1 |
| 8 | 25 | 92 | 98 | 0.9 | 117 | 117 | 1.0 |
|   | 50 | 87 | 91 | 1.0 | 110 | 112 | 1.0 |
| 13 | 25 | 96 | 100 | 1.0 | 116 | 98 | 1.2 |
|   | 50 | 98 | 72 | 1.4 | 106 | 106 | 1.0 |
|   |   | CYP3A4-T | | | CYP3A4-M | | |
| Comparator C | 25 | 41 | 23 | 1.8 | 75 | 48 | 1.6 |
|   | 50 | 35 | 19 | 1.8 | 57 | 33 | 1.7 |
| 18 | 25 | 100 | 85 | 1.2 | 125 | 71 | 1.8 |
|   | 50 | 85 | 75 | 1.1 | 126 | 102 | 1.2 |
| 5 | 25 | 100 | 87 | 1.1 | 75 | 69 | 1.1 |
|   | 50 | 98 | 68 | 1.4 | 67 | 35 | 1.9 |
| 4 | 25 | 80 | 90 | 0.9 | 70 | 88 | 0.8 |
|   | 50 | 83 | 98 | 0.8 | 57 | 78 | 0.7 |
| 6 | 25 | 95 | 76 | 1.3 | 89 | 89 | 1.0 |
|   | 50 | 89 | 63 | 1.4 | 72 | 86 | 0.8 |
| 7 | 25 | 100 | 100 | 1.0 | 100 | 100 | 1.0 |
|   | 50 | 100 | 100 | 1.0 | 100 | 100 | 1.0 |
| 8 | 25 | 100 | 100 | 1.0 | 100 | 100 | 1.0 |
|   | 50 | 100 | 100 | 1.0 | 100 | 100 | 1.0 |
| 13 | 25 | 74 | 77 | 1.0 | 87 | 88 | 1.0 |
|   | 50 | 56 | 65 | 0.9 | 72 | 97 | 0.7 |

NA: not available;
CYP3A4-T: CYP3A4 activity as measured by the testosterone probe substrate;
CYP3A4-M: CYP3A4 activity as measured by the midazolam probe substrate For 3A4, measuring the % activity using both midazolam and testosterone as probes, compound 13, compound 8, compound 7 and compound 4 do not show any indication of time dependent inhibition since the activity of the enzyme did not change by greater than 1.2 fold. Comparator C however did show a change in fold activity of >1.5 fold for both probes at the 25 and 50 µM concentrations. Compound 18, compound 5, and compound 6 also showed some change in the fold activity >1.2 fold either at one of the concentrations tested or with one of the probe substrates studies suggesting that there may be some change in 3A4 activity when tested in time dependent format for these compounds. All the compounds tested showed no change in activity for 1A2 and 2B6 when tested in this format. For 2C9, compound 7 only showed a 1.3 fold change in activity at the 25 µM concentration and a 1.3 fold change in activity at the 50 µM concentration. For 2C19, compound 5 showed a 1.3 fold change in activity at the 50 µM concentration and compound 4 showed a 1.4 fold change in activity at the 25 µM concentration, although no change in activity was observed for compound 4 at the 50 µM concentration. For 2D6, compound 13 showed a 1.4 fold change in activity at the 50 µM concentration and compound 6 and compound 4 showed a 1.3 fold change in activity at the 25 µM concentration, although no change in activity was observed for these compounds at the 50 µM concentration. For 2C8, compound 18 showed a 1.3 fold change in activity at the 50 µM concentration and compound 5 showed a 2.0 fold change in activity at the 50 µM concentration.

While the foregoing written description of the compounds, uses, and methods described herein enables one of ordinary skill to make and use the compounds, uses, and methods described herein, those of ordinary skill will understand and appreciate the existence of variations, combinations, and equivalents of the specific embodiment, method, and examples herein. The compounds, uses, and methods provided herein should therefore not be limited by the above-described embodiments, methods, or examples, but rather encompasses all embodiments and methods within the scope and spirit of the compounds, uses, and methods provided herein.

All references disclosed herein are incorporated by reference in their entirety.

The invention claimed is:
1. A method of treating a heart disease in a subject in need thereof, comprising administering to the subject a compound of formula:

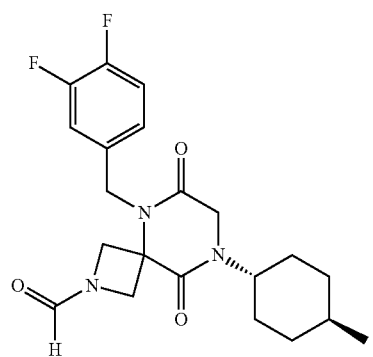 [SMILES: C[C@H]1CC[C@H](N2CC(=O)N(Cc3ccc(F)c(F)c3)C3(CN(C=O)C3)C2=O)CC1]

or a pharmaceutically acceptable salt thereof.

2. The method of claim 1, wherein the heart disease is hypertrophic cardiomyopathy.

3. The method of claim 2, wherein the hypertrophic cardiomyopathy is obstructive or nonobstructive or is caused by (i) sarcomeric mutations, (ii) non-sarcomeric mutations, or (iii) both sarcomeric mutations and non-sarcomeric mutations.

4. The method of claim 1, wherein the heart disease is heart failure with preserved ejection fraction.

5. The method of claim 1, wherein the heart disease is selected from the group consisting of diastolic dysfunction, primary or secondary restrictive cardiomyopathy, myocardial infarction and angina pectoris, left ventricular outflow tract obstruction, hypertensive heart disease, congenital heart disease, cardiac ischemia, coronary heart disease, diabetic heart disease, congestive heart failure, right heart failure, cardiorenal syndrome, and infiltrative cardiomyopathy.

6. The method of claim 1, wherein the heart disease is or is related to one or more conditions selected from the group consisting of cardiac senescence, diastolic dysfunction due to aging, left ventricular hypertrophy, and concentric left ventricular remodeling.

7. A method of treating a disease or condition associated with hypertrophic cardiomyopathy in a subject in need thereof, comprising administering to the subject a compound of formula:

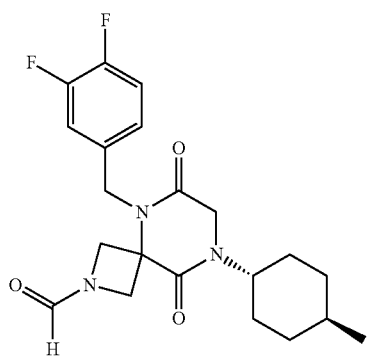 [SMILES: C[C@H]1CC[C@H](N2CC(=O)N(Cc3ccc(F)c(F)c3)C3(CN(C=O)C3)C2=O)CC1]

or a pharmaceutically acceptable salt thereof.

8. The method of claim 7, wherein the disease or condition is selected from the group consisting of Fabry's Disease, Danon Disease, mitochondrial cardiomyopathies, and Noonan Syndrome.

9. A method of treating a disease or condition that is associated with secondary left ventricular wall thickening in a subject in need thereof, comprising administering to the subject a compound of formula:

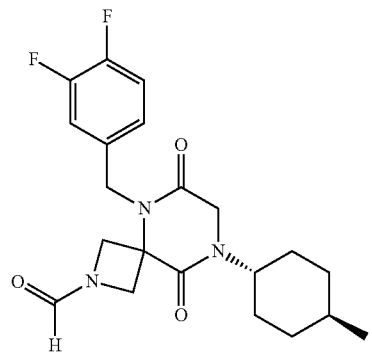 [SMILES: C[C@H]1CC[C@H](N2CC(=O)N(Cc3ccc(F)c(F)c3)C3(CN(C=O)C3)C2=O)CC1]

or a pharmaceutically acceptable salt thereof.

10. The method of claim 9, wherein the disease or condition is selected from the group consisting of hypertension, valvular heart diseases, aortic stenosis, Mitral valve regurgitation, metabolic syndromes, diabetes, obesity, end stage renal disease, scleroderma, sleep apnea, amyloidosis, Fabry's disease, Friedreich Ataxia, Danon disease, Noonan syndrome, and Pompe disease.

11. A method of treating a disease or condition that is associated with small left ventricular cavity and cavity obliteration, hyperdynamic left ventricular contraction, myocardial ischemia, or cardiac fibrosis in a subject in need thereof, comprising administering to the subject a compound of formula:

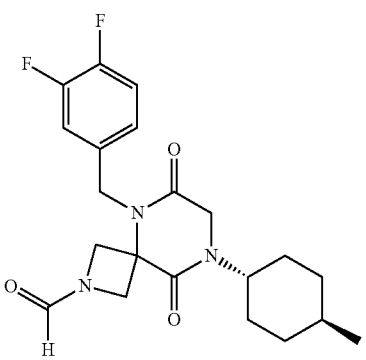 [SMILES: C[C@H]1CC[C@H](N2CC(=O)N(Cc3ccc(F)c(F)c3)C3(CN(C=O)C3)C2=O)CC1]

or a pharmaceutically acceptable salt thereof.

12. A method of treating heart failure with preserved ejection fraction in a subject in need thereof, comprising administering to the subject a compound of formula:

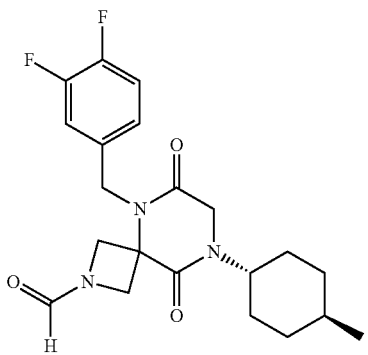

13. A method of inhibiting a cardiac sarcomere, comprising contacting the cardiac sarcomere with a compound of formula:

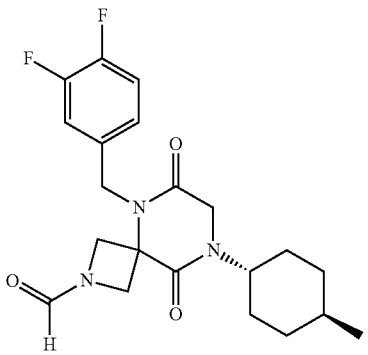 [SMILES: C[C@H]1CC[C@H](N2CC(=O)N(Cc3ccc(F)c(F)c3)C3(CN(C=O)C3)C2=O)CC1]

or a pharmaceutically acceptable salt thereof.

14. The method of claim 3, wherein the hypertrophic cardiomyopathy is caused by sarcomeric mutations.

15. The method of claim 14, wherein the sarcomeric mutation is a mutation in myosin heavy chain β (MHC-β), cardiac muscle troponin T (cTnT), tropomyosin alpha-1 chain (TPM1), myosin-binding protein C cardiac-type (MYBPC3), cardiac troponin 1 (cTnI), myosin essential light chain (ELC), titin (TTN), myosin regulatory light chain 2 ventricular/cardiac muscle isoform (MLC-2), cardiac muscle alpha actin, or muscle LIM protein (MLP).

16. The method of claim 15, wherein the sarcomeric mutation is a mutation in MHC-β.

17. The method of claim 15, wherein the sarcomeric mutation is a mutation in cTnT.

18. The method of claim 15, wherein the sarcomeric mutation is a mutation in MYBPC3.

19. The method of claim 3, wherein the hypertrophic cardiomyopathy is caused by non-sarcomeric mutations.

20. The method of claim 19, wherein the non-sarcomeric mutation is a mutation in protein kinase AMP-activated non-catalytic subunit gamma 2 (PRKAG2).

* * * * *

UNITED STATES PATENT AND TRADEMARK OFFICE
CERTIFICATE OF CORRECTION

Page 1 of 1

PATENT NO. : 12,286,437 B2
APPLICATION NO. : 18/423156
DATED : April 29, 2025
INVENTOR(S) : Bradley P. Morgan et al.

It is certified that error appears in the above-identified patent and that said Letters Patent is hereby corrected as shown below:

In the Claims

At Column 116, Claim number 15, Line number 5, delete "troponin 1" and insert -- troponin I --.

Signed and Sealed this
Eighteenth Day of November, 2025

John A. Squires
*Director of the United States Patent and Trademark Office*